US008060945B2

(12) United States Patent
Adarraga

(10) Patent No.: US 8,060,945 B2
(45) Date of Patent: Nov. 22, 2011

(54) SAFETY AND CONTROL EXOSKELETON FOR SNOW SKIING

(75) Inventor: Juan Moran Adarraga, Tarragona (ES)

(73) Assignee: Goldon Crab S.L., Madrid (ES)

( * ) Notice: Subject to any disclaimer, the term of this patent is extended or adjusted under 35 U.S.C. 154(b) by 834 days.

(21) Appl. No.: 12/103,410

(22) Filed: Apr. 15, 2008

(65) Prior Publication Data

US 2008/0287850 A1    Nov. 20, 2008

Related U.S. Application Data

(63) Continuation of application No. PCT/ES2008/000242, filed on Apr. 14, 2008.

(60) Provisional application No. 60/907,913, filed on Apr. 23, 2007, provisional application No. 60/907,914, filed on Apr. 23, 2007, provisional application No. 61/035,918, filed on Mar. 12, 2008, provisional application No. 61/035,924, filed on Mar. 12, 2008.

(51) Int. Cl.
    *A41D 13/00* (2006.01)
(52) U.S. Cl. .......................................................... 2/22
(58) Field of Classification Search .................. 128/882, 128/108.1; 602/26, 62; 280/611; 2/22, 16, 2/24, 62, 911
    See application file for complete search history.

(56) References Cited

U.S. PATENT DOCUMENTS

| | | |
|---|---|---|
| 2,803,467 A | 8/1957 | von Opel |
| 3,614,119 A | 10/1971 | Wilkes |
| 3,826,509 A | 7/1974 | Smolka |
| 3,909,028 A | 9/1975 | Courvoisier et al. |
| 3,928,872 A | 12/1975 | Johnson |
| 3,947,051 A | 3/1976 | Sittmann |
| 4,136,404 A | 1/1979 | Lange |
| 4,408,600 A | 10/1983 | Davis |
| 4,420,895 A | 12/1983 | Baumann et al. |
| 4,568,296 A | 2/1986 | Newell |

(Continued)

FOREIGN PATENT DOCUMENTS

CN    1593861 A    3/2005

(Continued)

OTHER PUBLICATIONS

Umetami, Y. et al., "'Skil Mate', Wearable Exoskeleton Robot" 1999 IEEE International Conference on Systems, Man, and Cybernetics, 1999. IEEE SMC '99 Conference Proceedings 1999 0-7803-5731-0/99.

(Continued)

*Primary Examiner* — Tejash Patel
(74) *Attorney, Agent, or Firm* — Sughrue Mion, PLLC

(57) ABSTRACT

Exoskeleton for physical activity, specially snow skiing, for preventing knee, leg and hip injuries by preventing the excessive torsion of the knee and other movements that could be dangerous for the person wearing it, furthermore allowing control over the skis during the practice of said sport. The exoskeleton includes at least one first support member configured to couple above the knee; at least one second support member configured to couple below the knee; both of them linked together by a linkage assembly that limits that the coupling to the body of the support members reach dangerous positions; at least one clutch mechanism operatively coupled between two elements of the exoskeleton, allowing the clutching and unclutching of said two elements of the exoskeleton; and at least one sensor that detects movement or/and pressure, of a part of the body of the skier to transmit a signal to the clutch mechanism.

73 Claims, 40 Drawing Sheets

U.S. PATENT DOCUMENTS

| | | | |
|---|---|---|---|
| 4,617,920 A | | 10/1986 | Carsalade |
| 4,776,326 A | | 10/1988 | Young et al. |
| 4,872,665 A | | 10/1989 | Chareire |
| 4,967,734 A | | 11/1990 | Rennex |
| 5,011,136 A | | 4/1991 | Rennex |
| 5,016,869 A | | 5/1991 | Dick et al. |
| 5,295,704 A | * | 3/1994 | Flock .......................... 280/611 |
| 5,362,288 A | | 11/1994 | Razon |
| 5,376,139 A | | 12/1994 | Pitkin |
| 5,405,408 A | | 4/1995 | Pitkin |
| 5,845,540 A | | 12/1998 | Rosheim |
| 5,961,541 A | | 10/1999 | Ferrati |
| 5,980,435 A | * | 11/1999 | Joutras et al. ................ 482/114 |
| 6,239,784 B1 | | 5/2001 | Holmes |
| 6,397,496 B1 | | 6/2002 | Seymour |
| 6,524,110 B1 | | 2/2003 | Eastwood |
| 6,666,796 B1 | | 12/2003 | MacCready, Jr. |
| 6,746,248 B2 | | 6/2004 | Eastwood |
| 6,853,965 B2 | | 2/2005 | Massie et al. |
| 7,004,494 B2 | | 2/2006 | Wulf et al. |
| 7,153,242 B2 | | 12/2006 | Goffer |
| 7,164,967 B2 | | 1/2007 | Etienne-Cummings et al. |
| 7,190,141 B1 | * | 3/2007 | Ashrafiuon et al. ..... 318/568.12 |
| 7,549,969 B2 | * | 6/2009 | van den Bogert ............ 602/16 |
| 7,571,839 B2 | * | 8/2009 | Chu et al. ..................... 224/637 |
| 7,833,134 B2 | * | 11/2010 | Gordon ........................... 482/52 |
| 7,845,017 B2 | * | 12/2010 | Godshaw et al. ................. 2/24 |
| 2002/0094919 A1 | | 7/2002 | Rennex et al. |
| 2002/0110793 A1 | | 8/2002 | Eastwood |
| 2003/0093021 A1 | | 5/2003 | Goffer |
| 2003/0223844 A1 | | 12/2003 | Schiele et al. |
| 2004/0106881 A1 | | 6/2004 | McBean et al. |
| 2005/0108900 A1 | | 5/2005 | Knowles |
| 2005/0251079 A1 | | 11/2005 | Carvey et al. |
| 2006/0046907 A1 | | 3/2006 | Rastegar et al. |
| 2006/0046908 A1 | | 3/2006 | Rastegar et al. |
| 2006/0046909 A1 | | 3/2006 | Rastegar et al. |
| 2006/0046910 A1 | | 3/2006 | Rastegar et al. |
| 2006/0064047 A1 | | 3/2006 | Shimada et al. |
| 2006/0247904 A1 | | 11/2006 | Dariush |
| 2006/0260620 A1 | | 11/2006 | Kazerooni et al. |
| 2007/0061016 A1 | | 3/2007 | Kuo et al. |
| 2007/0123997 A1 | | 5/2007 | Herr et al. |

FOREIGN PATENT DOCUMENTS

| | | |
|---|---|---|
| EP | 1 400 438 A2 | 3/2004 |
| ES | 295.785 Y | 5/1988 |
| FR | 1.549.497 A | 12/1968 |
| WO | 2005/092452 A1 | 10/2005 |
| WO | 2006/107716 A2 | 10/2006 |
| WO | 2006/113520 A2 | 10/2006 |

OTHER PUBLICATIONS

Pratt, Jerry E. et al. "The RoboKnee: An Exoskeleton for Enhancing Strength and Endurance During Walking" Proceedings of the 2004 IEEE Int'l Conf. on Robotics & Automation Apr. 2004.

CBC News website "Scientists invent bionic boots to ease load for soldiers" Mar. 11, 2004 (http://www.cbc.ca/health/story/2004/03/11/bionic_boots040311.html, viewed Jun. 4, 2007).

Gordon, K.E., Ferris, D.P., Learning to walk with a robotic ankle exoskeleton. Journal of Biomechanics (2007), doi:10.1016/j.jbiomech.2006.12.006.

Kramer, Andrew E., "Gas-Powered Footwear's Fate Shows Frustrations of Russian Inventors" New York Times Mar. 17, 2007 p. C1.

Kramer, Andrew E., "These Boots Were Made for 22 M.P.H." New York Times Mar. 17, 2007 p. C1.

International Search Report for PCT/ES2008/000242 dated Aug. 8, 2008.

* cited by examiner

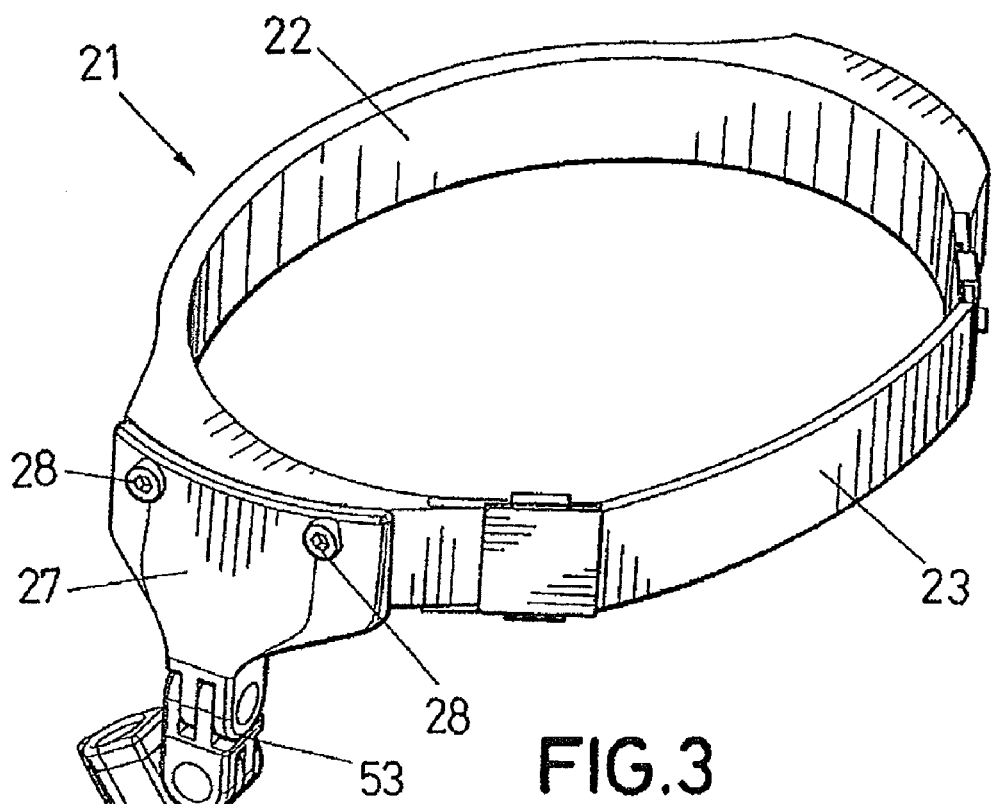
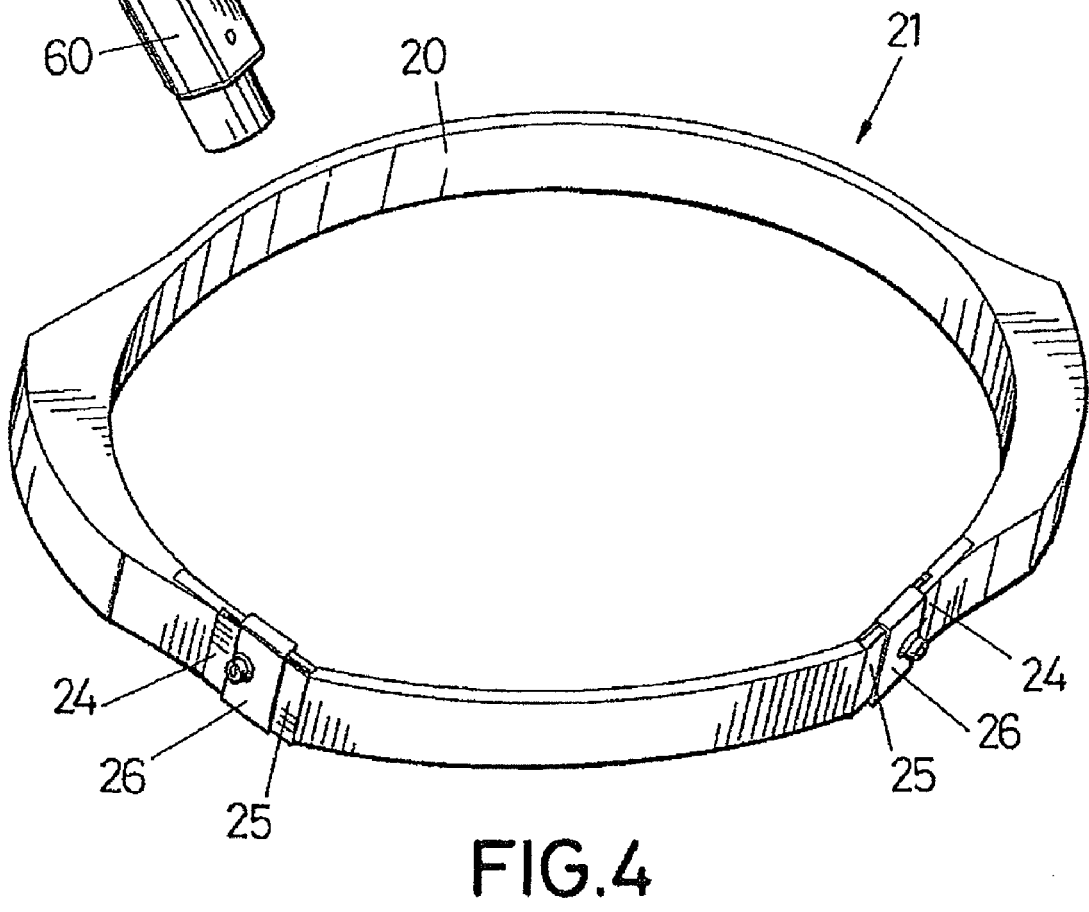

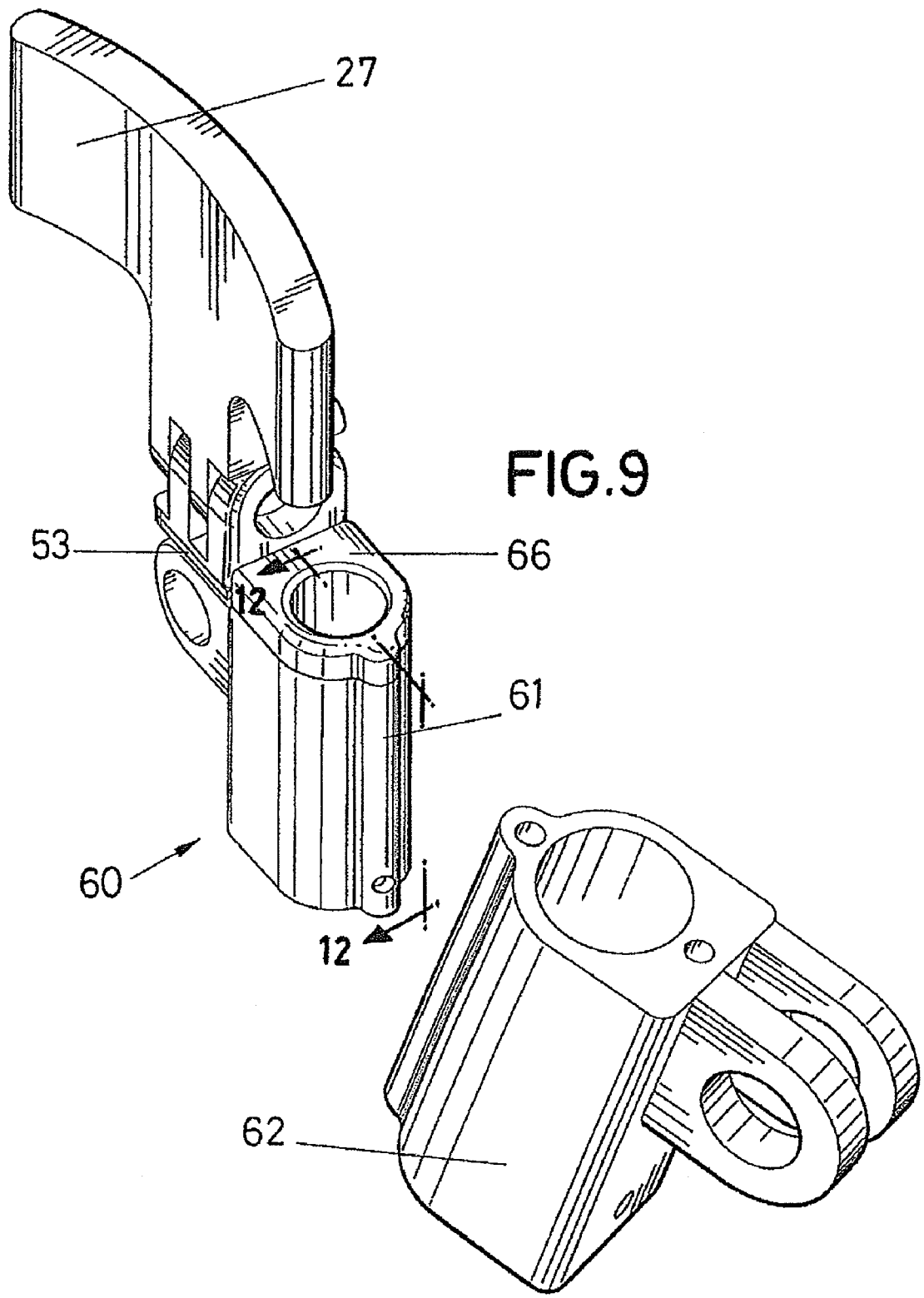

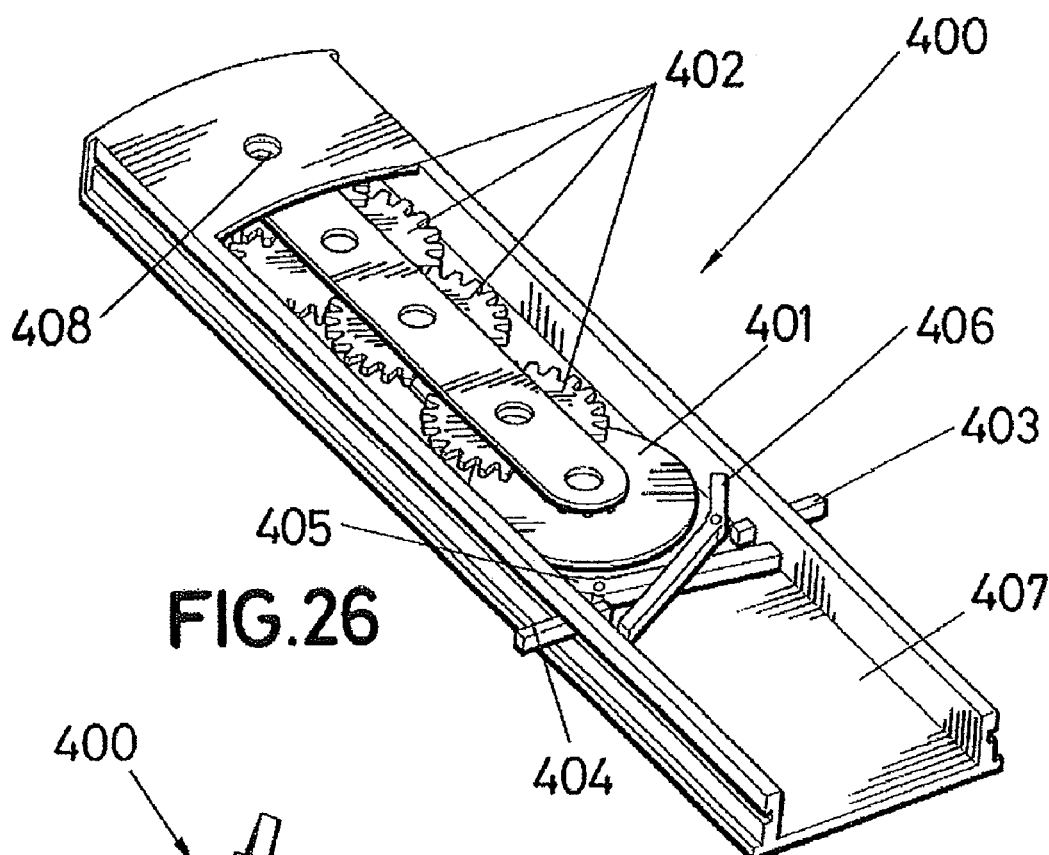
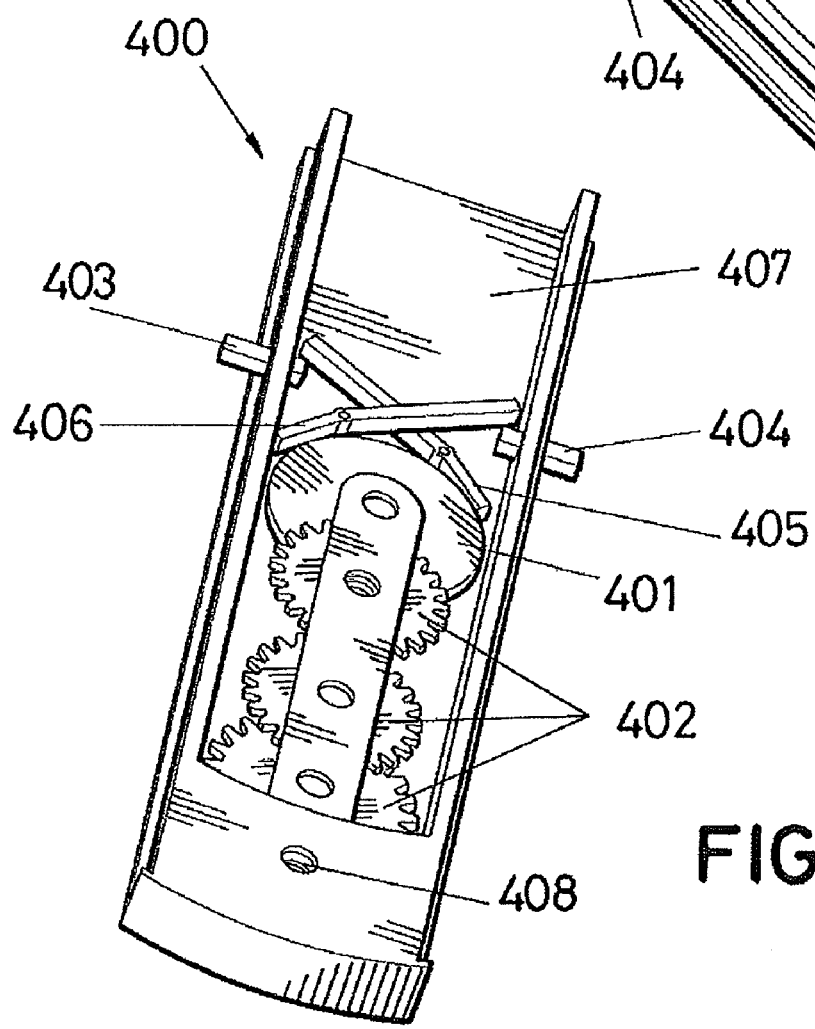

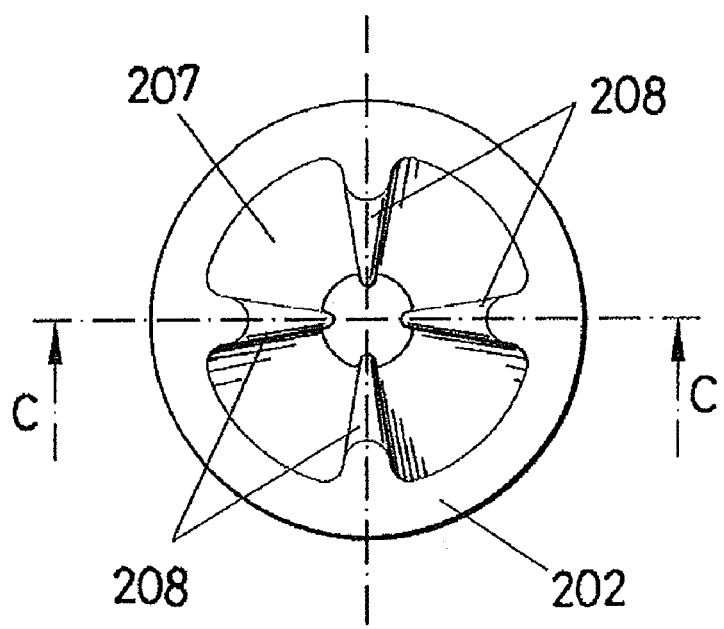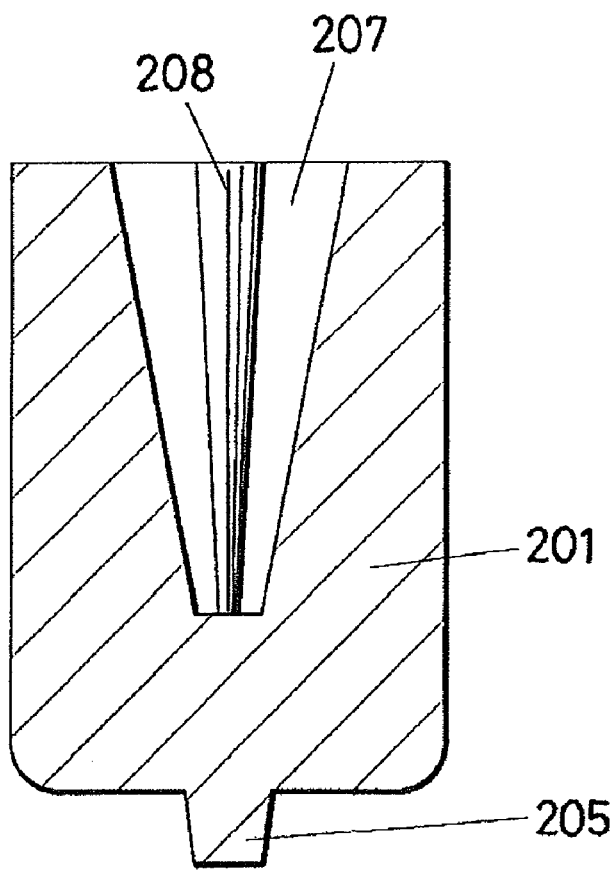
FIG.32

SAFETY AND CONTROL EXOSKELETON FOR SNOW SKIING

This application is a continuation of International Application No. PCT/ES2008/000242, filed Apr. 14, 2008; and claims the benefit of U.S. Provisional Application 61/035,918, filed Mar. 12, 2008; U.S. Provisional Application 61/035,924, filed Mar. 12, 2008; U.S. Provisional Application 60/907,914, filed Apr. 23, 2007; and U.S. Provisional Application 60/907,913, filed Apr. 23, 2007, their entire contents of which are incorporated herein by reference.

TECHNICAL FIELD

The present invention, a safety device for snow skiing, relates to a device which makes skiing a safer and easier sport. The device has been designed with a special emphasis on preventing knee injuries, as this is the joint that suffers the most damage in accidents occurring while practicing this sport. Nevertheless, the protection provided by the device of this invention is not limited to the knee joint, but can also provide protection to the leg as a whole and, in most of the preferred embodiments, the hip as well.

The invention also relates to a device which, in addition to assuring the skier's safety also allows control of the skis while practicing the sport, preventing them from being diverted against the user's or skier's wishes, such that the skier will suffer fewer accidents and will therefore suffer fewer injuries of all types.

The preferred field of application for the invention is skiing, particularly downhill skiing. Although the present invention may also be useful for other sports involving the risk of joint or bone injury. Therefore, everything that is explained below could also be used, with the logical adaptations, for the protection of other athletes and people who practice activities that involve the risk of bone injuries in general and joint injuries particularly.

BACKGROUND

Every year downhill skiing causes many serious knee injuries involving ligament and meniscal tears, despite the efforts that have been made in the industry to improve the bindings, the devices for attaching the boot to the ski, and therefore the skier or athlete to the skis.

These injuries often force the patient to quit skiing or practicing many other sports, or undergo major surgery, with certain risks and doubts, often very painful and long recoveries, changes in lifestyle with the respective work, family, professional, psychological and financial drawbacks resulting from the injury.

Other possible injuries while skiing, which follow knee injuries in number, are head and face injuries, but the use of a helmet to protect against these injuries is becoming increasingly widespread.

Currently, the annual total number of skiers per year between the United States and Europe is about 20 million.

The total number of accidents involving serious injuries entailing caring for and evacuating injured persons from the slope is about between two and four per every thousand. Out of one thousand days skied by a skier, one will be injured between 2 and four times (in the United States, this figure is about 3.5 per thousand days).

Skiing also becomes difficult on many occasions due to the amplification of the force that any uneven terrain will have through the large lever of the skies on the skier's foot, making the skier lose his or her path and causing instability.

As previously mentioned, skiing involves a high risk of knee ligament and meniscal injuries (between 30% and 40% of the total), among other injuries. Such injuries are frequently caused by the large forces that knees are subjected to because of the stress transmitted thereto through the rigid boot from the skis, which act as large levers as illustrated in FIG. 1A.

There are different knee injuries, but the most common ones in skiing are external lateral ligament tears (between 20 and 25% of injuries) and the anterior cruciate ligament tears (between 10 and 15% of injuries).

The injury to the external collateral ligament normally affects beginners and intermediate level skiers, who ski mainly in the wedge position, with the feet facing inwards, and who are injured during a fall, when the skis cross over one another or the wedge opens up. Injury to the external lateral ligament can occur in more experienced skiers usually when a ski strikes against an obstacle, the ski opens up and the leg tries to hold on to it.

The injury to the anterior cruciate ligament occurs under different conditions, especially in more experienced skiers, and can occur, for example:

When the rear part of the ski acts as a lever with the boot, exerting a rotational force, twisting and bending the knee;

When the skier falls backwards during a jump and instinctively straightens his or her leg and therefore falls on the rear part of the ski, forcing the rear part of the boot against the calf thereby deviating the tibia under the femur and tearing the cruciate ligament; or When a skier is upright and is hit from behind on the lower part of the leg, forcing the tibia forwards with the subsequent damage to the cruciate ligament.

Other injuries include damage to the meniscus (between 5 and 10% of all injuries), caused by torsional stress applied to the flexed knee and usually caused when an obstacle is struck at a high speed.

Currently, bindings holding the boot to the ski are relied upon for reducing the risk of injury, but they do not adequately prevent such risk. Bindings are designed so that the boot is released from the ski when a specific and previously established pressure limit is surpassed. However, depending on the posture of the leg at the time of the demand of the force and of other factors, such as the severity of the impact, it is possible that the binding does not behave as expected. In such cases, the binding does not come undone and the boot is not released from the ski at the appropriate time or at all, frequently causing the ligaments of the knee to tear before the mechanism can release the boot.

This system furthermore forces the skier to choose a certain setting. If the binding is too tight, it is hard for the ski to separate from the boot at a torsion of the ski that is large enough to risk injury to the knee. If, on the other hand, the bindings are too loose, a skier may, at an inconvenient moment, involuntarily lose a ski, which could also cause a serious injury.

Nor do current bindings contribute to the stability of skis or to the skier's desire to stay on his or her path.

As previously mentioned, these knee injuries usually bring about an expensive surgical intervention with a long and uncomfortable recovery, results that are not always satisfactory and significant repercussions in terms of work, family, etc.

The known devices of the state of the art, do not provide a protection and control over the skis as the one of the exoskeleton of the present invention.

Different devices for preventing ski injuries are known. For example, United States patent document number US-4136404-B1 discloses an athletic leg brace apparatus configured to be connected to the sides of a ski boot and divided into two parts along the leg by a hinge at the height of the knee, such that an upper part is attached to the thigh and a lower part to the boot. The device allows flexion and extension movement of the leg, restricting the lateral flexion of both parts of the leg and allowing the transmission of lateral forces of the skier's legs to the lateral parts of the boot. In other words, the purpose of this device is to reduce the lateral flexion of a skier's legs when he or she is skiing, so as to protect the bones of the leg, not the joints, in the event of flexion. Furthermore, this device does not protect the leg in the case of torsion, which is the stress causing the most common and significant knee injuries, especially when the knee is extended. Another limitation of the mechanism protected by the mentioned US patent is that, since the leg is firmly attached to the boot by the mechanism of the described invention, the freedom of movement is quite compromised when the knee is flexed, negatively affecting the skiing experience, unlike the present invention. Additionally, the device described in US-4136404-B1 has no element for attachment to or support by the waist. All the stress is confined exclusively to the leg. An object of several embodiments of the present invention, on the other hand, is to use the waist as a strong area of the body for supporting the entire reinforcement structure and preventing leg injuries. Nor does US-4136404-B1 incorporate any ski control device. Another object of several embodiments of the present invention, however, is to allow efficient and effective control of the skis at all times. This involves a significant improvement of the active safety conditions in addition to making the skiing experience much more satisfactory.

Another limitation of the US-4136404-B1 is that since the leg is "embraced" at the thigh and attached to the boot in the manner described in that patent, the freedom of movement is quite compromised, negatively affecting the skiing experience, unlike the device according to the present invention.

An object of the present invention is to allow improved freedom of movement of the leg at all times, except that the leg is supported by the protective structure at those times when it is necessary and particularly in the direction of unwanted movements. In other words, it allows improved or complete freedom of wanted movements and restricts unwanted movements induced by the ski.

U.S. Pat. No. 3,947,051-B1 describes a binding for a ski boot with a transmitter located between the skier's leg and boot to initiate the "release" operation of the binding during falls, particularly forward falls. The transmitter detects an excessive force between the leg and the boot, thus transmitting an instruction to release the binding, preventing leg injuries in the skier. However, as will be understood, the present invention is completely different from the foregoing:

It does not require the replacement of the boot-ski binding mechanism, but rather can be complementary to it;

It is not limited to the boot-ski attachment, and provides a boot-leg and, in several of the preferred embodiments, hip connecting elements (exoskeleton);

elements of the present invention can transmit the torsion or torque generated at the foot due to the lever effect of the ski to the entire exoskeleton structure and through it to the strong areas of the leg and, in most of the preferred embodiments, to a part located at the skier's waist or hips, thereby protecting against dangerous torsion of the knee joint;

the device, being attached to strong areas of the body, can withstand the torsion or torque generated in the foot due to the lever of the ski in limit or extreme positions that may injure the knee, such that the resultant forces are not transmitted to the much weaker knee joint, and which until now no system or mechanism has been able to effectively protect as proven by the previously mentioned statistics;

the present application significantly reinforces the corporal structure in the areas of the body that are most involved in skiing, which allows tighter setting of the bindings with the assurance that no injury will occur, because in most cases the skier will be supported by the reinforced structure of the exoskeleton, and in extreme cases, the binding would come undone without affecting the structure of the knee or any other leg joint or bone.

None of the previous features or functionalities are present in U.S. Pat. No. 3,947,051-B1, whereas the present invention allows one to achieve this functionalities.

A system that significantly increases the skier's resistance to unwanted movements of the ski is also an object of the present invention. This system diverts part of the torque that an unwanted rotation of the ski causes on the foot to the structure formed by the exoskeleton, to the strong parts of the leg to which the structure is attached to and, in several of the preferred embodiments, the waist or hips. In addition to increasing safety, this helps considerably in controlling the skis. This feature is also not present in the device described in US-3947051-B1 or other conventional support mechanisms.

United States patent application publication number US-2006260620-A1 describes a lower extremity exoskeleton that is coupled to a person and configured such that both leg supports are used to be supported on the ground when the user is stopped. The exoskeleton is formed by a link in the thigh, another one in the calf and two joints at the height of the knee, these joints allow the extension and flexion of the thigh link and of the calf link. The exoskeleton is attached to the hip through joints allowing extension and flexion. The energy for moving the exoskeleton is provided by the user thereof. This device can be applied to persons who require aid in walking or who need to be stopped, bearing and carrying loads and weights, i.e., the purpose of the device is to increase the user's ability to bear large weights when he or she is walking or is stopped.

International patent application number PCT/US2006/014227 describes a variant of the previously described device, further incorporating a motor so as to achieve a greater increase in the strength of the person using the exoskeleton.

Unites States patent application number US-2006260620-A1, which includes an anchoring to the hip, is structured to achieve results that are different from those of the present invention. As previously noted, this application is directed to a system for increasing the ability to bear large loads, to rest while standing or to substitute the lack of strength in weak legs. As such, this system is not useful for practicing a sport that is as dynamic and that requires as much flexibility as skiing. Rather, it merely has the purpose of increasing the load capacity, whereas as explained in this specification, the present invention is structured to increase resistance, not strength, against such things as unwanted rotations of a ski and other potentially dangerous movements, as well as increasing ski control.

The system described in United States patent application publication number US-2006260620-A1 is designed to work vertically with movements similar to those carried out while walking, counteracting forces of gravity, but not to resist rotational movements in a horizontal plane, like the invention described herein, which is particularly applicable for snow skiing.

The artificial hip joint described in United States patent application publication number US-2006260620-A1 does not have a mechanism allowing the natural rotation about all the natural axes of the legs and at the same time limiting the potentially injurious angular movement of the legs. On the other hand, the present invention provides a mechanism especially designed to allow all the freedom of movement necessary for such activities as skiing, while preventing unnatural movements that may cause injuries. The present invention is especially useful for protecting against extreme rotations of the foot, being designed to support rotational forces or torques due to the large lever that is attached to the skier's leg, i.e., the ski, which situation does not occur in the application of the device describe in United States patent application publication number US-2006260620-A1.

The artificial knee joint and artificial ankle joint of the device described in United States patent application publication number US-2006260620-A1 do not have any mechanism allowing the natural movements necessary for activity such as skiing, and which at the same time protects the joints against movements or positions of the knee in particular, and the leg in general, that can cause injuries. On the other hand, the present invention does provide these mechanisms in the artificial joints, on one hand to provide all the necessary range of movements and on the other hand to limit or prevent those movements or positions which may be injurious to the leg in general and the knee in particular, especially focusing on the protection against severe rotations of the foot, or of the body around the foot, which may occur involuntarily during physical activities such as skiing.

Additionally, US-2006260620-A1 has no mechanism contributing to greater control of the skis by the skier, whereas in certain aspects of the present invention, a mechanism is provided that is especially designed for the skier to have at all times added control over the skis so that if a ski is in danger of losing the path that the skier wants to follow due to uneven terrain or any other reason, this mechanism would automatically prevent such diversion. The skis will always stay on the path required by the skier regardless of uneven terrain, irregularities in the snow or different snow qualities.

No feature similar to the foregoing is described in US-2006260620-A1, nor can any element thereof be useful in similar circumstances, much less solve this problem considered by the present invention.

A device that solves many problems existing in the state of the art devices as well as other problems is describe and claimed in the co-pending U.S. patent application Ser. No. 12/103,196 titled "Exoskeleton", filed on Apr. 15, 2008, for a new exoskeleton invented by the same inventors of the present invention. This co-pending application no. is incorporated herein in its entirety by reference. The present invention provides additional features and can be used in combination with aspects of the exoskeleton described in the co-pending application.

There are no prior known protective devices offering a minimum assurance of preventing such injuries, allowing in turn the freedom of movements necessary for skiing, or additionally control of the skis while skiing.

SUMMARY OF CERTAIN ASPECTS OF THE INVENTION

By its configuration and components, the invention, safety and control device for snow skiing, particularly downhill skiing, solves problems and inconveniences or disadvantages not solved in the state of the art, mainly due to the fact that such problems had not been set forth and never raised or appreciated until now, due to that the known devices do not prevent the possibility of knee injuries or injuries to other parts of the leg. Rather they reduce the possibility of such injuries in very particular and very determined conditions, that are specific to each device, unlike the present invention which prevents leg and hip injuries, and especially, knee injuries. The device of the present invention diverts the forces that potentially might cause damages (FIG. 1B), generally in the legs and specifically in the knees, to strong parts of the body as the hip and to the more resistant parts of the legs. When the movement arrives to a dangerous anatomical position, the exoskeleton resists the generated forces and diverts them to the stronger parts of the leg and hip. These forces are specially, although not exclusively, the ones produced by the large lever represented by the ski that in another situation would cause serious injuries in the knee.

The present invention also allows the natural control of the skis, without the skier having to generate an action on his or her own to actuate a mechanism simply with his or her natural movements while skiing. The device of the invention allows neutralizing the torsion of the knee by the absorption of the unwanted rotation of the foot by the structure and the supporting of such structure in areas of the body much stronger than the knee.

An object of the present invention as implemented in certain embodiments is to provide an exoskeleton or device preventing injuries to a skier while at the same time allowing the skier to control the skis and prevent unwanted movements thereof. In particular, the present invention as implemented in certain embodiments prevents injuries due to torsion, and other transverse, longitudinal forces, etc. of the knees, the legs in general and, in several of the preferred embodiments, the hips while skiing, by means of diverting the stress through the exoskeleton or device, and particularly by diverting the excessive torsional stress that may result in injuries caused by the skis through a support structure or exoskeleton formed by the device and attached to strong areas of the legs and, in several of the preferred embodiments, to the waist, thus assuring that the knee in particular will not be subjected to this stress. The device according to several embodiments of the present invention can also allow the prevention of movements of the skis that are not wanted by the skier.

These objects are achieved in several embodiments of the present invention by providing a device that transmits a significant part of the torsion or torque and other potentially injurious forces caused while skiing from the rigid boot, the binding, or the ski itself, to strong areas of the body through the structure of the safety device, thus freeing the ligaments of the knee in particular, and the areas of the leg or hips in general, from the overload caused by the lever (the ski), as well as providing in the device members that detect and block unwanted movements of the skis.

In certain embodiments, the device or exoskeleton of the present invention includes the following components:

a first support member that couples the exoskeleton to the user's body above the knee, such as the hips or waist or the thigh;

a second support member that couples the exoskeleton to the to the user's body below the knee, such as to the skier's boot, the bindings of the boot to the ski, or the ski itself;

a first linkage or linkage assembly with two ends, an upper end coupled to the first support member and a lower end coupled to the second support member, the linkage assembly extending along the leg of the person or skier wearing the exoskeleton;

at least one clutch mechanism, operatively coupled between two elements of the exoskeleton, allowing the clutching or unclutching of the two elements of the exoskeleton, preferably arranged along the linkage assembly, and which upon receiving a slight action (force, moment, movement, or the like) clutches or unclutches both parts of the exoskeleton; and at least one sensor that can detect movements of the foot and transmit a corresponding action or signal to the clutch mechanism.

The above mentioned clutch mechanism refers to a mechanism that connects and disconnects two parts in which the exoskeleton can be divided.

The clutch mechanism and the sensor, depending on their configuration, can have, for example, two different options with two working ways each:

A first option as default in which the corresponding two parts or elements of the exoskeleton are unclutched or not coupled when the mechanism receives no action or signal from the sensor, The clutch mechanism in this option can work in two different ways:

When an action or signal is received from a sensor it blocks the rotation in only one specific direction, leaving the opposite rotating direction free.

When an action or signal is received from a sensor it does not block, allowing the rotation in both directions. In this way the control system is deactivated or disconnected but the protection is maintained through the security system.

A second option where the clutch mechanism maintains as default the two parts or elements of the exoskeleton clutched or coupled when the mechanism receives no action or signal from the sensor.

The clutch mechanism in this option can work in two different ways:

When an action or signal is received from a sensor it allows the rotation in only one specific direction, leaving the opposite rotating direction blocked.

When an action or signal is received from a sensor it does not free the mechanism. The exoskeleton is coupled all time.

The clutch mechanism can also, depending its configuration, make the clutching or coupling between both parts of the exoskeleton progressive or instantaneous.

The following explanation device refers to a device that works in one of the previously defined working ways, specifically the preferred state in which the exoskeleton is unclutched by default, and it clutches only in the "unwanted" or not desired sense of turning.

Therefore, the exoskeleton of the invention is preferably made up of a structure that is attached to parts of resistant material, located around the waist and/or the legs. The structure, extending from the waist or legs to the skier's boots, bindings or skis, is made up of support elements and a linkage assembly formed by rigid members and/or jointed members, which can be shafts or elongated members parallel to the leg and anatomical parts embracing the same, such that it allows the transmission of the torsion torque generated in the foot due to the force of the ski, as well as other longitudinal and transverse forces that may cause injuries to the actual structure and subsequently to the more resistant areas of the legs and, in most of the preferred embodiments, to the waist. These members or parts making up the linkage assembly of the structure or exoskeleton can be standard or customized or extendible, and they can be made of fiber, plastic or any materials available in industry today or any materials that may be used for this purpose in the future.

The first support member is preferably located at the height of the waist where relative torsion between both feet, that are connected by the exoskeleton through the hip, is further limited, although it is possible to use a first support member in each leg or only in one of the legs, such that such first member can also be located in the skier's thigh or thighs.

The exoskeleton can have joints or mechanisms between two elements of the same such that they can transmit torque between those two elements, allowing the torque transmission independently of the angular alignment between the respective torque axis of both elements. Examples of these joints or mechanisms include certain elastic joints or universal joint-type transmissions, cables of the type employed in odometers, among others.

The clutch mechanism, incorporating the brake mechanism, is preferably arranged along the linkage assembly and, upon applying a slight action (force, moment, movement, or the like) on the mentioned mechanism, generates a high resistant torque, and receives this action from a sensing device that can detect movements, preferably of the foot, in order to transmit them to the clutch mechanism. The mentioned mechanism, or occasionally mechanisms, can be located along the linkage assembly, which allows coupling (clutching) or decoupling (declutching) the structure or exoskeleton to/from the skier's boot, binding or ski itself, and/or to the waist. The clutch mechanism can also be placed at one end of the linkage assembly and coupled to one of the support members of the exoskeleton.

The mentioned sensor is preferably formed by a mechanism that can detect the direction in which the foot wants to rotate or move in relation to the ski, the mechanism being able to be housed between the inner booty of the boot and the rigid outer boot, on the outside of the boot, at the tip, the heel or in any other place, provided that it can pick up the input information into which the movement of the foot is converted. This mechanism will essentially be formed by what will be referred to hereinafter as "sensors", and sensors could be used to detect (through mechanical, hydraulic, electrical or other components, or a combination thereof) forces, angles, movements or any other relevant information in any area of the feet, legs or hips.

The sensors can be located between the boot and the brake or clutch mechanism or between the boot and the booty, outside the boot, in contact with the binding of the ski or in any other place allowing them to pick up the necessary information relating to the forces exerted by the skier's body. These sensors can be mechanical, hydraulic, pneumatic, or electronic, and they can be connected to the remaining brake or clutch mechanisms in any of these or other manners that allow transmitting the information.

The processing of the information picked up by the sensors will differ depending on the location of the sensor mechanisms. For example:

1) If the sensors are located between the boot and the binding of the boot to the ski, the pressure that the sensors receive, and therefore the information that they transmit, will be the pressure exerted by the ski on the assembly of the boot and the exoskeleton. In order for the system to operate correctly, it is necessary to isolate the resistance exerted by the foot, through which the skier's intentions are manifested, from the resistance exerted by the exoskeleton. One alternative for obtaining this isolation is, as detailed in the preferred embodiment, to use an additional member and place it between the boot and the binding, such that it is attached to the boot with a certain allowance and in turn connected to the exoskeleton through the clutch mechanisms. If the sensors are located between the boot and this part, these sensors directly measure the resistance opposed by the boot to the ski, regardless of the resistance exerted by the exoskeleton.

2) If the sensors are located between the boot and the inner booty, i.e. inside the boot, they also measure the resistance opposed by the foot to the ski, regardless of the resistance exerted by the exoskeleton.

3) If the sensors take flexion of the knee as data in one of the embodiments, the clutches could be acted on depending on this flexion.

It is possible to combine the previous members and mechanisms between different joints and positions in the structure of the device.

At any point while skiing in which one or both skis, due to irregularities in the snow or any other circumstance, runs the risk of losing the path wanted by the skier or if a leg gets close to a position endangering its safety, tension occurs in the leg that activates the sensors, sending information or force to the clutch mechanism and causing the coupling of the exoskeleton structure, or linkage assemblies, to the boots and first support member arranged at the skier's waist or hips, and in some preferred forms at the thigh, as well as to the more resistant areas of the legs, thereby protecting the weaker areas such as the knees, among others.

The resistance of a skier's legs is thus significantly increased, so instead of having the weakest link at the knee, there is a chain of strong links allowing the skier to ski with more energy and at the same time with more confidence, certain that his or her knees are not going to be subjected to stress that may injure them.

The present invention can in turn allow skiing with tighter binding settings, with greater safety and no risk of injuries. As a last resort, if the extreme case in which the binding must be released is reached, it will always do so under the load of this structure and not the joint of the knee.

The possibility of an optimal setting of the bindings, mentioned above, is extremely important. In the current state of the art, the existing bindings force the skier to choose between a "loose" setting or a "tight" setting, it being very difficult to achieve the optimal one. A setting that is too loose will make the skier lose a ski in an inconvenient situation, which could cause injury. A setting that is too tight entails the risk of the skier's leg suffering serious injuries because the binding does not release the ski before reaching the injury point, and what is worse is that even with "loose" settings it is by no means ensured that the bindings will be released in certain situations.

With a device according to certain embodiments of present invention, the skier can tighten the bindings as much as he or she would like, depending on the skier's level and on the difficulties the skier wants to take on (even extreme skiing) in order to be certain that the ski will not be lost and without running into any risk of injury.

With the device according to certain embodiments of the present invention, the result for the skier may be similar to what happens when driving a modern car in which the action of braking or turning the wheels requires just a small force by the driver to exert much greater forces on the wheels. This differs in the case of the present invention, however, in that the present mechanism does not increase the force, but rather the resistance, and it does not require additional energy other than the energy generated by the actual action of skiing.

The operation of the exoskeleton upon skiing is reflected in that if one or both skis starts to rotate, open, close or make any other movement that the skier does not want, pressure is automatically produced in the sensor on the side opposite to the side towards which the ski is trying to move, which in turn causes the "clutch" or coupling of the clutch mechanism with the shaft of the structure or linkage assembly of the exoskeleton.

In this case, the clutch mechanism or mechanisms are responsible for part of the torsion torque generated by the ski being diverted to the structure (exoskeleton, strong areas of the leg, thigh, waist and/or hips), such that given the demand of the torque exerted by the ski, the skier's leg does not have to oppose an equivalent torque, but rather a fraction thereof, that which would be naturally exerted if the skier did not have a lever the size of the ski attached to his or her foot.

Therefore two effects exist, namely:

A multiplying effect of the resistance of the leg given unwanted rotation demands, which translates into a large increase of the control capacity of the ski, and A diversion to the structure or linkage assembly of the exoskeleton, strong areas of the legs, thigh, waist (in most of the preferred embodiments) and, in most of the preferred embodiments to the other ski (insofar as it is connected to the former throughout the entire structure), but not to the knee, of part of the torsion torque exerted on the foot due to the lever effect of the ski, or any other unwanted and/or potentially injurious force. In practice, this translates into a much more resistant structure, with the implications that have already been explained for skiing and the safety while skiing.

Therefore, further objects that the present invention provides in certain embodiments include:

Preventing knee in particular and leg and, in most of the preferred embodiments, hip injuries.

The skier having greater control over the skis,

The possibility for the skier to tightly adjust the bindings without being afraid of being injured, and Greater freedom of movements while skiing, since there are no limits to the movement at all times other than those that the skier wants and transmits through his or her feet.

The safety device for preventing knee injuries thus further allows control over the skis in all situations, making the skiing experience more satisfactory as it eliminates all the unwanted movements of the skis as a result of irregularities in the snow, or other elements. As mentioned, the skier perceives the reactions of the ski in a natural manner; there are no limits to the movements he or she wants to make nor are there any forces greater than those that his or her body is used to feeling. The skier will simply feel that by applying the resistance that he or she would naturally apply to prevent an external agent from moving his or her foot, the foot resists any force generated by the lever of the ski as if this lever did not exist.

As mentioned at the beginning of this description, the probability of suffering a serious knee injury is very high today and the costs in money and suffering for this injury is also very high. The injuries affect both beginners and experts. They often occur even when one is not skiing, while waiting in line for the mechanical ski lifts, when a person tries to get up, or in an unexpected circumstance. Any of these events is covered and protected by the present invention.

Finally, the foregoing results in another concept of safety, active safety, insofar as the device not only protects the joint when an accident occurs (passive safety), but it also contributes to preventing accidents (active safety) since it allows controlling the skis, thus reducing the number of injuries not only in the knees, legs and, in most of the preferred embodiments, hips, but also in other parts of the body.

BRIEF DESCRIPTION OF THE DRAWINGS

For the purpose of aiding to better understand the invention, the following figures attached to this description in a non-limiting manner shall be described below:

FIG. 1A shows a skier without an exoskeleton of the present invention and includes a schematic depiction of certain stresses that the skier is subjected to;

FIG. 3 shows a first support member for the hip/waist and elements for joining to the linkage assembly;

FIG. 4 shows certain details of a rigid belt for the first support member of FIG. 3;

FIG. 9 shows the T element of the rigid belt in FIG. 3 with a double hinge joint and a length regulating mechanism (LRM);

FIG. 10 shows the outer member of the LRM;

FIG. 26 shows a perspective view of third embodiment of clutch mechanism, specifically a gear train clutch mechanism;

FIG. 27 shows a different perspective view of the mechanism in FIG. 26;

FIG. 32 shows a top view and section of the main element of the mechanism of FIG. 31;

DESCRIPTION OF EXEMPLARY NON-LIMITING EMBODIMENTS OF THE INVENTION

Figure 1A:
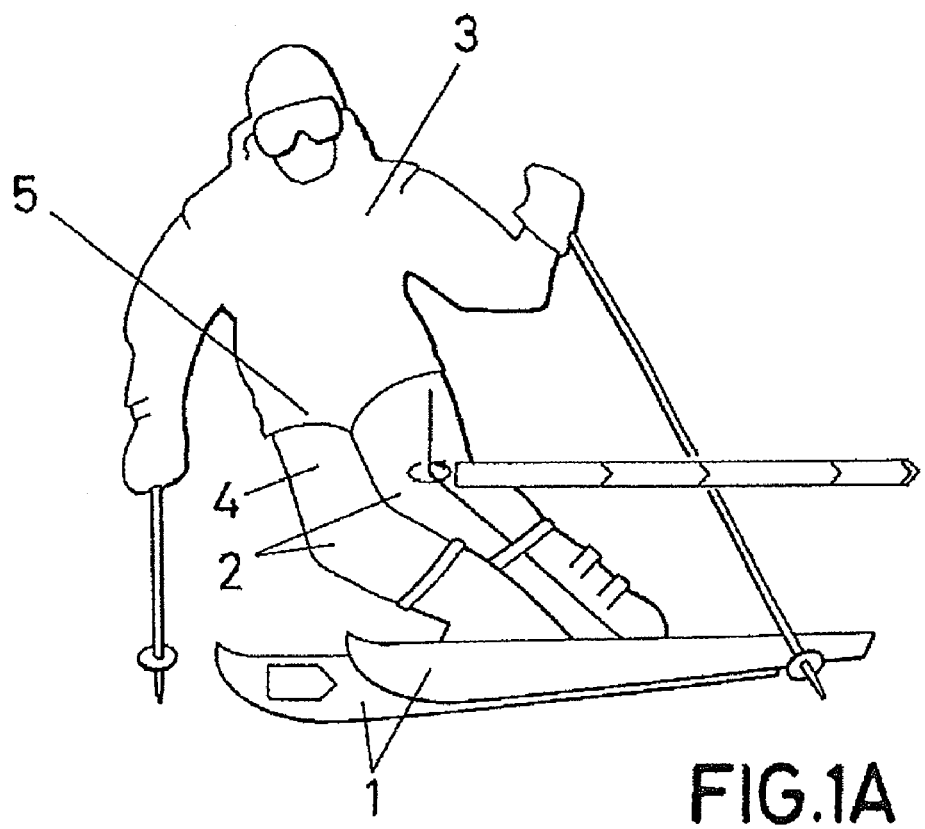
Figure 1B:
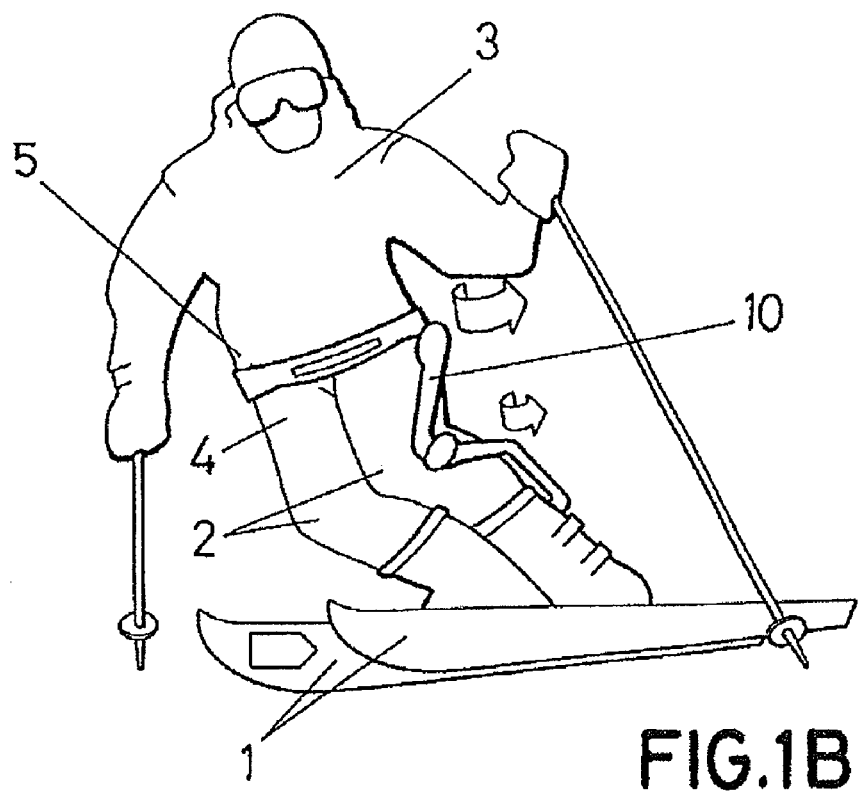
FIG. 1B shows a skier with an exoskeleton of the present invention and a schematic depiction of the resulting stresses.

Different preferred embodiments of the invention for use in snow skiing will be described next. In relation to FIGS. 2, 2B, 28, 29, 30, 37 and 38, the exoskeleton or safety and control device for snow skiing is to be worn by a person (3) over at least one leg and includes a first support member (20, 21), preferably rigid, a second support member (30, 31), a linkage assembly (40) between the first support member and the second support member, at least one clutch mechanism (300, 400, 600, 700) to generate a resistant torque upon receiving a minor force. The clutch mechanism incorporates a brake mechanism (150, 170) and is operatively coupled between two parts or components of the exoskeleton. The clutch mechanism (300, 400, 600, 700) is arranged along the linkage assembly (40), the clutch mechanism being in contact with a sensing device (140) that detects the movements of the skier's foot and transmits them to the clutch mechanism (300, 400, 600, 700), such that the linkage assembly enables the transmission of the torque from the second support member to the first support member and allows the natural movements of the skier, as well as control of the skis, since a significant part of the torque generated on the second support member due to the lever effect of the ski is diverted to the first support member.

The linkage assembly (40) located between the first and second support members can be split into two subassemblies (41, 44), between the support members, such that the first linkage subassembly (41) is an upper linkage assembly (41) that connects a point above the knee (2) (e.g., the first support member (21) attached to the hip (5) or the first support member (29) attached to the thigh (4)), to the artificial joint at the height of the knee (2), and the second linkage subassembly (44) is a lower linkage assembly (44) that connects the artificial joint at the height of the knee (2), (e.g., the hinge (52)) to the second support member.

The linkage assembly (40) can be located in one or in both of the legs of the skier or person using the exoskeleton.

In one preferred embodiment (10) of the exoskeleton or safety and control device for snow skiing in accordance with the present invention, shown in FIGS. 2 to 21, there is provided a structure attached to the body by a first support member (21) coupled to the person's body above the knee (2), specifically a first ergonomic rigid coupling part (21) such as the one shown in FIGS. 3 to 8, located approximately at the height of the waist or hips (5) of the skier or user.

If such a first rigid support member (21) is provided, it can take the form of a rigid belt (21) having two parts (22, 23) linked together to form a rigid whole, thus allowing its opening for coupling to the skier's body along its entire contour, since it surrounds the waist with the belt surrounding part (22) and a belt front part (23). The belt can be clamped by the user at the front with the help of belt connections (24, 25) and a belt closure (26). One of the belt connections (24) is placed on a free end of the belt surrounding part (22) and the other belt connection (25) is placed on the free end of the belt front part (23). The belt connections (24, 25) are partly coupled together, one on top of the other forming one element and the belt closure (26) fixes both belt connections (24, 25) together.

The first support member, in this embodiment the belt (21), is connected to the rest of the exoskeleton through a T element (27) that is secured to the belt surrounding part (22) by screws (28). This T element can also be included as part of the belt surrounding part (22).

The remaining components forming the exoskeleton structure can be arranged on both sides of this first support member or rigid belt (21). The lower end of the T element (27) is coupled to the linkage assembly (40), specifically to the upper end of the linkage assembly (41), and more specifically in this embodiment to the upper end (42) of the upper linkage assembly (41) through an artificial joint, specifically a double hinge (53) with pins (54).

This double hinge (53) is preferably made up in such a way that limits, in an adjustable way, the rotation range in each of the two directions of each of its two axis.

The upper linkage assemblies (41) can have a length approximating the length of the femur of an average man and can preferably arrange means that allow modifying its length to provide an optimum fit using for this purpose a length regulating mechanism or LRM (60) coupled to the artificial joint, in this case a double hinge joint (53), preferably of limited range.

The LRM (60), as shown in FIGS. 9 to 13, is used for regulating the length of the upper linkage assembly (41), or the lower linkage assembly (44), and includes a LRM inner member (61) or shaft, with hexagonal section, coupled to the upper end of the upper linkage assembly (42) and a LRM outer member (62) or hub, with hexagonal section too, coupled to the artificial joint or double hinge (53) attached to the T element (27). The LRM inner member (61) has holes or the like (63) in outside facing surfaces and the outer member (62) has at least one sphere (64), preferably two, on its lower end. This outer member (62) also has a pressing device (65) inside for pushing the sphere(s) (64) which is maintained in its place by an LRM outer member cover (66). When the sphere (64) is introduced in a hole (63) of the inner member (61) and the pressing device (65) is not pushed, the coupling between the belt (21), through the T element (27) and the artificial double hinge joint (53), and the upper linkage assembly (41) is fixed. In order to modify the length of the linkage assembly (41) and therefore the length of the exoskeleton, the user must press the pressing device (65) to unblock the sphere (64) from the housing (63) and allow the inner member (61) to move along the outer member (62). The movement can be stopped when the sphere (64) is positioned into the wanted hole (63) of the inner member (61) when the length wanted by the user has been reached. This LRM can also be used to uncouple the upper linkage assembly (41) from the set formed by the belt (21), the T element (27) and the artificial double hinge joint (53).

The exoskeleton can also have coupling systems (60), that are the same as the described LRM or length regulation mechanism, as illustrated in FIGS. 9 to 13, allowing the connection and disconnection between two members or components of the device for the purpose of aiding the assembly or disassembly of the exoskeleton, as well as its use or arrangement on the skier or user thereof. The number of coupling systems (60) as well as the features of each of them can vary, the coupling systems (60) being able to be located at any point along the transmission chain forming the exoskeleton for the purpose of aiding in removing or releasing the exoskeleton. The coupling systems (60) are preferably located in the lower linkage assembly (44) between the second support member and the knee, since the exoskeleton can thus be disconnected from the second support member, for example, the boots (31) or the skis (1) or the bindings of the boot (31) to the ski (1). The coupling systems (60) are preferably quick coupling systems and can also be used for extending the length of the upper or lower linkage assembly, and therefore of the exoskeleton. The previously described LRM for extending the length of the linkage assemblies can therefore also be used as a coupling mechanism (60).

Figure 2:
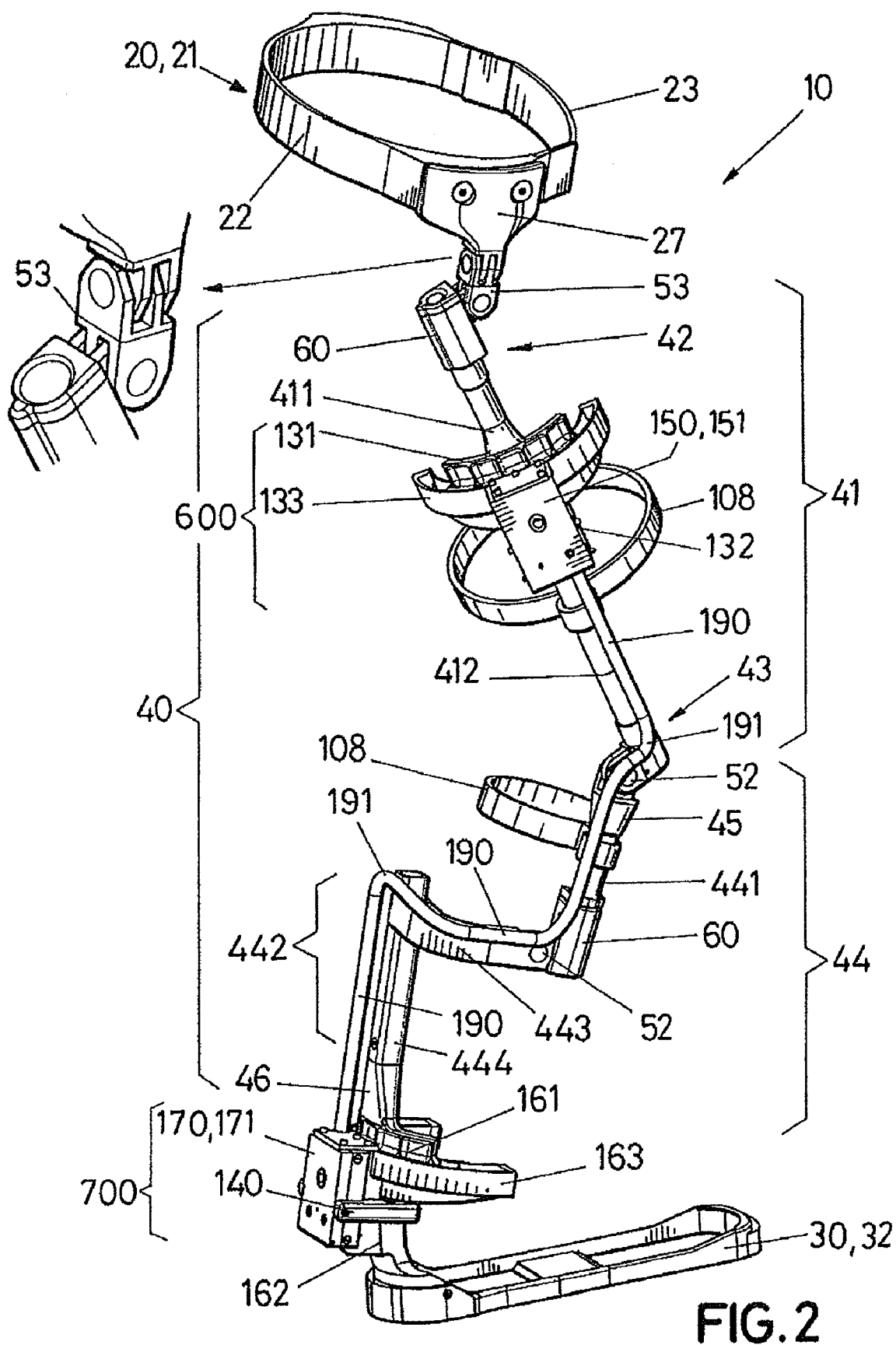
FIG. 2 shows a first preferred embodiment only showing one leg, of the two preferred, of an exoskeleton according to the invention.

As shown in FIG. 2, the upper linkage assembly (41) runs between the hip (5) and the knee (2). The coupling between both members, hip part or T element (27) and upper linkage assembly, is carried out as previously stated, by a joint, preferably a double hinge joint (53) as described, and which can also be a hinge (52), a universal joint or Cardan joint (51) or any other element having similar dynamic features and allowing the angular movements of the leg at the coxofemoral joint at least in the two transverse and sagittal axes, or in other words, allowing flexion, extension, adduction and abduction, while at the same time limiting, preferably in a manner that can be adjusted by the user, the angular movements, i.e. the flexion, extension, adduction and abduction, in said transverse and sagittal axes at values that may by injurious. As already mentioned, the artificial joint placed at the height of the hip is in this preferred embodiment, a double hinge (53) with limited rotation.

Figure 2B:
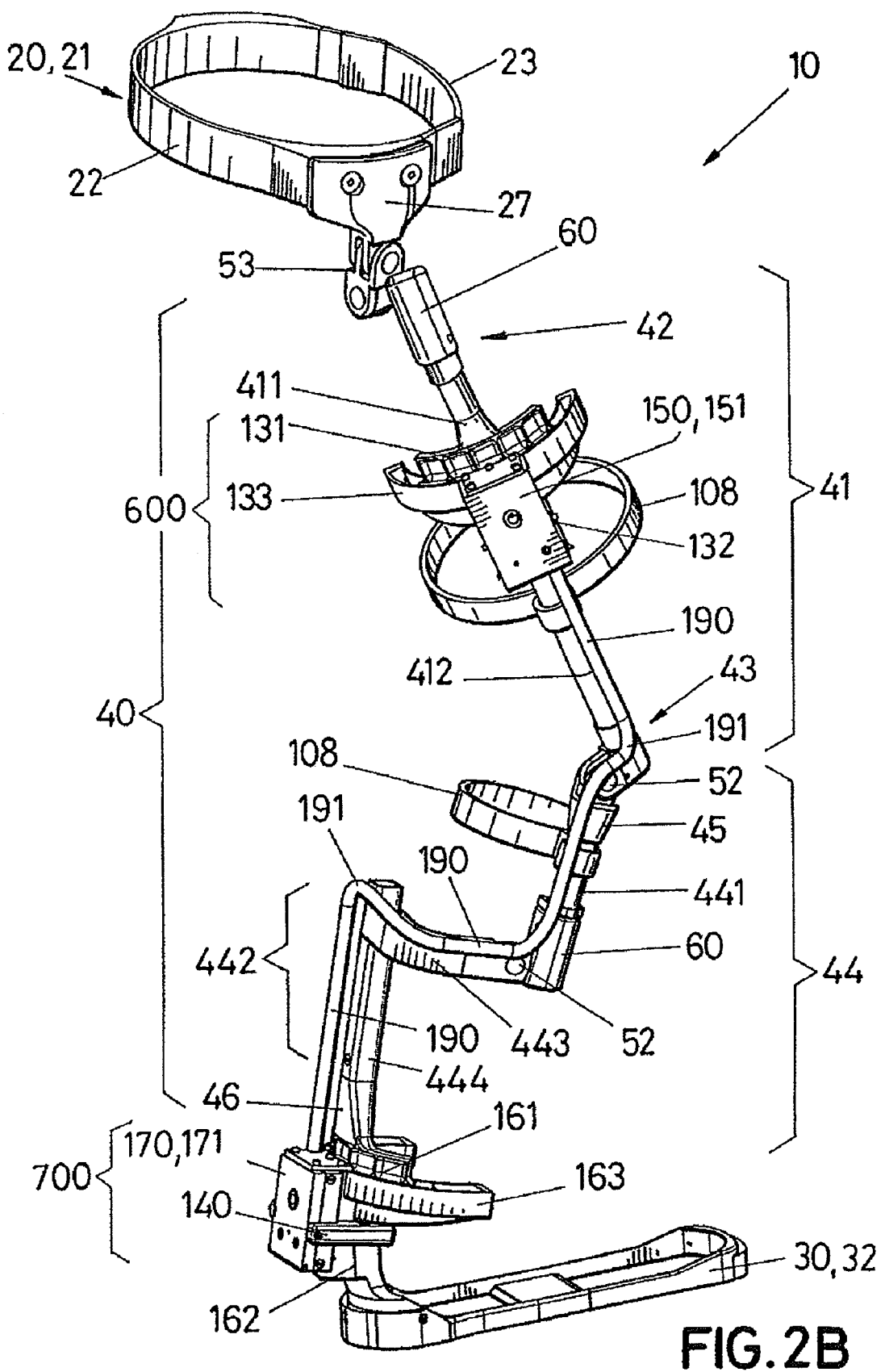
FIG. 2B shows a first embodiment of an exoskeleton as the one shown in FIG. 2, where the double hinge placed at the height of the hip has its two axis turned 90 degrees.
Figure 5:
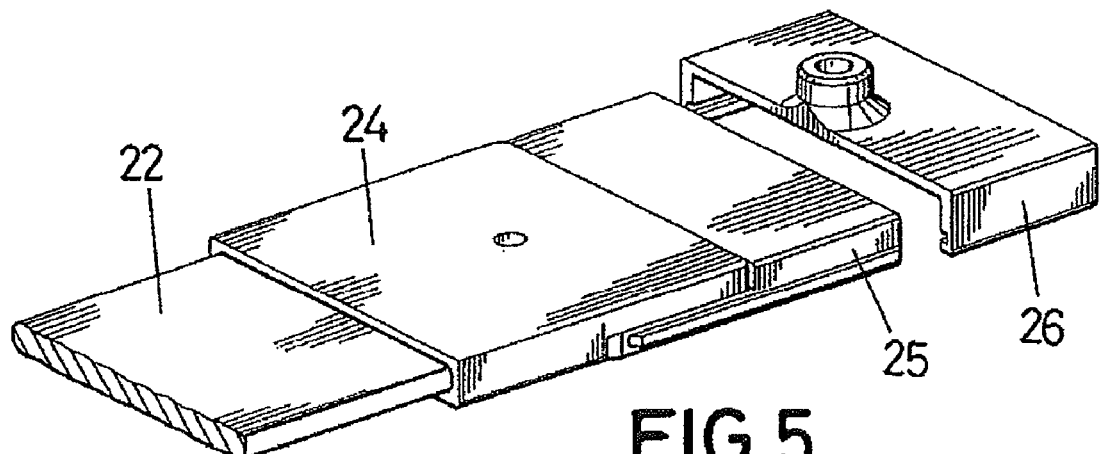
FIG. 5 shows a detail of the connection elements of the rigid belt in FIG. 4 in a stage prior to the connection.
Figure 6:
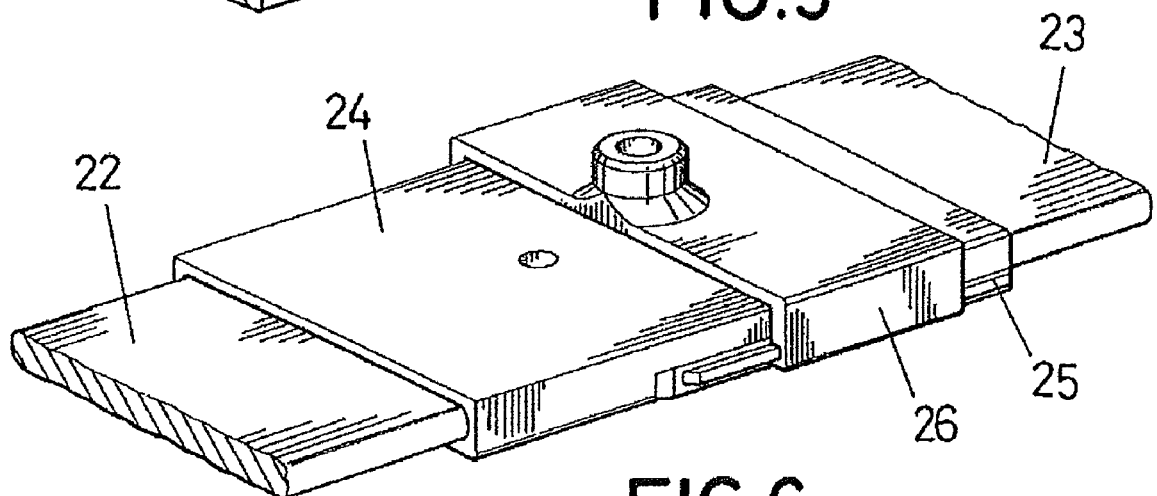
FIG. 6 shows a detail of the connection elements of the rigid belt in FIG. 4 in a further stage prior to the connection.
Figure 7:
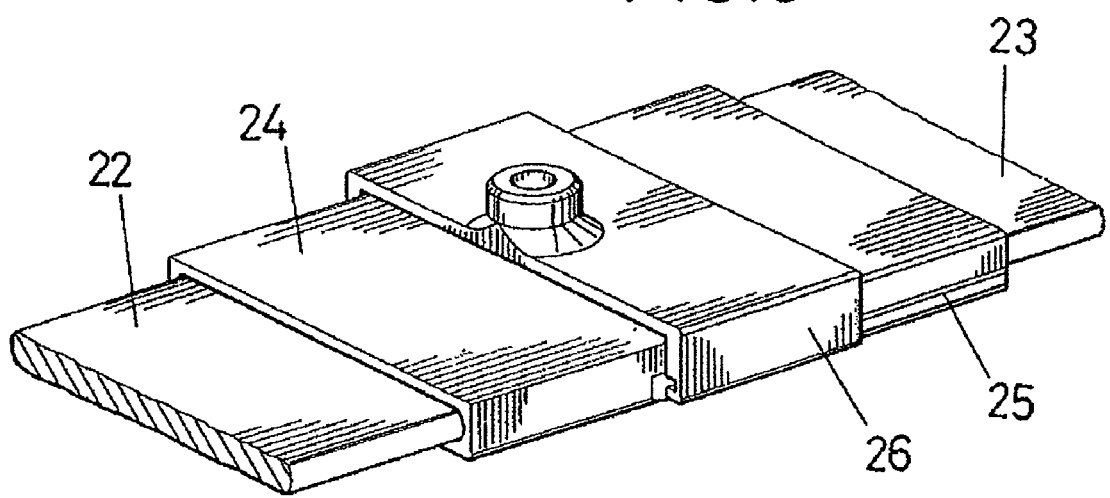
FIG. 7 shows a detail of the connection elements of the rigid belt in FIG. 4 once connected.
Figure 8:
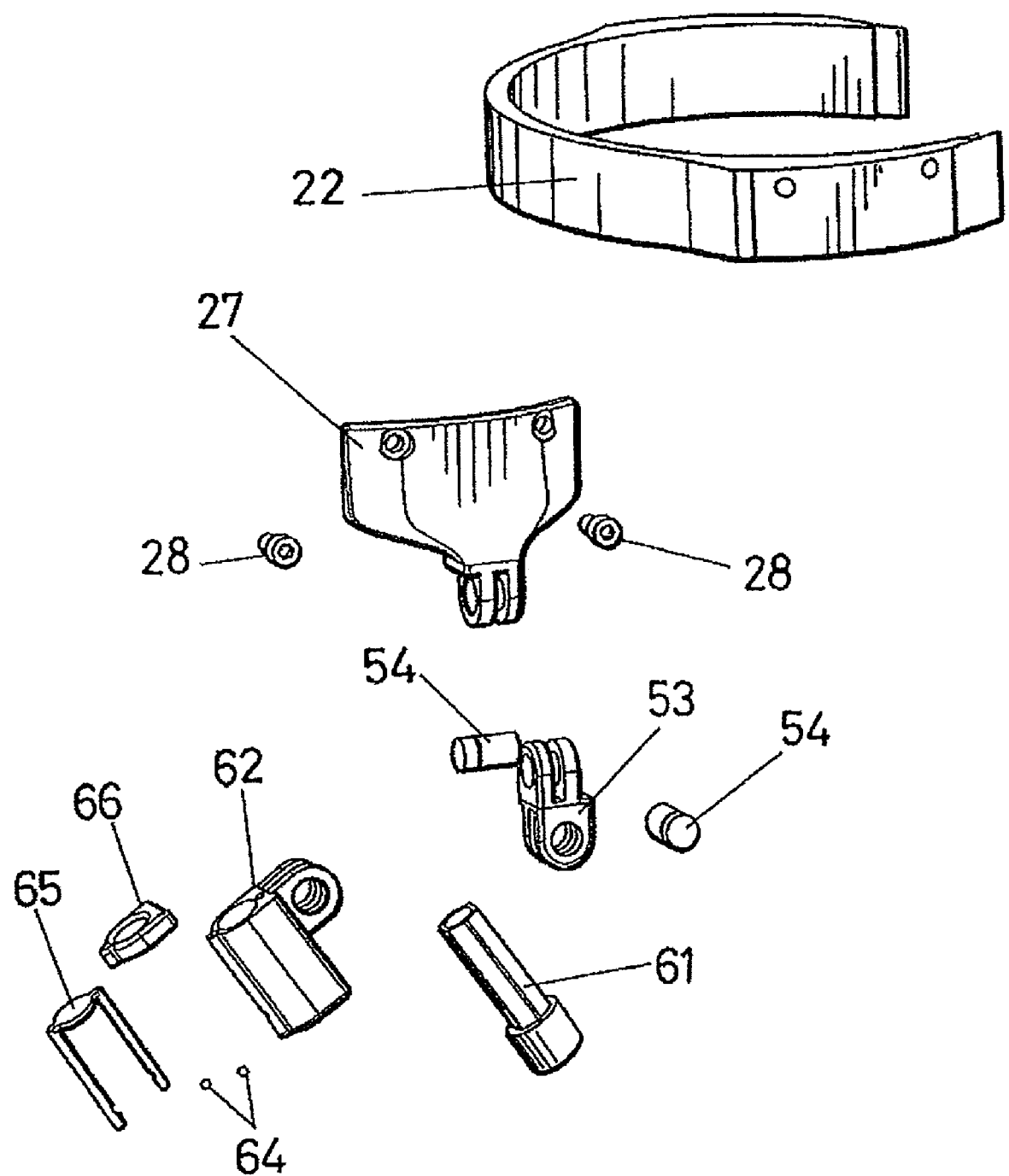
FIG. 8 shows an exploded view of the elements of FIG. 3.
Figure 11:
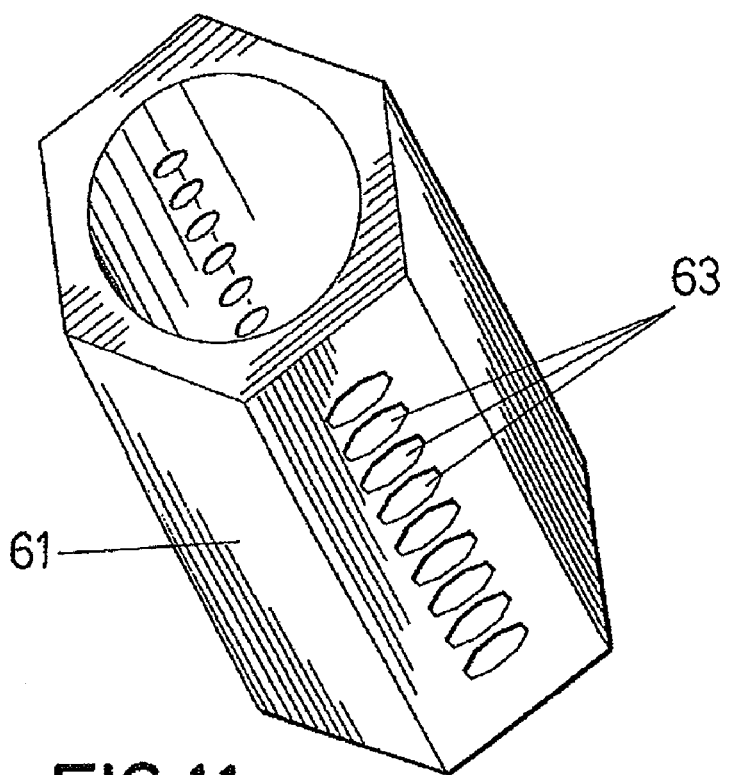
FIG. 11 shows the inner member of the LRM.
Figure 12:
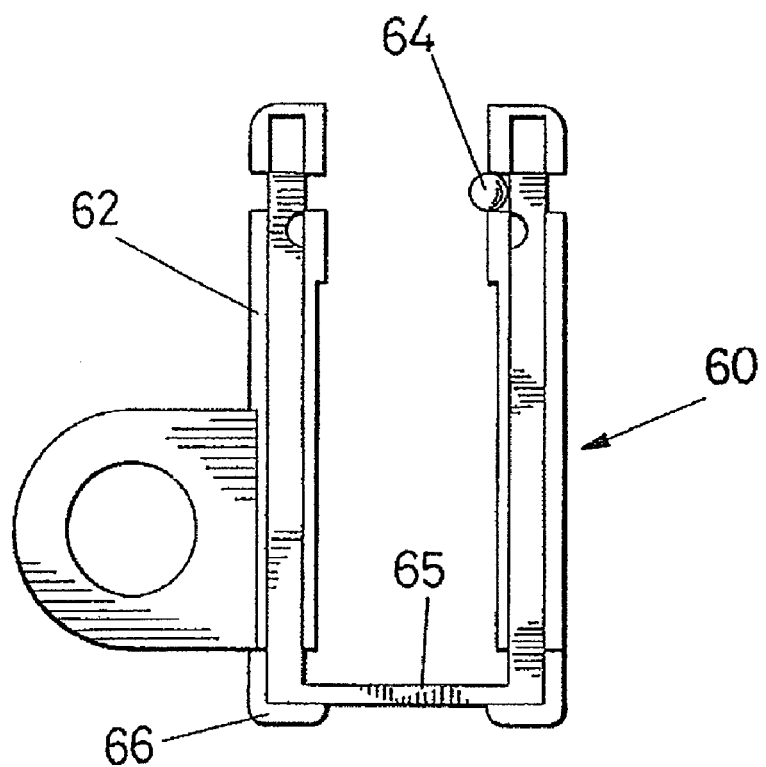
FIG. 12 shows a section view of the LRM.
Figure 13:
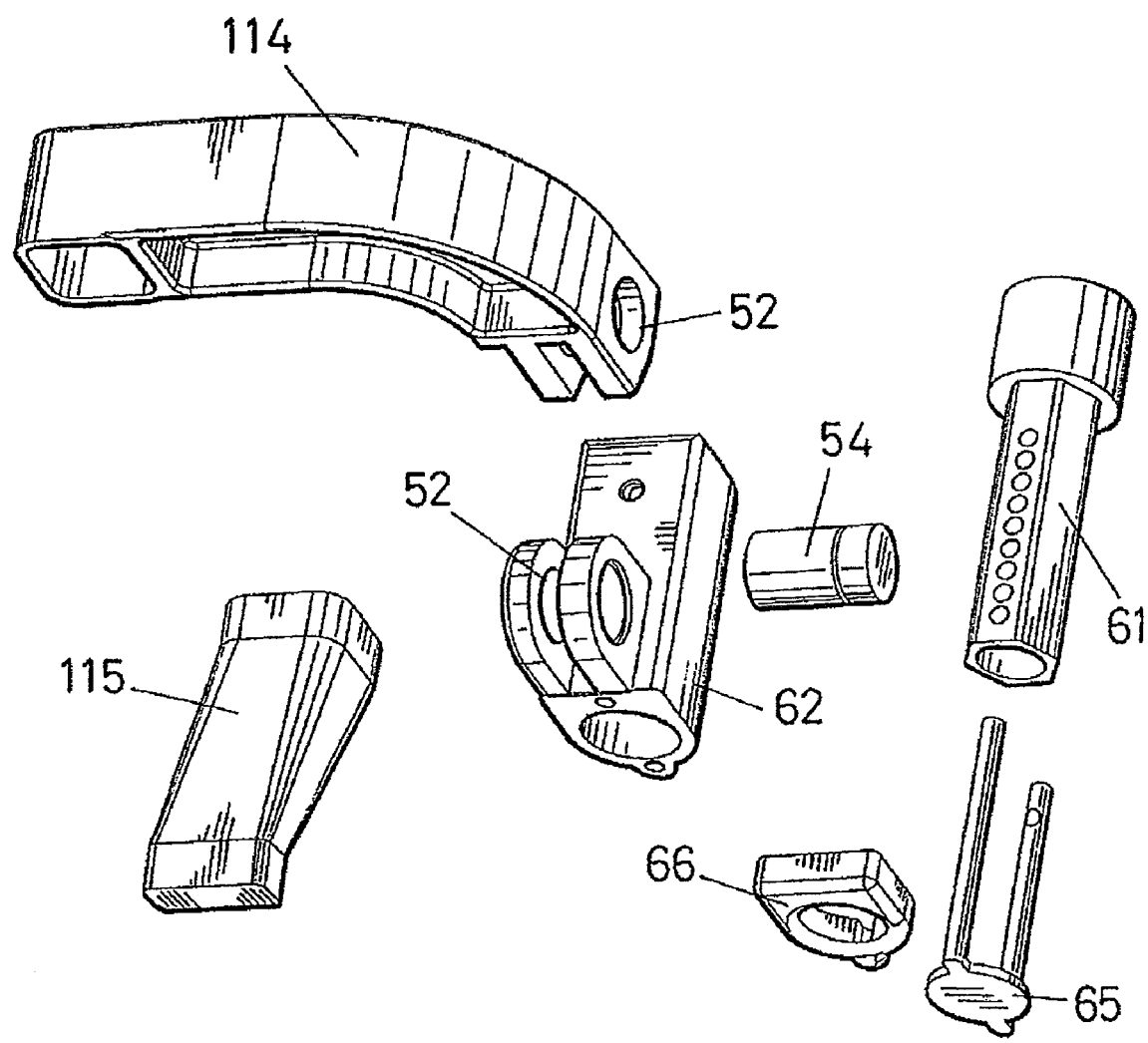
FIG. 13 shows an exploded view of the lower part of the lower linkage assembly linked to a length regulating mechanism
Figure 14:
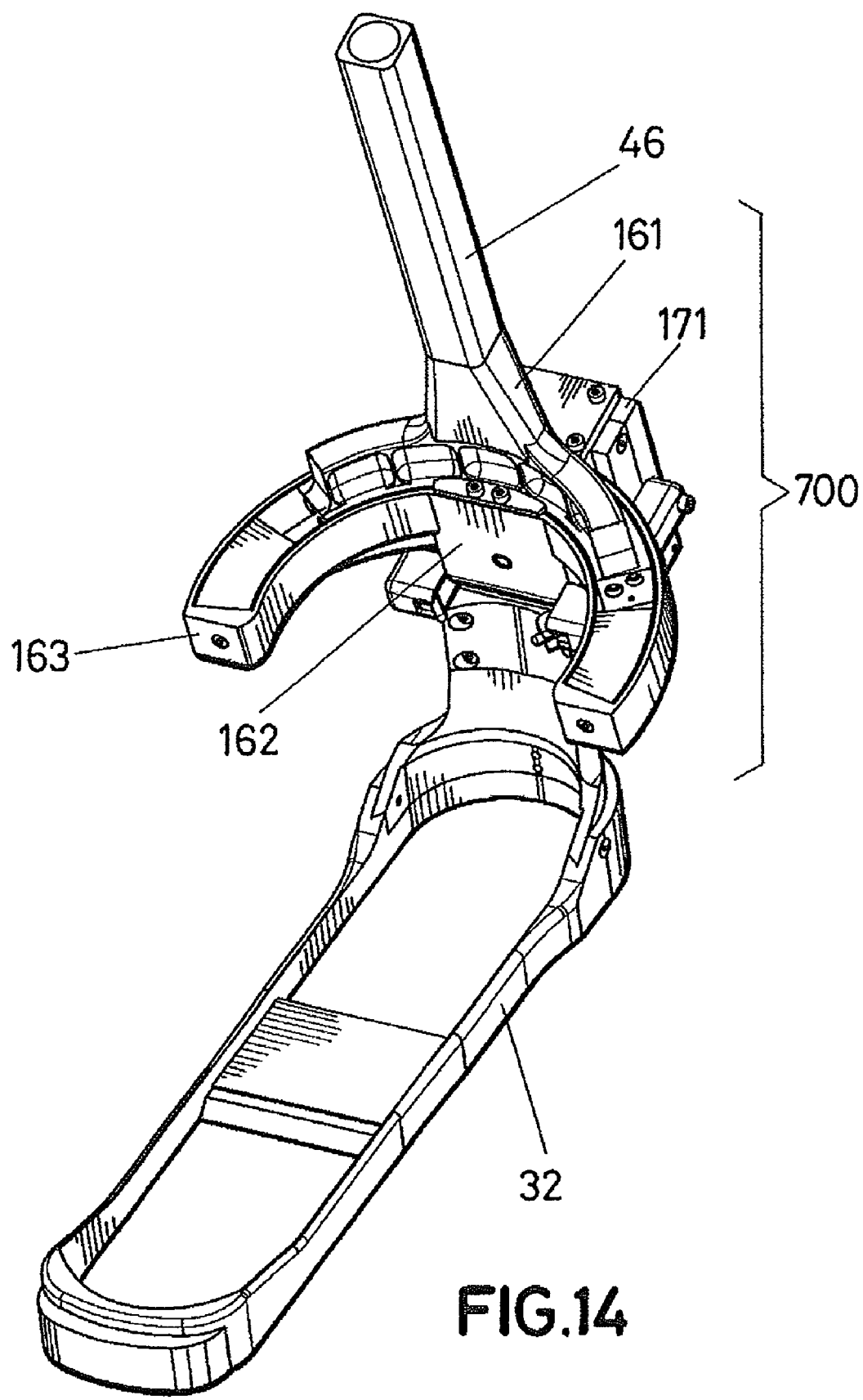
FIG. 14 shows a front perspective view of the second or lower clutch device of FIG. 2.
Figure 15:
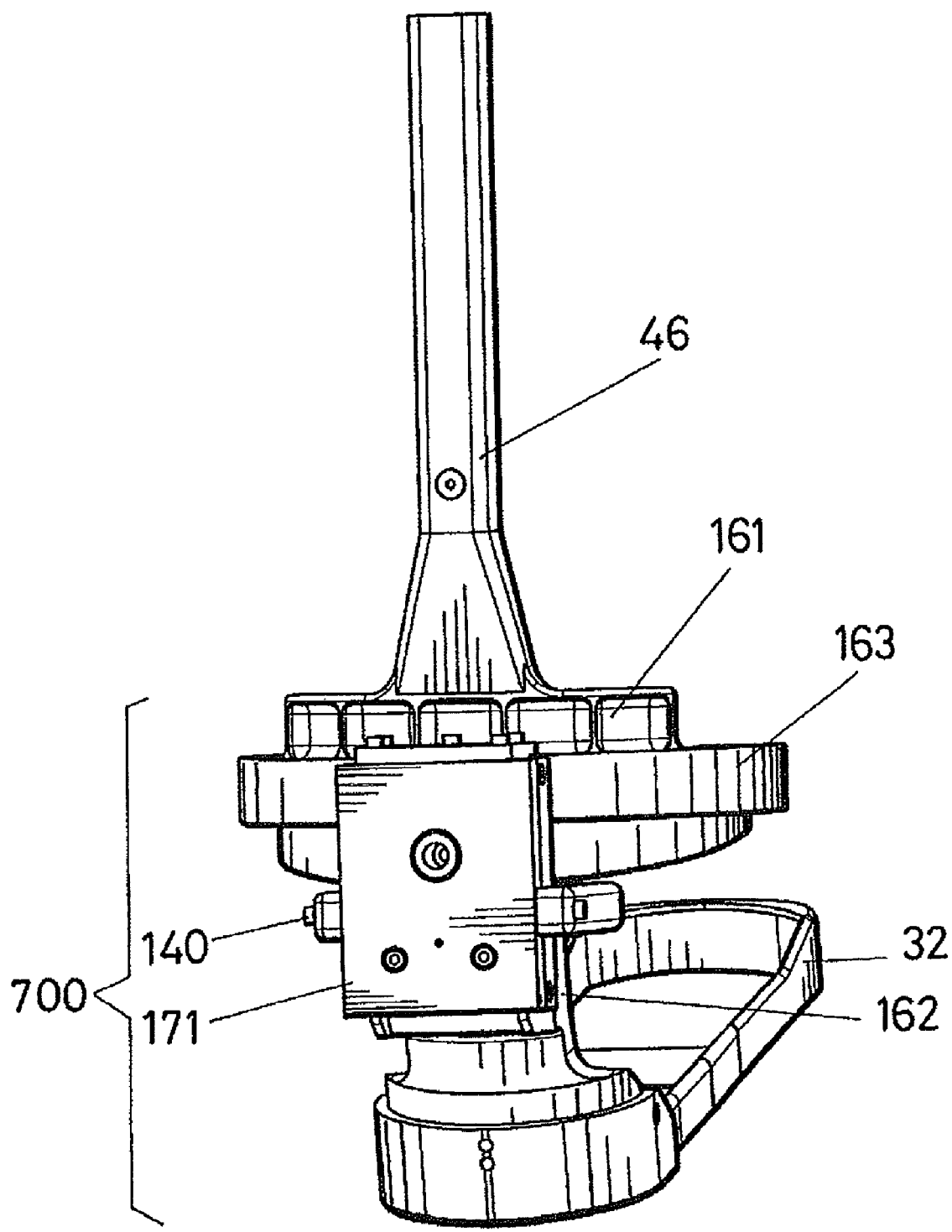
FIG. 15 shows a front perspective view of the clutch device of FIG. 14.
Figure 16:
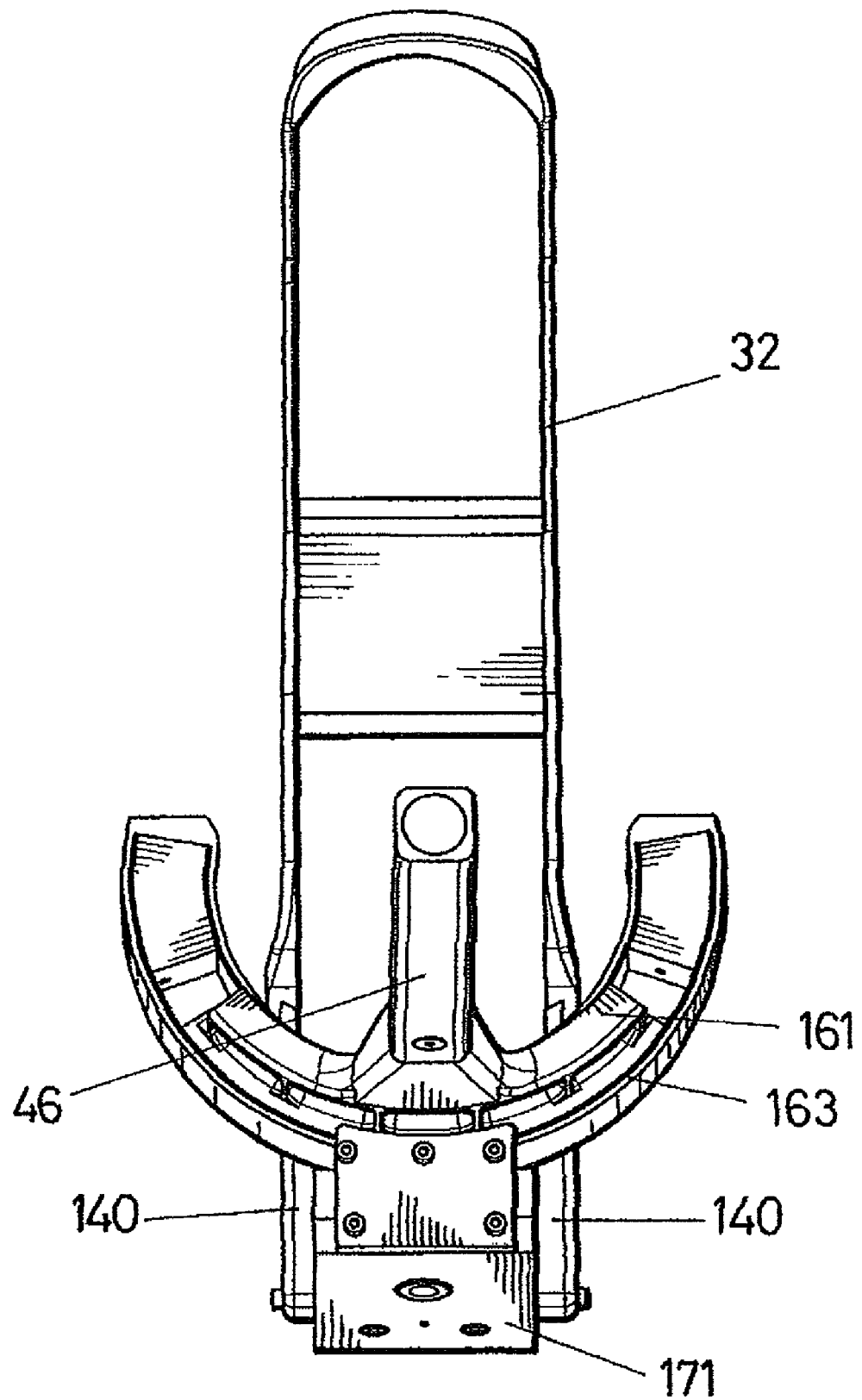
FIG. 16 shows a top view of the clutch device of FIG. 14.
Figure 17:
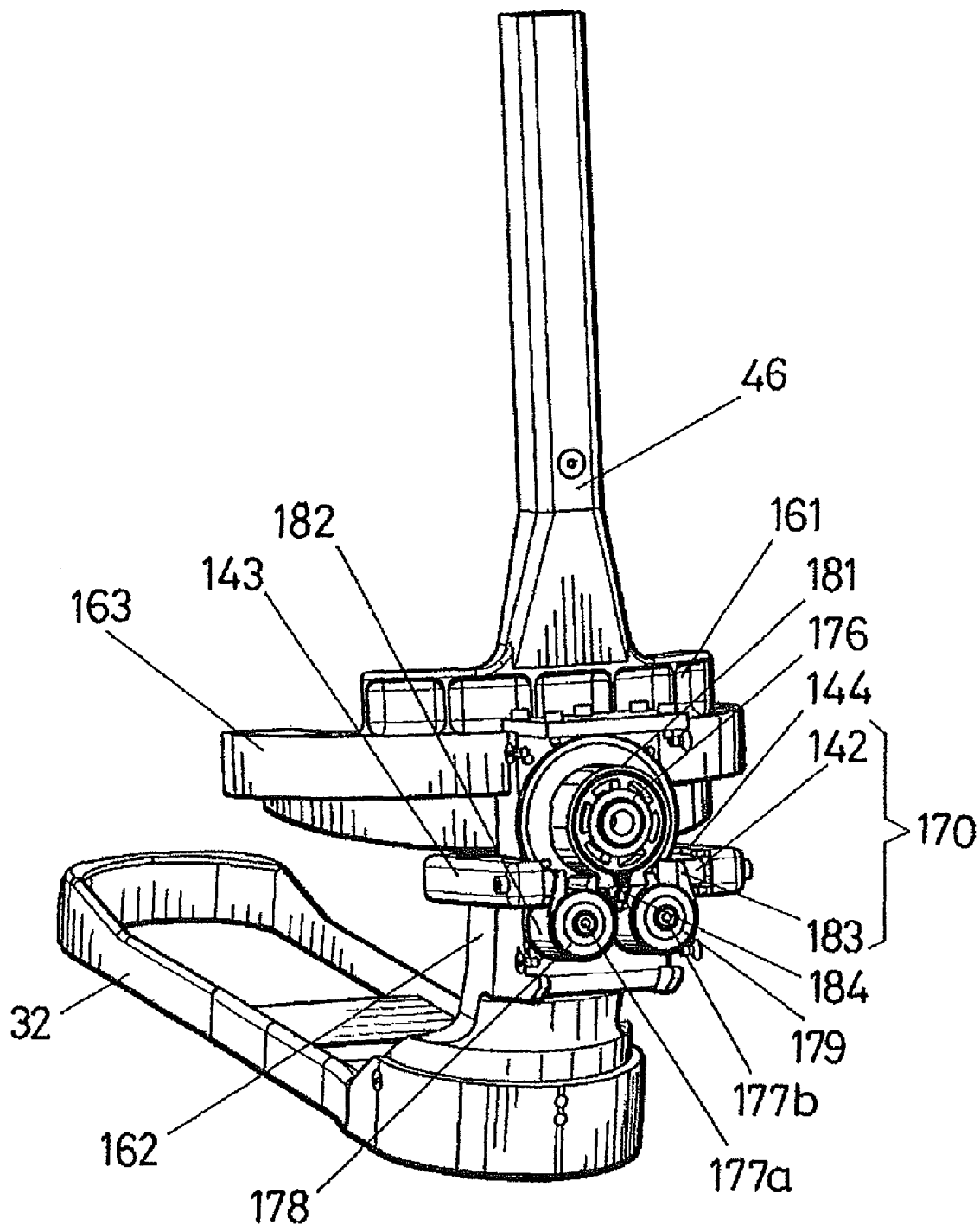
FIG. 17 shows a rear perspective view of the clutch device of FIG. 14 without the casing and showing the clutch mechanism.
Figure 18:
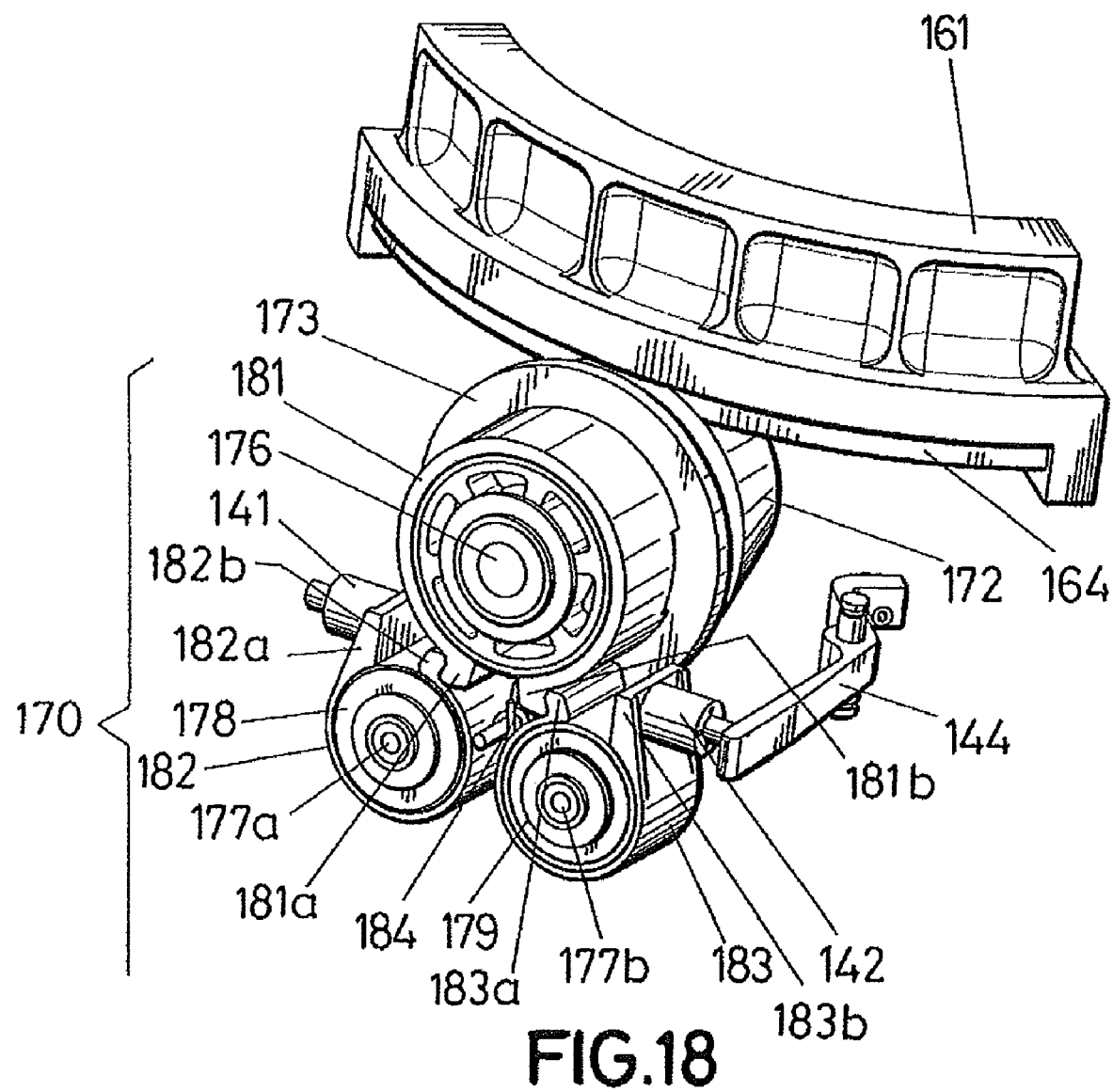
FIG. 18 shows a perspective view of the brake mechanism incorporated in the clutch mechanism.
Figure 19:
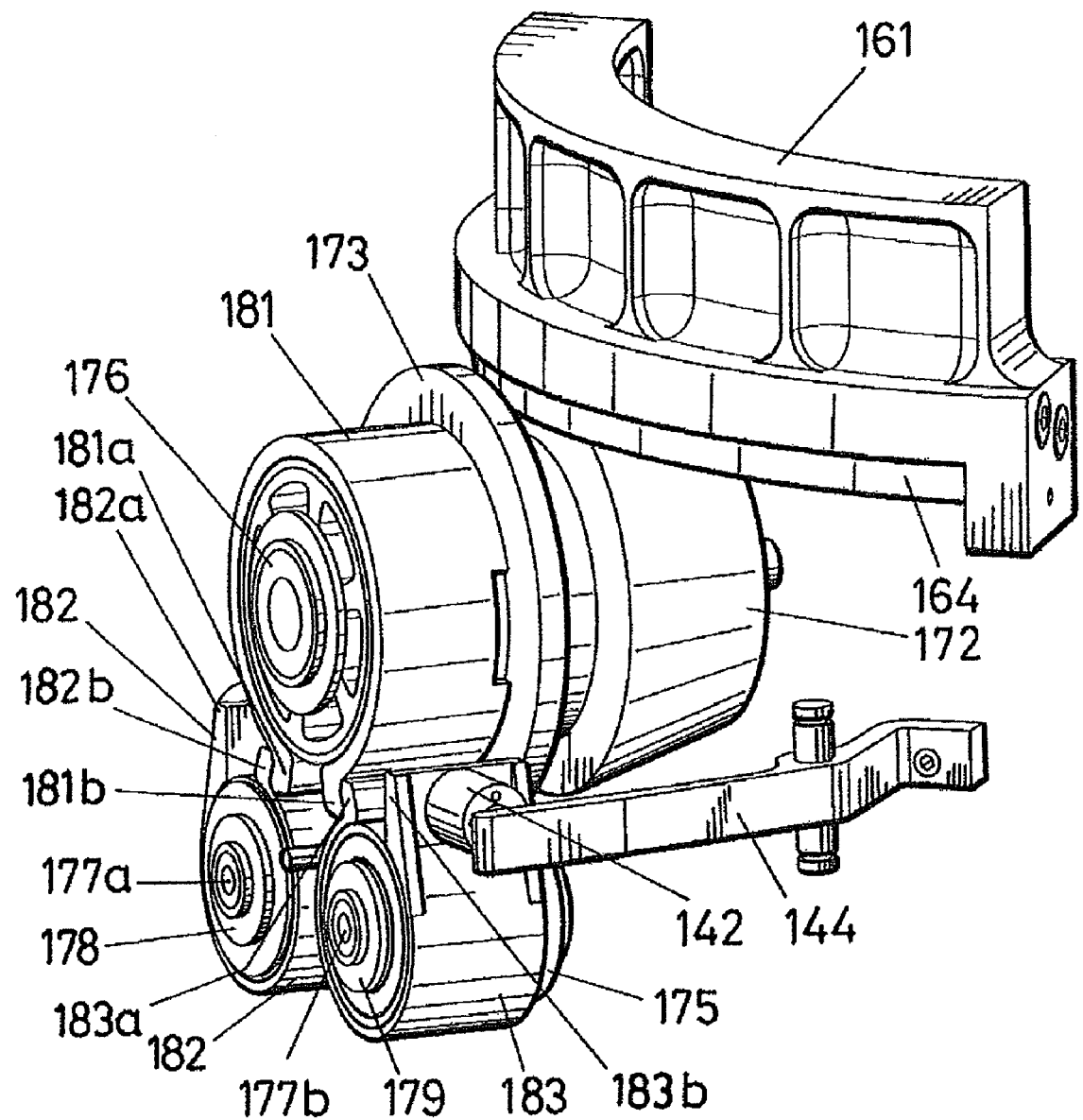
FIG. 19 shows a different enlarged view of FIG. 18.
Figure 20:
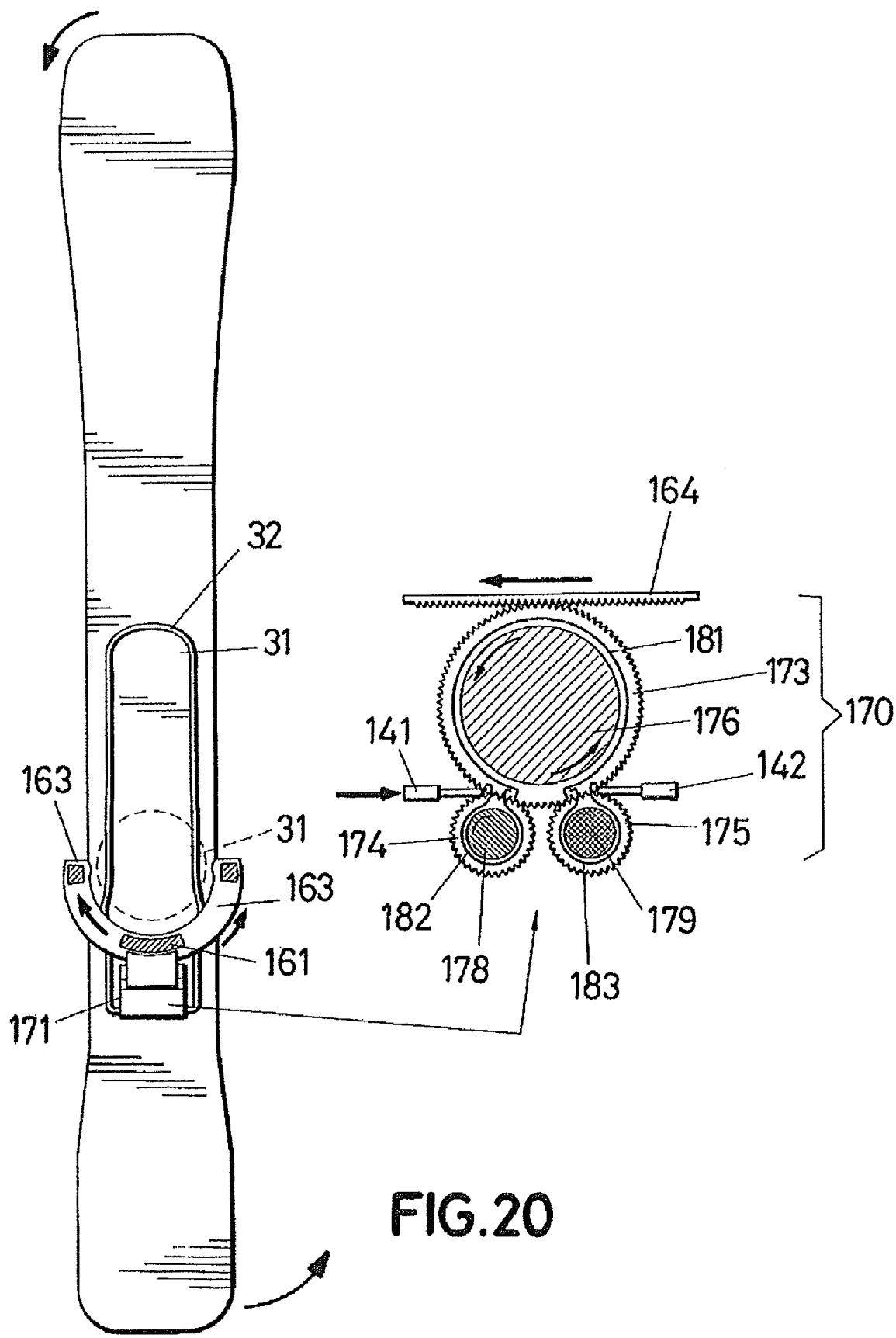
FIG. 20 shows diagrammatically operation of a preferred embodiment of the clutch mechanism.
Figure 21:
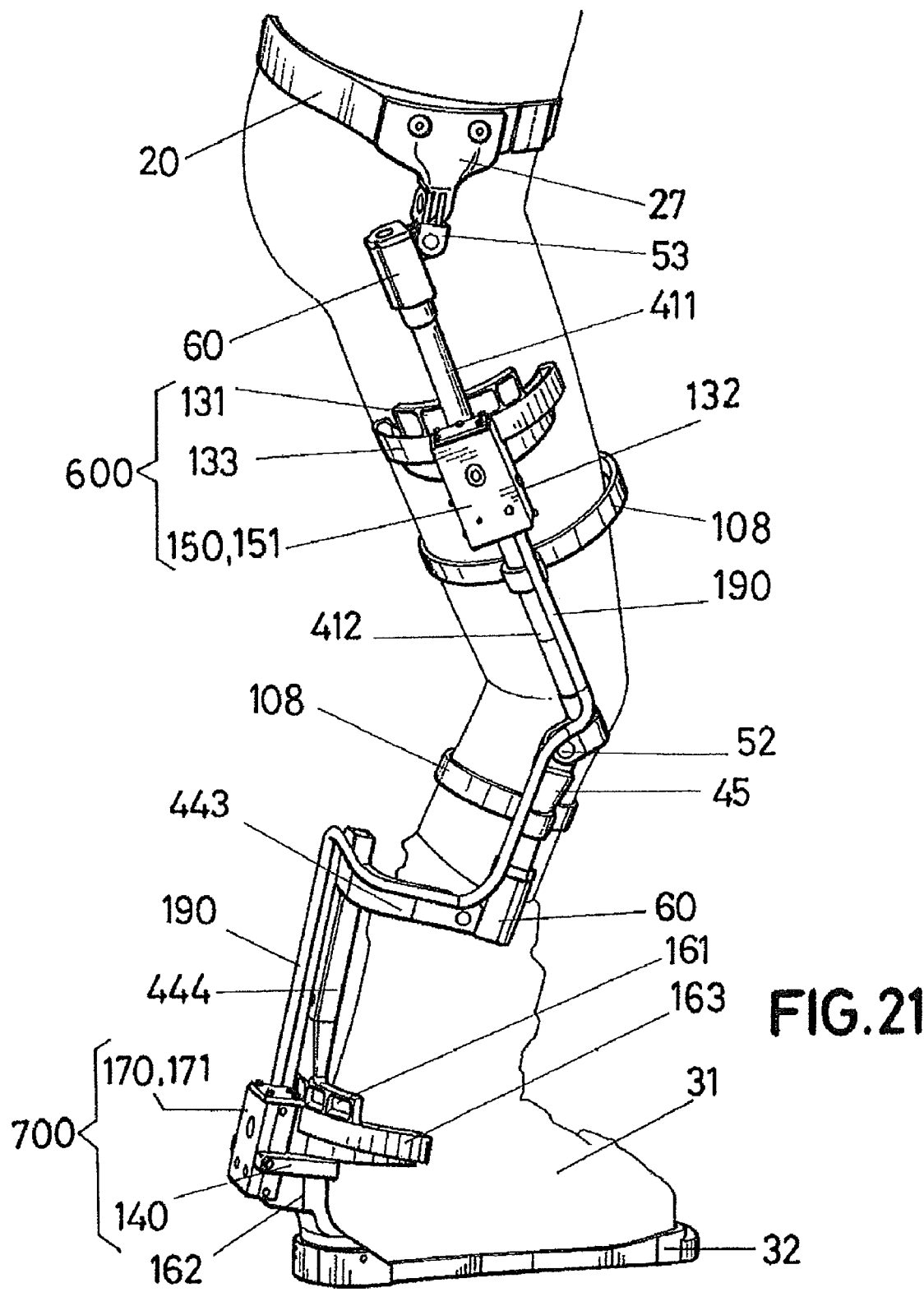
FIG. 21 shows a skier's lower extremities with the first exemplary embodiment of the invention.
Figure 22:
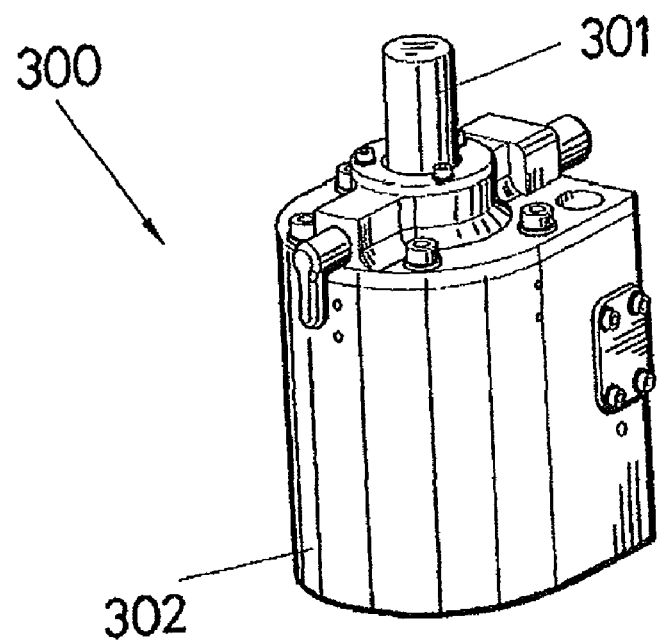
FIG. 22 shows a second embodiment of a clutch mechanism, specifically a hydraulic clutch mechanism.
Figure 23:
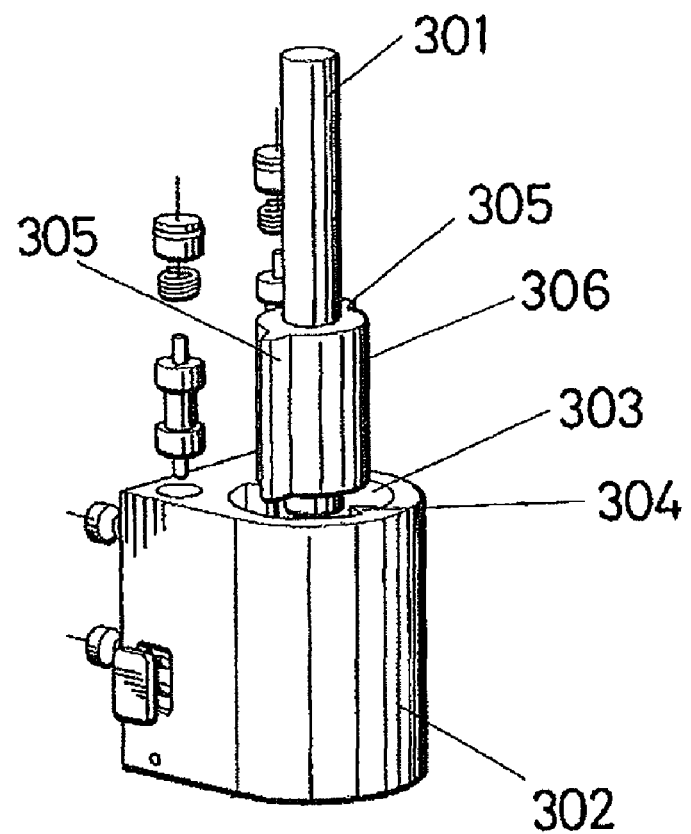
FIG. 23 shows a partial exploded view of the hydraulic clutch mechanism of FIG. 22.
Figure 25:
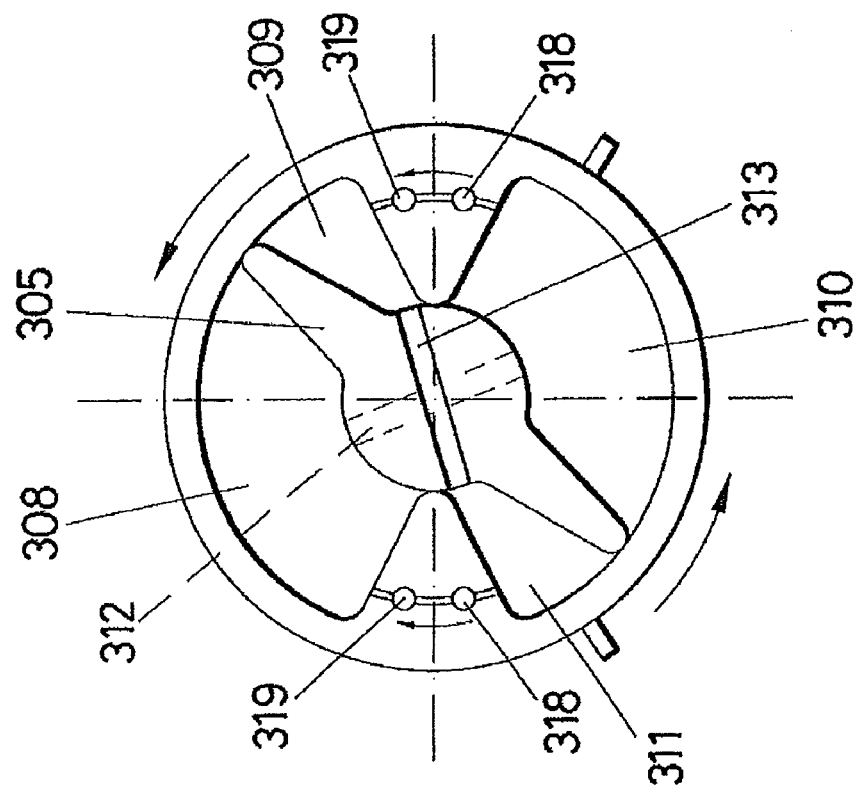
FIG. 25 shows an operation diagram when the hydraulic clutch mechanism of FIG. 22 is working.
Figure 24:
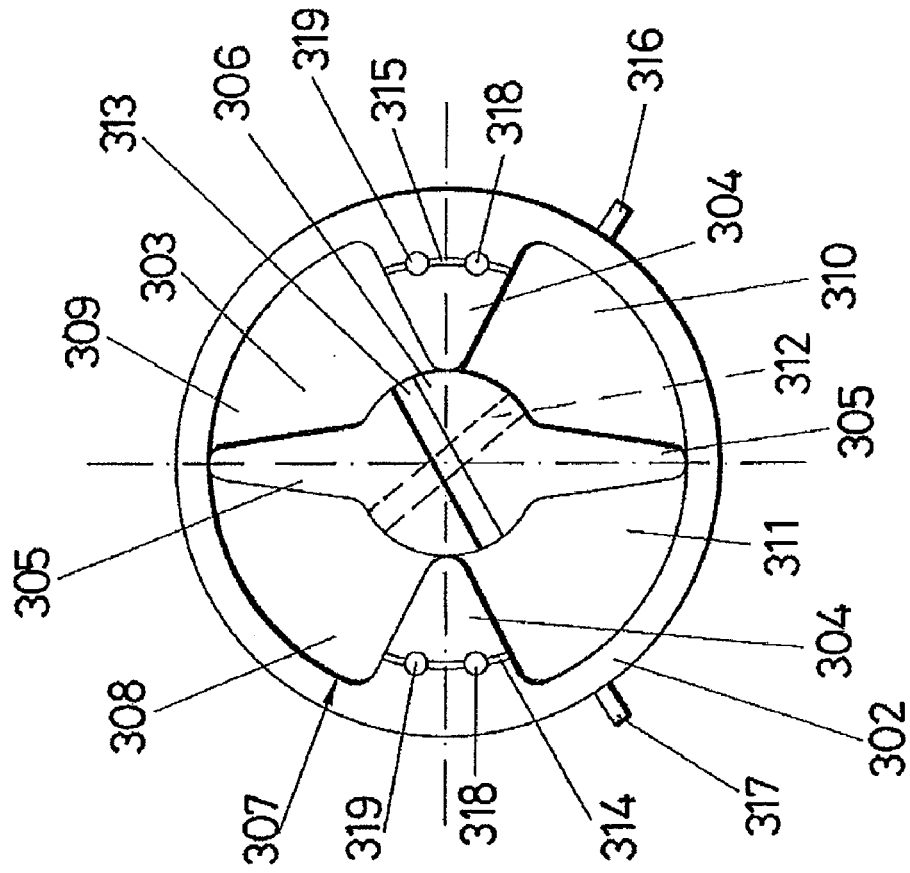
FIG. 24 shows an operation diagram when the hydraulic clutch mechanism of FIG. 22 is in standby position.

An alternative double hinge (53), shown in FIG. 2B, has its two axis turned 90 degrees in respect of the double hinge shown in FIG. 2.

The upper linkage assembly (41) is in turn sub-divided into two parts, linked to one another by a first or upper clutch mechanism (600) operatively connected to the exoskeleton, and in this case specifically connected to it such that the lower end of the upper part (411) of the upper linkage assembly (41) is linked to a sliding runner (131) of the first or upper clutch mechanism (600), and the upper end of the lower part (412) of the upper linkage assembly (41) is attached to the body (132) of the first clutch mechanism (600) that supports a rail (133) along which the runner (131) slides, incorporating a casing (151) with the components of the brake mechanism (150).

The upper linkage assembly (41) preferably has a strap (108) that surrounds the thigh (4) for keeping the upper linkage assembly (41) close to the skier's thigh (4).

The upper linkage assembly (41) is linked at its lower end to the lower linkage assembly (44), preferably at the height of the knee and using an artificial joint, such as a hinge type joint (52) allowing the natural flexion and extension of the knee (3), but not its torsion.

As mentioned, the lower linkage assembly (44) is linked at its upper end (45) to the hinge-type joint (52) at the height of the knee (2), whereas at its lower end it is linked to a length regulating mechanism (60) such as that described above, which allows changing the length of the lower linkage assembly (44) as well as disconnecting the exoskeleton from the second support member preferably the boot (31).

This length regulating mechanism (60) is integrated in the lower linkage assembly (44), which is divided into two parts by the length regulating mechanism (60): an upper part of the lower linkage assembly (441), extending from the height of the knee to the length regulating mechanism (60), and a lower part of the lower linkage assembly (442), extending from the length regulating mechanism (60) to the second support member (31). The mechanism (60) has a hinge (52) at its lower end making the lower linkage assembly (44) a jointed assembly, such that the lower part of lower linkage assembly (442) is made up of the mentioned hinge and an arc-shaped part or curved diversion member (443) surrounding the leg of the skier's boot (31) from the outer side part thereof to the rear part thereof, and an elongated vertical connecting member (444). The arc (443) is linked at its rear part by the elongated vertical connecting member (444) to the second or lower clutch mechanism (700) that is operatively connected, as the first clutch mechanism (600), to the exoskeleton through a second sliding runner (161) belonging to the second clutch mechanism (700) that connects the second or lower brake mechanism (170) to the exoskeleton. The artificial joint in the form of a hinge (52) located in the lower linkage assembly (44) and making it a jointed assembly is necessary in order to be able to absorb the forward and backward movements of the leg in the boot, such that the second clutch mechanism (700) is not driven by the rest of the exoskeleton when the leg moves, thus isolating the movements of the leg in the boot of the exoskeleton.

As in the first clutch mechanism (600), this second clutch mechanism (700) of the exoskeleton, as shown in FIGS. 14 to 20, has a body (162) supporting a rail (163) along which a runner (161) slides and connects the second brake mechanism (170) to the exoskeleton, more specifically the casing (171) of the second or lower brake mechanism (170) containing the components of the second brake mechanism (170) and therefore the main components of the second or lower clutch mechanism (700). The second or lower clutch mechanism (700) is coupled to a clog or lower base (32) through the body (162) and the casing (171), and attached to the boot (31) through the sole thereof. The second brake mechanism (170) is in contact with a sensing device (140) made up of members activating the brake mechanism (170).

The operation of the second or lower clutch mechanism (700) used in this preferred embodiment and which can be extended to the first or upper clutch mechanism (600) is described below.

The mentioned runner (161) has in its lower part a round conical gear section (164) meshing with the actual brake mechanism (170) and located inside the casing (171). Specifically, the round conical or bevel gear section (164) of the runner (161) meshes with a corresponding conical or bevel gear or pinion (172), located in said casing (171), which is in turn integral to a first "large" pinion (173) meshing with two second small pinions (174, 175). The first large pinion (173) moves a rotor or primary (176). The second small pinions (174, 175) move the shafts (177) of secondary or "free wheel" bushings (178, 179). These secondary or "free wheel" bushings are arranged to rotate, the left one (178) in clockwise direction and the right one (179) in counter-clockwise direction, such that movement of the foot results in the runner sliding on the rail causing the foregoing components to move with the exception of one of the "free wheel" bushings (178, 179), such that when the left bushing (178) moves, it does so only in the clockwise direction and when the right bushing (179) moves, it does so only in counter-clockwise direction.

The rotor (176) and the "free wheel" bushings (178, 179) are preferably coated with a Ferodo-type friction material and have bands or curved structures (181, 182, 183) around them, each of them with two ends. The primary band (181) that surrounds the rotor (176) has a left end (181a) and a right end (181b) that remain separated in the lower zone of the rotor (176), and secondary bands (182, 183) surrounding the bushings (178, 179) have a free exterior end (182a, 183b) and a free interior end (182b, 183a), remaining the free ends of each band separated in the upper zone of each bushing. These bands (181, 182, 183) are connected to one another, such that the free interior ends (182b, 183a) of the secondary bands (182, 183) surrounding the bushings (178, 179) press against the left and right ends (181a, 181b) of the primary band (181) surrounding the rotor (176) under certain conditions.

The brake mechanism (170) has a spring (184) which remains tensed in this example when the system is inactive with at least 100 N at each end of the primary band (181) surrounding the rotor or primary (176). The tension, as well as all the parameters of the system, will be regulated depending on who uses the invention and the conditions of use.

Arranged on each side of the casing (171) there is a thruster (141, 142) that acts, depending on the movement received by the sensing device (140), either on the end of the left secondary band (182) of the left bushing (178) or on the end of the right secondary band (183) of the right bushing (179). The thrusters (141, 142) act every time the boot (31) exerts pressure on one of the sensors, in the form of a rocker arm, (143, 144) of the sensing device (140), the pressure being transmitted through sensors (143, 144) directly to the thruster (141, 142).

The body (162) of the second clutch mechanism (700) of the exoskeleton, which provides support to the casing of the brake mechanism (171) and to the rail (163), extends and is linked to the clog or lower base (32) in which the sole of the boot (31) is introduced, such that the rear part of the clog (32) is housed in the heel part of the binding of the ski just as the heel of a ski boot would be, and at its front part the clog (32) is fixed at the toe part of the binding of the ski just as the toe of a boot would be. The size of the clog (32) is such that it adjusts to the sides of the sole of the boot (31) at its front part and progressively and slightly separates therefrom until there is preferably a maximum allowance of approximately 1 mm on each side between the sole of the boot (31) and the clog (32), in the rear part.

The operation of the system while being used by a skier is described below, such that at any time pressure is exerted on the ski at one of its ends opposite the one on which pressure is exerted by the boot (31), for example, when the ski tries to turn in counter-clockwise direction and the boot in clockwise direction, the following actions occur in the lower clutch mechanism (700):

1) The runner (161) starts to slide on the rail (163) in the opposite direction to the direction in which the ski tends to turn, i.e. clockwise. The sliding of the runner (161) induces the rotation of the main rotor (176), connected to the runner (161) by the conical pinion (172) and the conical gear section (164), in counter-clockwise direction.

2) The shaft (177a) of the left free wheel bushing (178) and the left free wheel bushing (178) itself rotate in clockwise direction.

3) Given that the boot (31) turns in clockwise direction due to the allowance existing between the rear part of the sole of the boot (31) and the rear part of the clog (32), the left sensor in the form of a rocker arm (143) transmits preferably no greater than 10 kg of pressure to the left thruster (141), which in turn exerts pressure on the secondary left band (182) surrounding the bushing of that side, i.e. the left bushing (178). In the present example this pressure exerted on the thrusters (141, 142) is preferably no greater than 10 kg, but it can be regulated depending on the characteristics of the user of the invention as well as of the use conditions thereof. The pressure causes a braking force of the bushing on the same side, i.e. the left side (178), which is a function of the initial force applied by the thruster (141), the coefficient of friction of the friction material of the left bushing (178), and the contact angle (in radians) in which the secondary left band (182) surrounds the left bushing (178), according to the formula $$F_{end} = F_{initial} * e^{\mu \alpha} \quad (1)$$

where "$F_{end}$" is the force exerted on the bushing; "$F_{initial}$" is the force exerted by the thruster; "µ" is the coefficient of friction of the friction material of the bushing; "e" is a mathematical constant; and "α" is the contact angle (in radians) between the band and the friction material of the bushing.

4) In turn, given that the support of the end opposite to the end on which the left thruster (141) exerts pressure on the secondary band (182) surrounding the left bushing (178), is the link of the secondary left band (182) with the left end of the main band (181) surrounding the main rotor (176), and through the way in which the system is built, applies the entire end braking force generated in the left bushing (178) as the initial force in the main band (181) of the main rotor (176) inducing a much greater braking force thereon according to the following formula:

$$F_{end} = F_{initial} * e \quad (2)$$

where "$F_{end}$" is the force exerted on the rotor; "$F_{initial}$" is the braking force of the bushing; "u" is the coefficient of friction of the friction material of the rotor; "e" is a mathematical constant; "α1" is the contact angle (in radians) between the band and the friction material of the bushing; and "α2" is the contact angle (in radians) between the band and the friction material of the rotor.

5) Therefore, when the rotor (176) brakes, it causes the conical pinion (172) integral to the rotor and therefore the gear section (164) forming part of the runner (161) to brake as well, thereby preventing the runner (161) from sliding along the rail (163), such that "it couples" the exoskeleton to the boot (31). The greater part of the torque exerted by the ski is thus transmitted to the first support member through all the components of the exoskeleton, given that the first or upper clutch mechanism (600) acts at the same time as the second or lower clutch mechanism (700). That is to say, the first brake mechanism (150) acts in unison with the second brake mechanism (170) and rest of components of the clutch mechanisms.

Nevertheless, if the boot (31) moves in the same direction of the torque exerted by the ski, nothing in the system opposes such movement, so the skier's intentional movements will not be limited by the device. In this case, and assuming that the inactive thruster is the right thruster (142), the latter could exert preferably pressure of a maximum of 100 N (in this preferred embodiment this is achieved using for the rocker arm (144) of the sensor a material and a design such that when the force of 100 N is exceeded, the rocker arm (144) flexes) on the end closest to it of the secondary band (183) surrounding the right bushing (179). The spring (184) which keeps the ends of the main band (181) surrounding the rotor or primary (176) separated preferably exerts a force of 100 N, whereby preventing the effect of undesirable braking according to which the rotor (176) would tend to come off the band (181), such that if the input force is not amplified the band will not touch the rotor and therefore the rotor doe not act.

The "free wheel" mechanism of the bushings (178, 179) prevents any unwanted interlocking of the system, since on one hand it keeps the secondary bushing which is not activated completely disconnected from the system, and on the other hand immediately releases the active secondary bushing as soon as the rotation direction of the system changes, regardless of the braking force being exerted at that time. Therefore, the left and right bushings are one way free wheel type bushings such that the left bushing can only transmit the torque of the shaft in clockwise direction and the right bushing can only transmit the torque in counter-clockwise direction.

Additionally, it is suitable for the device to incorporate safety mechanisms such that they keep the skier protected in the event that the primary systems fail. In the preferred mode explained above, this mechanism is formed by the stops of the rail limiting the lateral shifting of the runner.

The operation of the first or upper clutch mechanism (600), located in the upper linkage assembly (41) is identical to the second or lower clutch mechanism (700), previously described, the main body (132) in this case being linked to the upper end of the lower part of the upper linkage assembly (412), instead of being linked to the clog (32), and the thrusters receiving from this first brake or clutch mechanism (150) the pressure of the sensors (140) through a pressure transfer or directing mechanism formed by rigid components (190) and flexible components (191), for example, pressure transmitting shafts and cables that run inside the rigid or flexible components (190, 191).

The operation of both clutch mechanisms (600, 700) can be coordinated in several ways, for example:

By the arrangement of a set of sensors acting at the same time on both clutch mechanisms, first and second;

By the arrangement of two sets of sensors, such that the first set of sensors acts on the first clutch mechanism and the second set of sensors acts on the second clutch mechanism; and By the arrangement of a set of sensors acting on the sensors of the second clutch mechanism, while the clutch mechanism in turn operates as a sensor and acts on the first clutch mechanism.

In one preferred embodiment, a single set of sensors acts on both clutches, directly on the second one and through transfer on the first one.

With the device explained as preferred embodiment, the following objectives are thus obtained:
- The ski is always perfectly controlled by the skier;
- Before reaching a position that could cause damage to the exoskeleton, the clutch mechanisms prevents the boot from turning; and
- If the force produced by the ski exceeds the binding setting values, the binding would be released by the action of the exoskeleton and its support in the strong areas of the body, protecting the joints and bones.

With the foregoing device, the skier will feel at all times that he or she has control over the skis, precision in the movements that he or she chooses to make, and more importantly, the certainty that the entire body structure from the waist to the feet is protected against any movement that could cause a bone or joint injury.

The operation of other alternative clutch mechanisms will be explained below.

A second alternative clutch mechanism (300) as shown in FIGS. 22 to 25, for example, is a hydraulic device such that, depending on the rotation direction about its vertical axis in combination with the application of a certain stimulus caused by the activated sensor when the ski "tries" to move in a direction not wanted by the skier, generates a resistant torque proportional to the stimulus that can block the shaft (301) of the hydraulic device (300) that is operatively connected to the linkage assembly (40) of the exoskeleton. This blocking of the shaft (301) of the hydraulic device connected operatively to the linkage assembly (40), the upper linkage assembly (41), the lower linkage assembly (44), or both, fixes or couples the second support member, specifically the boot (31), to the exoskeleton to prevent unwanted rotation in single direction, allowing freedom for the movement of the boot in the direction wanted by the skier.

The hydraulic mechanism (300) is formed by a body (302) which is preferably fixed to the rear part of the boot, inside which there is a cylindrical cavity (303) with two diametrically opposed cavity flanges (304). Housed inside this cavity (303) there is a rotating actuator (306) with two symmetrical actuator flanges (305) integral to a shaft (301) which in turn is integral to the linkage assembly (40) of the exoskeleton. These symmetrical actuator rotating flanges (305) form a sealed closure with the walls (307) of the cylindrical cavity (303), in the same way that the cavity flanges (304) in the main body (302) close in a sealed manner against the shaft (301). The cylindrical cavity (303) is thus divided into four cavities (308, 309, 310, 311). There are two ducts, a first duct (312) and a second duct (313), diagonally traversing the rotating actuator (306), such that each of the four cavities communicates with its diagonally opposed cavity, i.e. the first duct (312) communicates the first cavity (308) with the third cavity (310) and the second duct (313) communicates the second cavity (309) with the fourth cavity (311), maintaining equal pressure in each pair of diagonally opposing cavities.

There are two other communication ducts, a third duct (314) and fourth duct (315), that get through the main body (302) of the device, so that the third duct (314) connects the first cavity (308) with the fourth cavity (311) and the fourth duct (315) connects the second cavity (309) with the third cavity (310), that is to say, connecting the contiguous cavities separated by the cavity flanges (304). Each of this two conducts (314, 315) has a non-return valve (318). The direction of the non-return valve of a duct is opposite to the direction of the non-return valve of the other duct.

The hydraulic mechanism (300) also has two sensors (316, 317) receiving pressure, which can be transmitted from the sensors (140) through hydraulic, mechanical, electronic mechanisms, etc. These sensors (316, 317) actuate the valves (319) regulating the passage of fluid in the communication ducts (314, 315) located in the main body (302).

All the cavities (308, 309, 310, 311) in the main body (302), as well as the communication ducts (312, 313, 314, 315) are full of fluid, preferably oil, especial for high pressure hydraulic mechanisms.

The hydraulic device (300) acts when one of the two skis starts to turn, open, close or perform any other movement that the skier does not want. When this happens, the skier's foot will apply pressure or otherwise actuate the sensor on the side opposite to the one which the ski is trying to move, in turn causing the "clutch" or coupling of the control mechanism with the linkage assembly (40) of the exoskeleton structure indiscriminately, i.e. the exoskeleton structure couples to the mechanism and prevents the foot from moving along with the ski in the unwanted direction, but it allows it to move or turn in the direction that the skier wants.

When the foot exerts a pressure on the inside of the boot (31), a lateral force is therefore generated between the foot and the boot. Somewhere between the foot and the boot, i.e. between the boot and the inner boot, where this pressure is received, the sensor or hydraulic or electronic mechanisms which will send the signal to the device (300) which will be firmly linked to the boot (31) and to the exoskeleton.

The sensors work in pairs on opposite sides in an alternating manner, i.e., the sensors on both sides of a pair are not activated at the same time. Only one of them can be activated at all times. The non-return valves (318) also work in an alternating manner, one at a time. According to the sensor which is activated, this will in turn activate one of the valves, which will block the passage of the fluid in a manner that is proportional to the pressure received from one cavity to the other, exerting a braking effect on the linkage assembly (40) in one of the rotation directions, allowing rotation in the opposite direction.

This progressive braking blocks all movement of the shaft (301) in the main body (302), making the entire exoskeleton integral to the boot, but only in one direction, the direction of the turn not wanted by the skier, in contrast allowing the foot to turn in the direction that the skier wants.

The exoskeleton thus achieves the effect that the ski, by the operation of the device described above (sensor->actuator->non-return valve->fluid->rotor/cavity->exoskeleton) follows the movements provided by the skier, helping the skier to overcome the resistance exerted by the ski, while it is blocked by the entire device, for the purpose of any movement not wanted by the skier.

This blocking of the linkage assemblies (40) fixes or couples the boot to the exoskeleton, in the unwanted rotation direction, leaving the boot free to move in the direction wanted by the skier.

Likewise, if the sensors are located between the boot and the binding, as previously mentioned, it is necessary to isolate the pressure exerted by the foot from the total pressure exerted by the foot plus the exoskeleton. In such case, one way of doing this is by including an additional hydraulic connection without a valve between each sensor (hydraulic in this case) and the chamber of the hydraulic mechanism or clutch. This connection is independent of the one already explained which transmits the pressure from the sensor to the valve regulating the clutch-declutch action. Its function is to take away or neutralize the pressure that the exoskeleton exerts on the sensor, allowing the hydraulic mechanism or clutch to be directed by the net pressure exerted by the foot on the sensor. Nevertheless, there are many other ways to solve this problem, not just by means of hydraulic mechanisms but also by means of mechanical or electronic mechanism, to name a few.

Similar objectives are met by this second alternative clutch mechanism as with the first clutch mechanism previously described in the preferred embodiment.

As in the previous example, the clutch would operate a similar way if the couplings or connections or ends thereof are exchanged, for example, the main body of the clutch mechanism, mainly the brake mechanism, is placed at the end of the linkage assembly and the shaft at the second support member, the boot in this case. It could also likewise be used in the upper linkage assembly and first support member.

Furthermore, it is suitable for the device to incorporate safety mechanisms such that they keep the skier protected in the event of failure of the primary control ski systems. These safety mechanisms, that could be mechanical, hydraulic, electronic, pneumatic, etc., can provide protection against injuries, even in the event that the sensors, or the connection between these sensors and the actuators, or the actuators themselves, or even the brake mechanism of the clutch mechanism itself should fail. In other words, protection is maintained even if all the links of the chain fail, with the exception of the actual strong members, such as shafts and the exoskeleton itself.

For example, in the first preferred embodiment in case any of the clutch mechanism fails, or even both, the components of the same, specifically the runner and the rail, can still work as angle limitation mechanisms, so they will prevent a greater rotation than the one established by the user before starting to use the safety and control device.

A third kind of clutch mechanism (400) is shown in FIGS. 26 and 27 and is designed to be placed on the lower end of the linkage assembly (46). Unlike the previous ones, this clutch mechanism is introduced in a housing (407) arranged under the boot and integral to the sole thereof, the connection between the device or exoskeleton and the coupling to the boot being carried out in the rear part (408) of the housing (407) and therefore of the boot, specifically in the heel. The linkage assembly (40) or the lower linkage assembly (44) reaches the housing (407) and is connected to the clutch mechanism (400) included in the housing (407), transmitting the torque when the clutch mechanism (400) starts to operate.

This clutch mechanism (400) is preferably made up of:

at least two "sensors" or push buttons (403, 404), located on both sides of each ski boot providing to the mechanism (400) the rotation direction information required by the skier; and a system which, according to the position of the foot and its resistance, diverts more or less torque to the structure formed by the exoskeleton, the strong areas of the leg and the waist through a mechanism (400) acting as an effective clutch coupling or decoupling the lower end of the linkage assembly (46) to or from the mechanism (400) that is coupled to the boot (31) through the rear part (408) of the housing (407).

The sensors (403, 404) will be activated by the skier when skiing in a natural manner, such that, if the skier wants to move his or her leg in one direction, it will actuate one of these sensors (403, 404) automatically by the force naturally used to move his or her leg. Likewise, if a ski starts a movement not wanted by the skier, the corresponding sensor will activate the mechanism.

This alternative clutch mechanism (400) includes a gear train (402) and an alternative braking/blocking system (401), one of the ends of which is connected through the rear part (408) of the housing (407) to the lower end of the linkage assembly (46) integral to the exoskeleton and the other one discriminately clutches or declutches according to the information received by the sensor (403, 404), which in this specific case includes a push button (403, 404) on each side of the housing as explained above. The use of gears (402) reduces the torque generated in the foot, such that it performs more effective and more precise braking. The minor slips of the braking wheel (401) are geared down by the gear train (402), minimizing the allowances in the transmission to the exoskeleton, gaining in precision.

If a push button (403, 404) receives the pressure from the foot, it pushes a rocking arm (405, 406) that acts over the braking wheel (401) and the system automatically clutches or couples the boot to the linkage assembly (40) and therefore to the exoskeleton, only in the unwanted rotation direction (interpreted by which push button (403, 404), left or right, is activated) making the foot integral to the entire support structure (exoskeleton, strong areas of the leg, waist), in that unwanted direction, but allowing total freedom for any rotation in the direction that the foot wants to go.

The boot (31) and the housing (407) of the mechanism (400) are linked by any suitable attachment mechanism, for example, a screw and nut system, such that the housing (407) becomes integral to the lower part of the boot (31). The link with the binding in the skis is carried out through the housing (407) and not the boot. In operation, each push button or sensor (403, 404), located in the front outer part of the housing (407), between the housing (407) and the binding, acts on a rocking arm (405, 406), such that the rocking arm (405, 406) comes into contact with the braking wheel (401) that gears with the first wheel of the gear train (402), (the contact being able to be ribbed, Ferode-type or notched), causing the braking only in one of the directions, and amplifying the resistance up to the last cogwheel.

By means of the forces created by the skier by moving on the push buttons (403, 404), the mechanism acting on the last wheel is activated once the input movement has been geared down, thus blocking the system in one direction or the other, depending on which push button (403, 404) has been activated, indiscriminately making boot (31) and exoskeleton integral to one another, as previously explained, when braking this last wheel at will.

It is possible that the clutch system (400) is integrated with or forms one piece with the boot (31), such that the ski boot includes the clutch mechanism (400) integral therewith.

As with the sensors and the transmissions, the clutch mechanisms can also be of other types in addition to being mechanical or hydraulic, such as electronic for example, or different combinations of electronic components with mechanical, hydraulic components, etc.

The use of the mentioned electronic members, such as contact sensors, pressure sensors, movement sensors, accelerometers, travel measuring devices, electronically actuated valves, small programmable computers etc., all battery-powered, allows easier control over the clutch mechanisms, more adjustment capacity while at the same time simplifying many mechanisms since the electronically managed functions that would otherwise have to be managed by hydraulic mechanisms, pneumatic mechanisms, etc.

All the previous mechanisms, clutch, sensors and/or transmission (electronic, mechanical, hydraulic, etc.) can be combined in different manners to obtain the mentioned objectives of the present invention.

The described clutch mechanisms (300, 400, 600, 700) can be combined with other exoskeleton examples, in addition to the example described in the first preferred embodiment above, as explained below.

Figure 28:
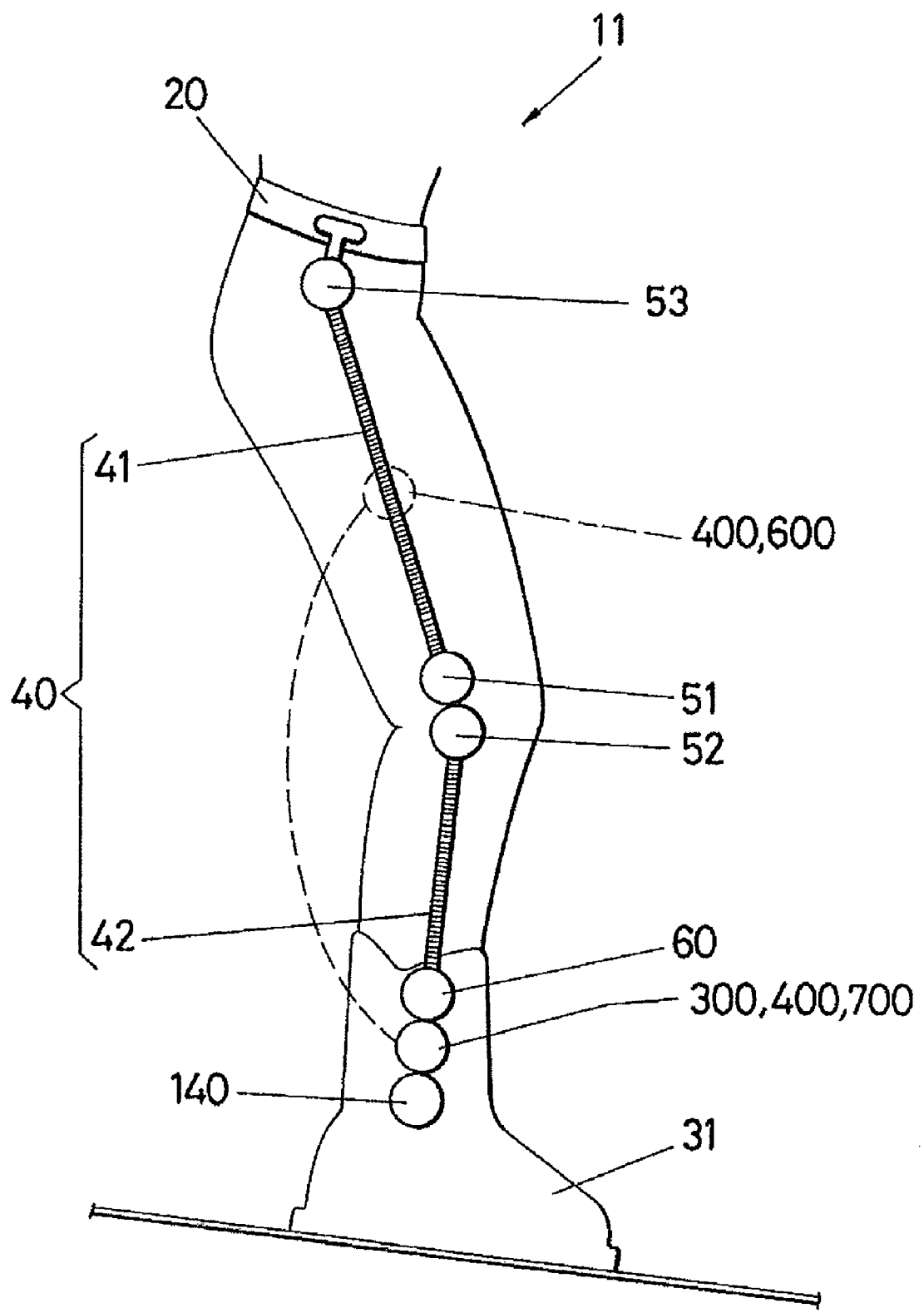
FIG. 28 shows a skier's lower extremity with a schematic depiction of a second exemplary embodiment of the invention.

A second preferred embodiment (11), FIG. 28, of the safety and control exoskeleton for snow skiing incorporates only one clutch mechanism (300, 600) located in the upper linkage assembly (41) or only one clutch mechanism (300, 400, 700) in the lower linkage assembly (44), its operation similar to that described in the first preferred embodiment but limited only to one clutch mechanism, (600, 700, 300, 400). The clutch mechanism (300, 400, 600, 700) will be duly connected to the corresponding sensing device (140). In this second preferred embodiment of the exoskeleton, and as a coupling device between the upper linkage assembly (41) and the lower linkage assembly (44), an artificial joint at the height of the knee, specifically a hinge (52), is used in combination with a torque transmission artificial joint (51) that allows transmitting rotation movement regardless of the angle formed by the members it connects, i.e., the upper linkage assembly (41) and the lower linkage assembly (44). This last artificial joint (51) can be, for example, a Cardan or universal joint or any artificial joint with the desired features.

The basic components of this second exoskeleton embodiment (11) are adapted to the type of clutch mechanism, having the components of the exoskeleton, such as the first support member (21) and second support member (31) having features that are common to or similar with those previously described for the first embodiment (10), and duly adapted artificial joints or links between the different components. For example, the coupling between the upper linkage assembly (41) and the first support member (21) can be done by any torque transmission mechanism or artificial joint (51) that can transmit torque between two elements regardless of the angular alignment between them. Accordingly, torque can be transmitted between those two elements, allowing the transmission independently of the angular alignment between the axis of both elements, as would be the case, for example, of a universal or Cardan joint (51).

As stated, however, this second embodiment (11) differs from the first preferred embodiment (10) in that, instead of using two clutches and one hinge-type knee joint, this second embodiment can operate with only one clutch (300, 400, 600, 700) as a result of the incorporation in its knee artificial joint of a torque transmission mechanism that allows torque transmission between the axis of two linkage assemblies connected by the transmission mechanism, independently of the angular alignment between both axes, using, for example, a train of Cardan joints, a flexible joint, a cable transmitting the rotation like the cables of odometers do, or a torque transmission mechanism (500) combined with a clutch mechanism as described below and shown in FIGS. 51 to 54.

This torque transmission mechanism (500) works in combination with a clutch mechanism worked up by sensors and which reaction is transmitted to the torque transmission mechanism through a cable acting directly on the clutch (520). The clutch (520) can be located in the upper linkage assembly or in the lower linkage assembly.

The torque transmission mechanism (500) with a clutch mechanism (520) integrated in the lower linkage assembly (44), is formed by a lower curved rail (502) located below the knee and surrounding the leg and another upper curved rail (501) located above the knee and surrounding the leg, i.e., a lower curved rail (502) linked to the upper end (45) of the lower linkage assembly (44) and other upper curved rail (501) linked to the lower end (43) of the upper linkage assembly (41).

Housed in both rails (501, 502) there are respective runners (503, 504) that can shift along the rails (501, 502), being linked by a cable (505) and having pulleys (506). The cable (505) is arranged such that a runner (503, 504) can only shift along its corresponding rail (501, 502) in one direction if the other runner (503, 504) shifts in the opposite direction.

The runners (503, 504) are linked by an articulated rigid member (507) that bends when the knee is bent. The cable (505) connects one runner (503) to the other runner (504) through the ends of the curved rails (501, 502) in the following manner with reference FIG. 51:

The end of the cable (505) is linked to the right end (503a) of the upper rail (501), goes to the upper runner (503), passing through the same, to subsequently reach the lower runner (504) through the articulated rigid member (507). The cable (505) passes through the lower runner (504) and comes out on their right side (504a) towards the right end (502a) of the lower rail (502) that it surrounds, returning to the center of the lower rail (502) before reaching the brake of the clutch mechanism (520) and subsequently take the reverse path, i.e., left end of the lower rail (502b), left end of the lower runner (504b), upward passage traversing the articulated rigid linking member (507) of both runners (503, 504), coming out at the left end of the upper runner (503b), and ending at the left end of the upper rail (501b).

When the clutch mechanism (520) is activated through the sensing device (140), thereby preventing the movement of the cable, both rails (501, 502) will maintain their relative angular positions, i.e. there will be no relative rotation between them, which means that no relative torsion between the first support member and the second support member will occur, regardless of the relative positions of the rails (501, 502) and runners (503, 504), or, in other words, regardless of the voluntary torsion of the knee.

However, if the clutch mechanism (520) is deactivated, the relative angular positions of the rails may change freely, i.e. there may be relative torsion between the first support member and the second support member.

Pulleys (506) are used for rotations of the cable along the mechanism, but other elements, such as guide pipes, bearings, etc., can be used and the components can be flexible or rigid, depending on where they will be located in the mechanism.

It is also possible to invert the mechanism and make the runners mobile and the rails fixed.

Figure 29:
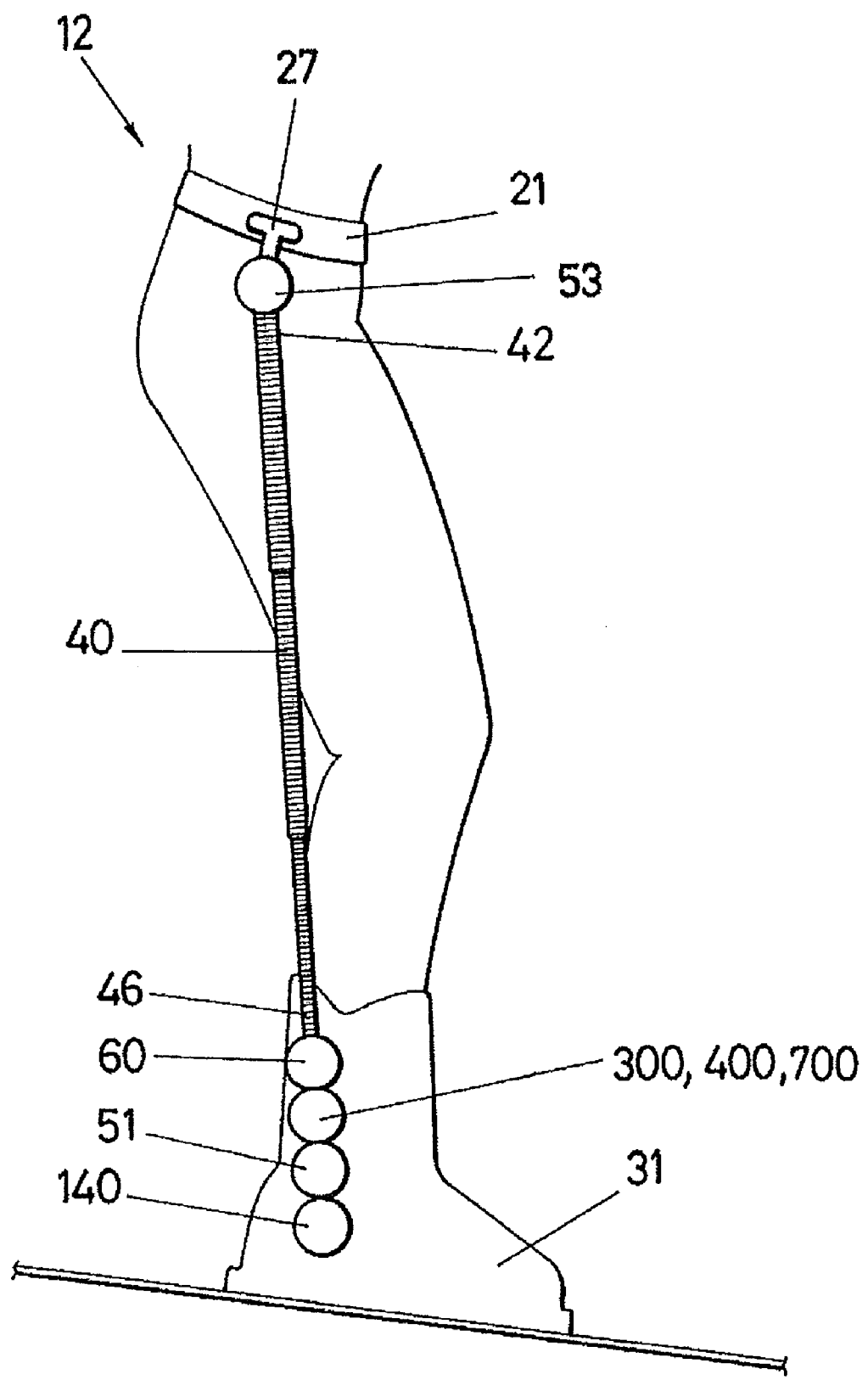
FIG. 29 shows a skier's lower extremity with a schematic depiction of a third exemplary embodiment of the invention.

A third preferred embodiment (12) of the exoskeleton according to the present invention and shown in FIG. 29 uses a single linkage assembly by eliminating the connection or artificial joint of the upper linkage assembly (41) and the lower linkage assembly (44) at the height of the knee (2), the linkage assembly (40) preferably being extensible, and being located between the first support member located, preferably as a rigid belt (21), at the waist or hips (5) and the second support member located at the boot (31), binding or ski.

Like the previously described exoskeleton, this exoskeleton also incorporates at least an artificial joint (51) such that it transmits the torque between the torsion axis of the elements connected by it, allowing said torque transmission regardless of the angular alignment between both torque axis, being the joint placed at the linkage assembly (40) between the two support elements (21, 31). It further incorporates a torque transmission joint (51) between the sensing device (140) and the clutch mechanism (700, 300, 400) located in the lower end (46) of the linkage assembly (40). This system automatically extends or retracts according to the extension-flexion movements of the skier's leg.

Figure 30:
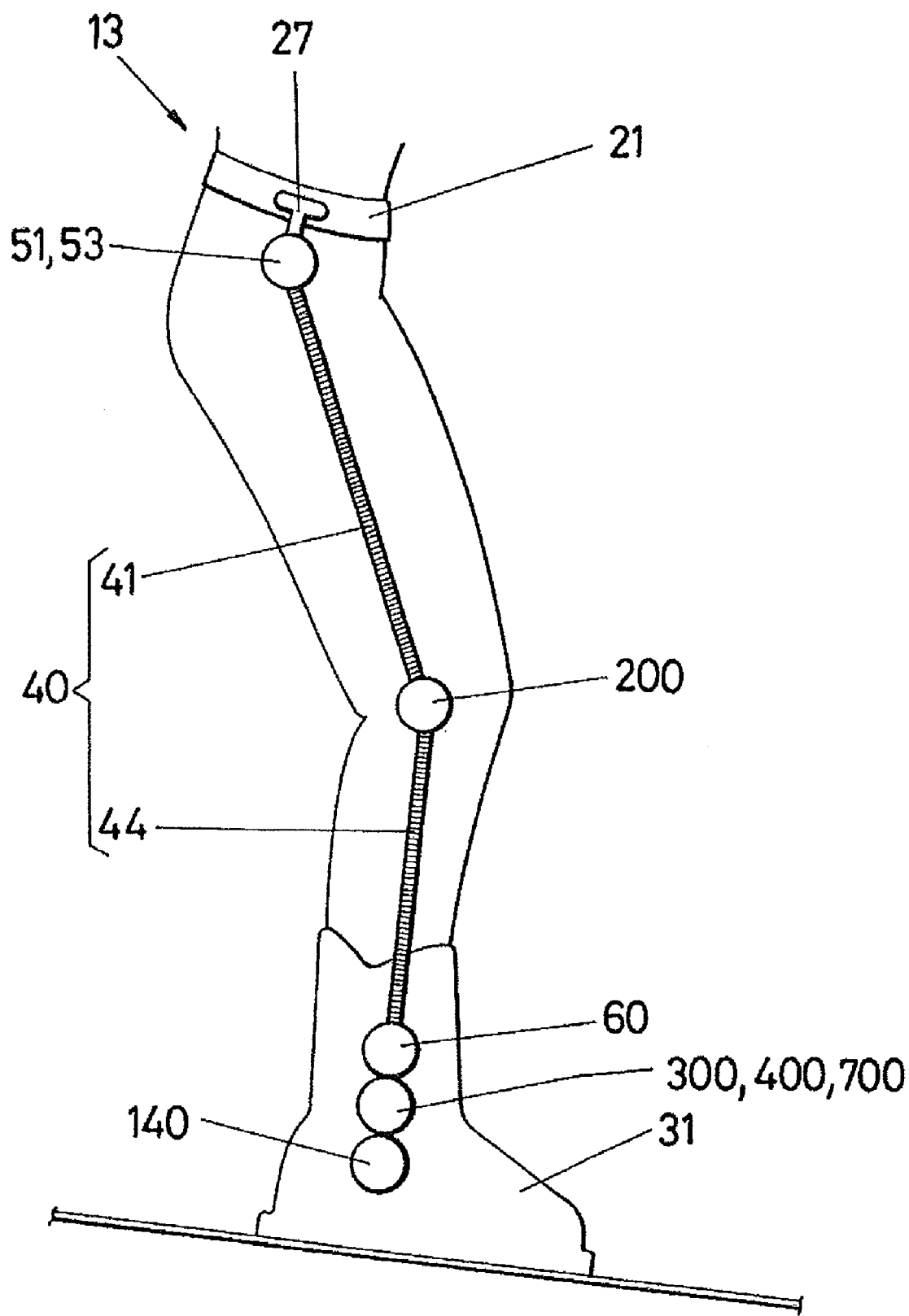
FIG. 30 shows a skier's lower extremity with a schematic depiction of a fourth exemplary embodiment of the invention.
Figure 31:
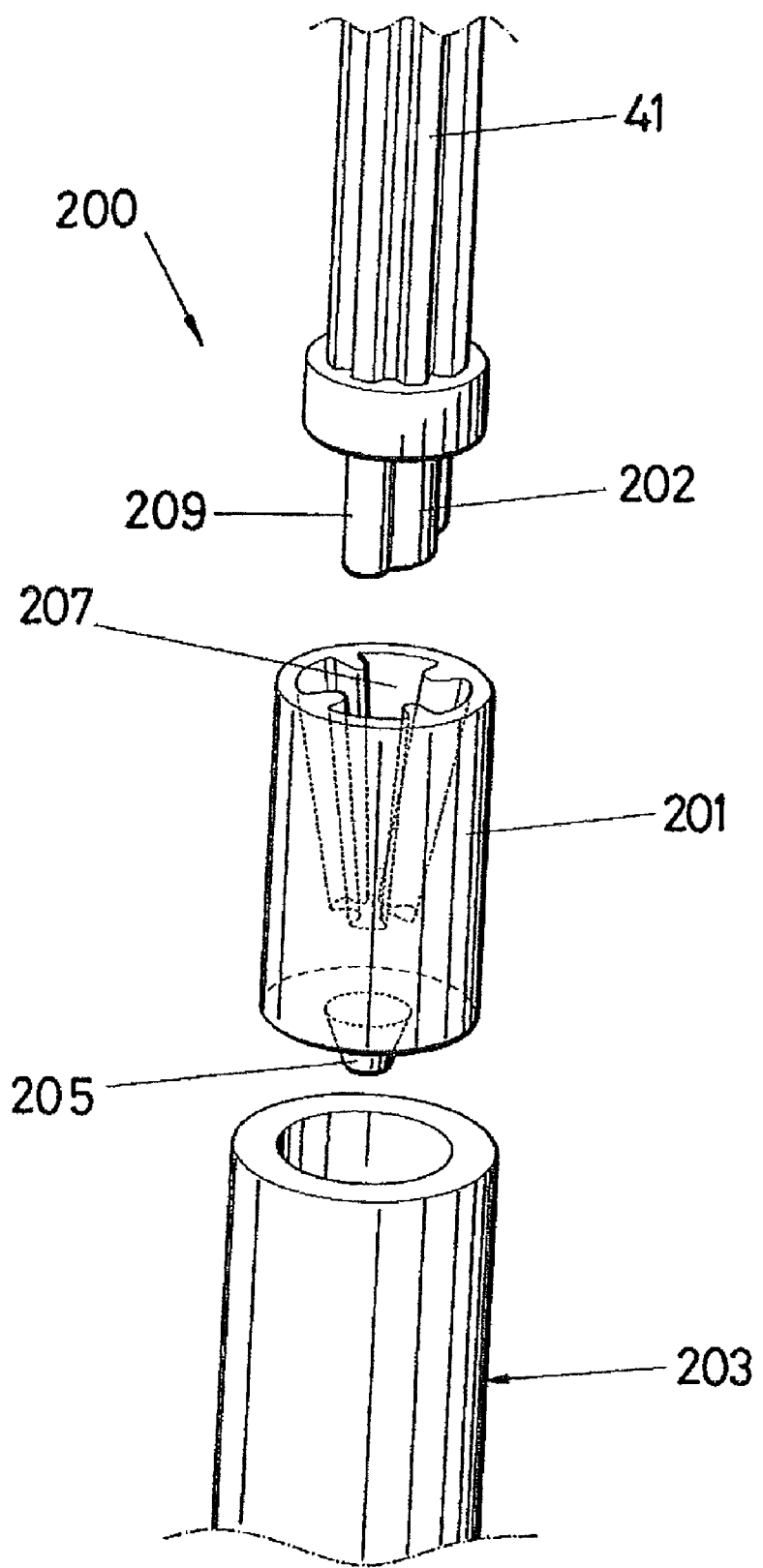
FIG. 31 shows an exploded view of a knee-angle sensitive to flexion limitation mechanism.

A fourth preferred embodiment (13) of the exoskeleton according to the present invention shown in FIG. 30 is similar to the embodiment first described. It uses a first support member, preferably a belt (21) located at the height of the hips or waist (5) and has a first artificial joint, for example a double hinge joint (53), or a universal joint or an elastic joint (51), at its sides for linking it to the upper linkage assembly (41). A knee angle limitation mechanism, shown in FIGS. 31 to 36 is used in the lower end (43) of the upper linking end, at the height of the knee (2) of the skier or user, and as a nexus for connection to the lower linkage assembly, (44), the mechanism being located at the height of the knee (200) and angle-sensitive with respect to flexion thereof, such that it allows greater or lesser freedom of rotation of the upper linkage assembly (41) depending on how flexed the knee (2) is. If the knee is completely flexed, the upper linkage assembly (41) has complete freedom to rotate within the limits defined by the angle limitation mechanism (200), but if the knee is completely extended, the upper linkage assembly (41) is completely integral to the lower linkage assembly (44), being therefore impossible to rotate. Obviously the angle-sensitive limitation mechanism (200) allows intermediate progressive coupling positions between both limit positions. The objective of this sensitive angle limitation mechanism (200) is to allow the rotation of the femur in the hips with the knee being flexed, allowing pendulum movement with the knee being bent. When the leg is extended, the freedom of rotation is managed with the clutch.

As can be seen in FIGS. 31 to 36, the sensitive angle limitation mechanism (200) has a straight shaft (202) coupled or forming part of the upper linkage assembly (41), with the same width along its entire extension, that is housed in a hub or cylinder (201) with an inner cavity (207) with a decreasing conical shape.

Specifically the cavity (207) of the hub (201) has four ribs or nerves (208) that are parallel to its decreasing section and the shaft (202) introduced in the hub (201) has two opposite projections (209) at the end of the shaft (202), so that each of the projections (209) when the shaft (202) is introduced in the cavity (207) remains between two nerves (208) of the cavity (207). The deeper the shaft in the cavity the more its rotational capacity is limited, completely blocking it when it is completely housed, and completely free (only limited by the pre-adjusted range by the user throughout the angle limitation mechanism) when it is out of the cavity (207).

Figure 34:
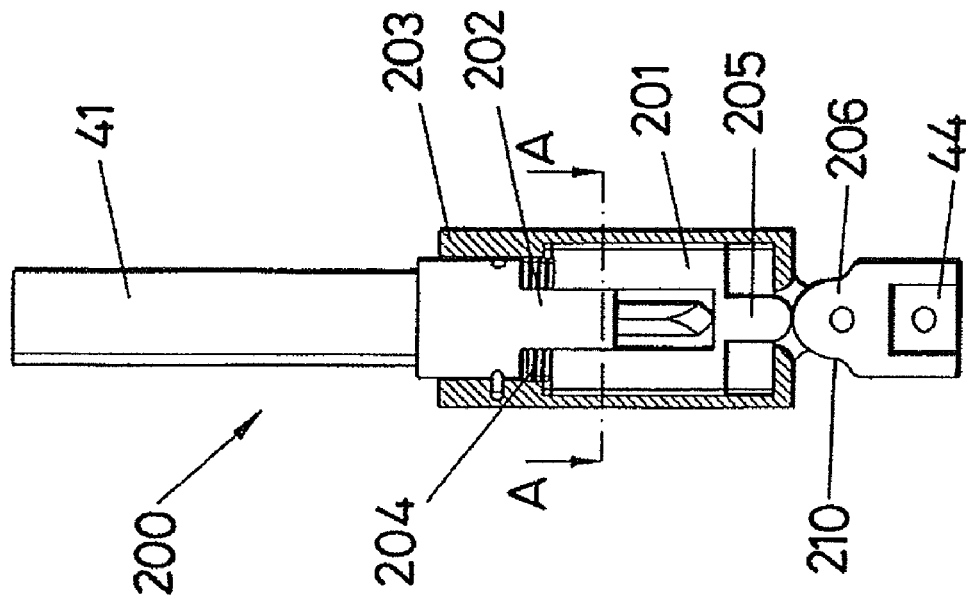
FIG. 34 shows a section view of the knee-angle limitation mechanism when the knee is not flexed.
Figure 33:
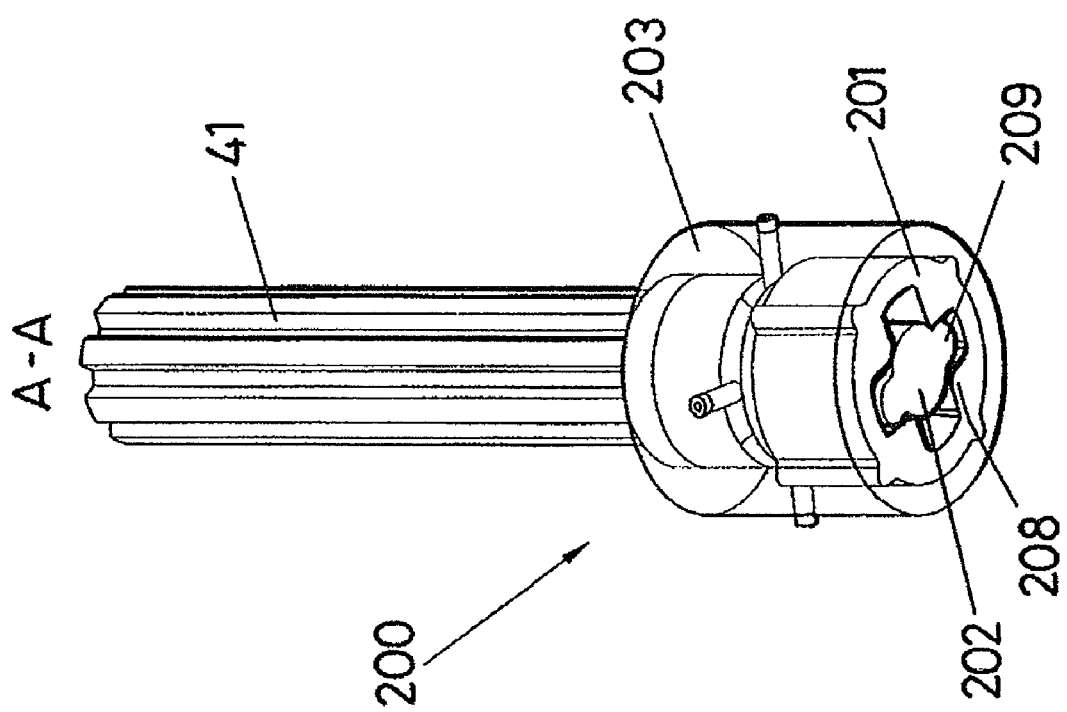
FIG. 33 shows a perspective view, with a section through AA in FIG. 34, of the mechanism of FIG. 31 when the knee is not flexed.
Figure 36:
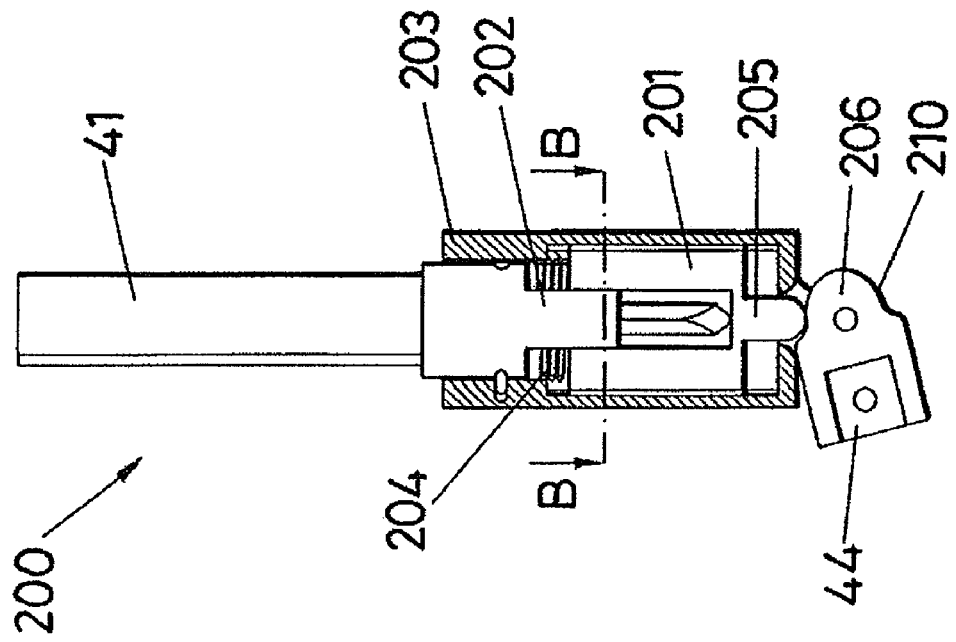
FIG. 36 shows a section view of the knee-angle limitation mechanism when the knee is flexed.
Figure 35:
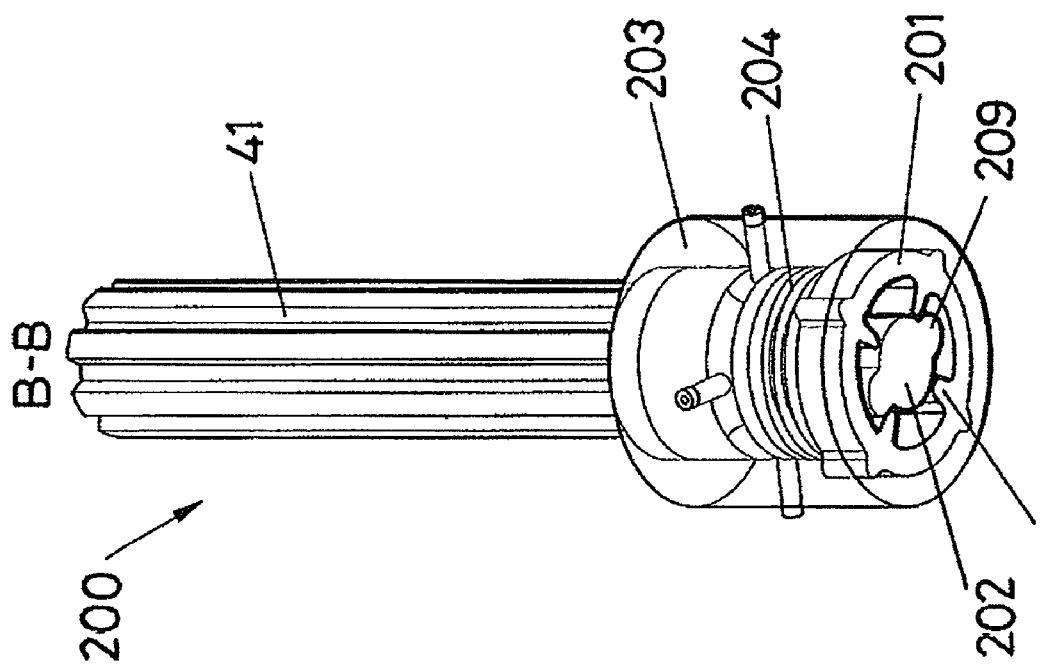
FIG. 35 shows a perspective view, with a section through BB in FIG. 36, of the mechanism of FIG. 31 when the knee is flexed.

With reference to FIGS. 33 and 34, when the knee is not flexed, the upper end (45) of the lower linkage assembly (44) pushes a hub projection (205) placed on the outer low surface of the hub (201) and due to the action of a spring (204) pushing the projections (209) of the shaft (202) remains near the bottom of the cavity (207) in the hub (201). In this position, the path that the projections (209) can move between two nerves (208) is null as shown in FIG. 33.

On the other hand, with reference to FIGS. 33 and 34, when the knee is flexed, the upper end (45) of the lower linkage assembly (44), provided with a curved profile (210), makes the hub projection (205) run over the profile (210) making the shaft (202) and therefore the projections (209) move upwards inside the hub (201) cavity (207). In this position the path between the nerves (208) of the cavity (207) is enough to allow the rotation of the projections (209) between said nerves.

Accordingly, the angles of the rotation will depend on the amount the knee is bent.

As in the first embodiment of the exoskeleton described, the lower part of the lower linkage assemblies are linked to each side of the skier's body preferably with a quick fixing member (60) of the type previously described and which can also be used as a device for extending the linkage assemblies, and for linking the lower linkage assemblies (44) to the second support member, for example the ski boots (31) or the binding of the boot to the ski or the actual ski. A clutch mechanism (700, 300, 400) of the type of those previously described and sensing elements (140) detecting the movement of the foot, are arranged in each of the skier's boots.

Figure 37:
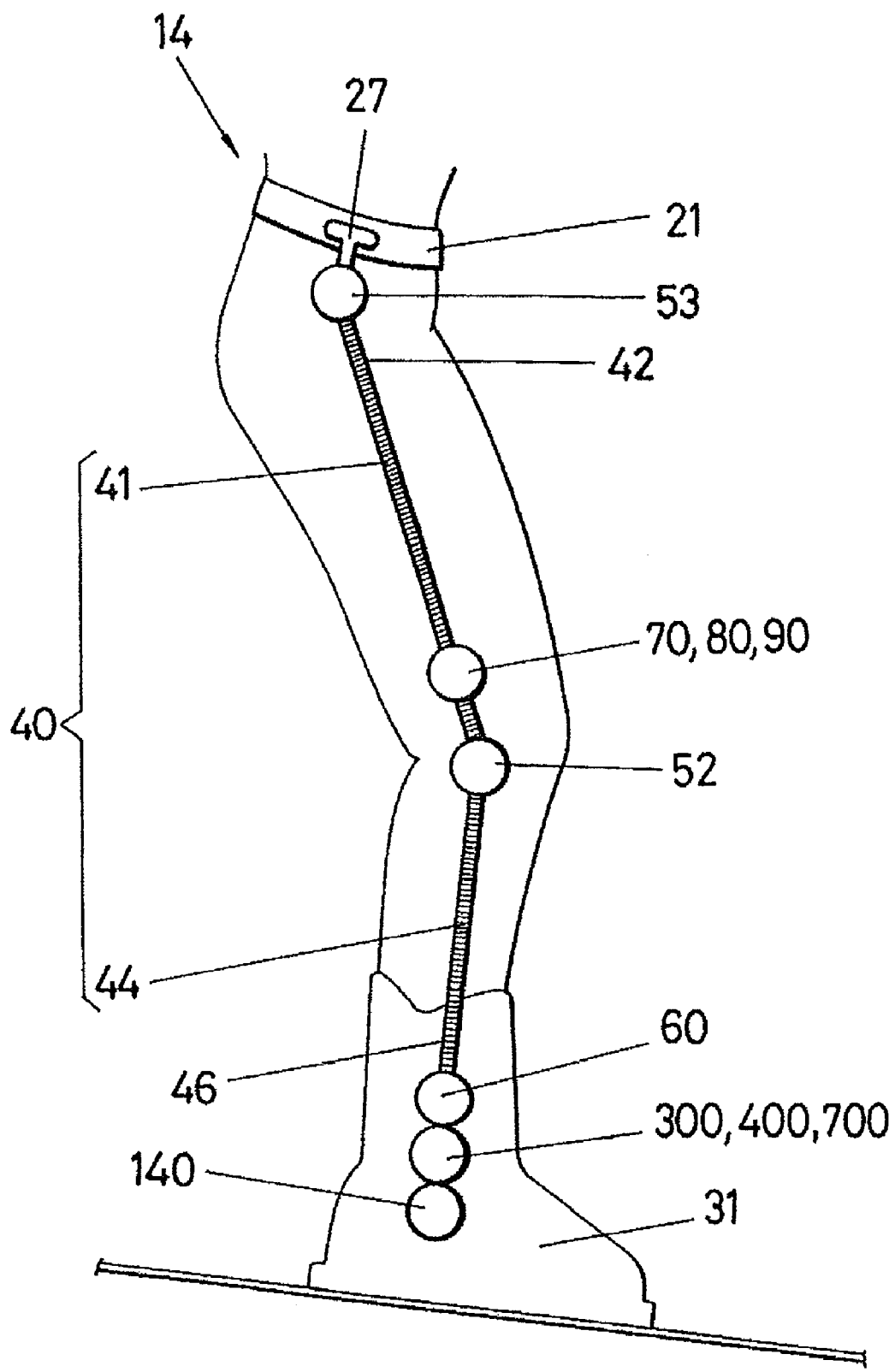
FIG. 37 shows a skier's lower extremity with a schematic depiction of a fifth exemplary embodiment of the invention.
Figure 38:
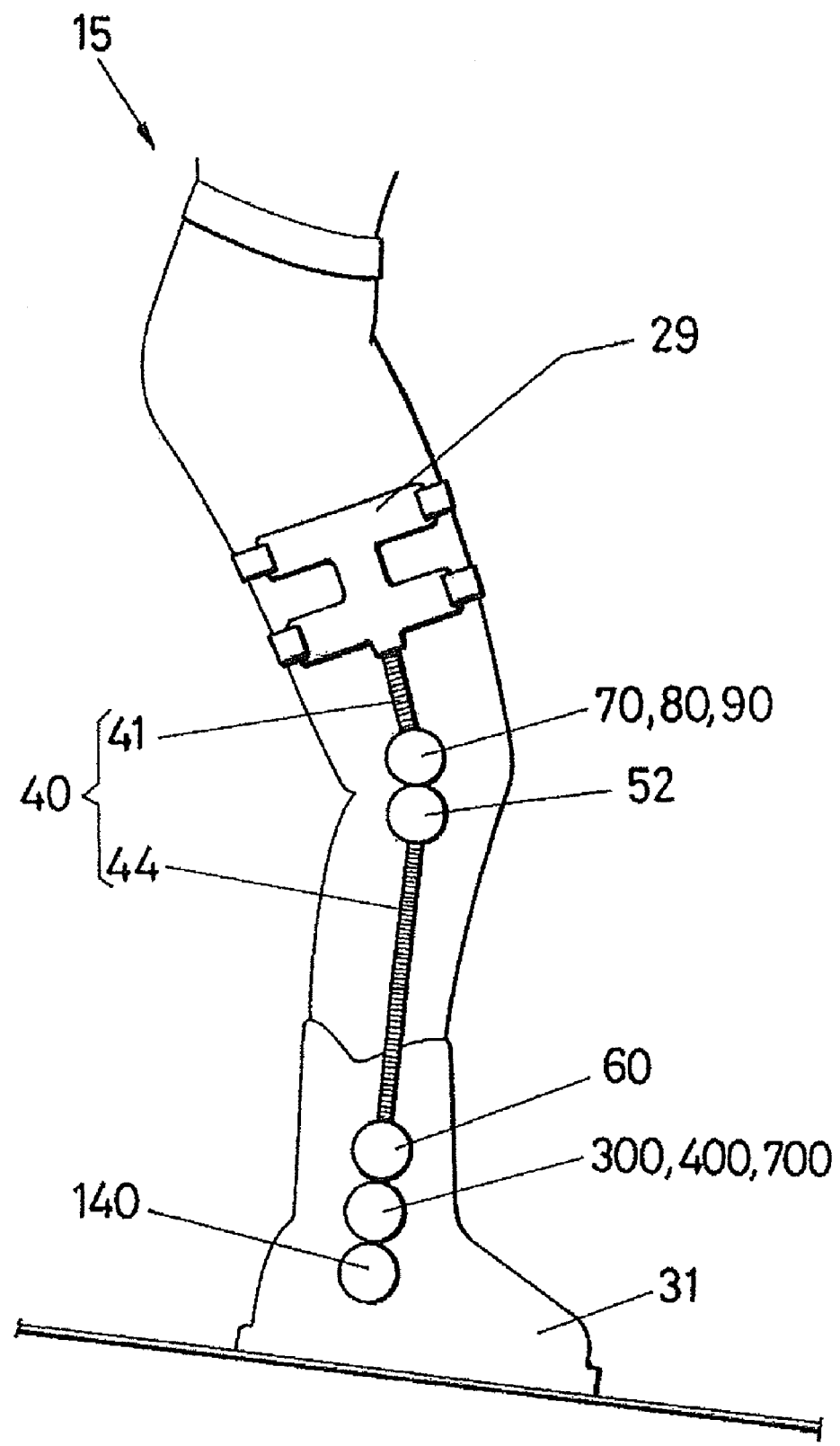
FIG. 38 shows a skier's lower extremity with a schematic depiction of a sixth exemplary embodiment of the invention.

In a fifth embodiment (14) of the exoskeleton according to the present invention and shown in FIG. 37, instead of using a knee joint mechanism (200) sensitive to the bending angle of the knee as the one previously described, it is possible to use at the height of the knee a hinge in combination with a rotation angle limiting device or angle limitation mechanism (ALM) (70, 80, 90) located in the upper linkage assembly (41). The ALM (70, 80, 90) limits the rotation of the upper end (42) of the upper linkage assembly (41) and the lower end (43) of the assembly (41) about an axis passing through the upper and lower ends of the linkage assembly. In this example, the clutch mechanism (600, 300, 400) is located in the lower linkage assembly, and preferably connected to the second support member and to the lower end (46) of the lower linkage assembly (44), for example through a length regulating mechanism or quick coupling mechanism (60). The upper linkage assembly (41) is linked to the first support member through a joint, for example a double hinge (53) joint or a universal joint (51) between others.

The above angle limitation can be made using different mechanisms. It is possible to include at any point along the upper linkage assembly (41), between the first rigid support member and the knee (2) an angle limitation mechanism or rotation limiting mechanism (ALM) (70, 80, 90) in a parallel axis to the longitudinal axis of the femur allowing the free rotation, inside the preferred limits defined by the user, in two axes and limiting rotation about said longitudinal axis of the body. This ALM limits the rotation or relative torsion between the upper end (42) of the upper linkage assembly (41) and the lower end (46) of the lower linkage assembly (44) around an axis passing through the upper (42) and lower (46) ends of the linkage assembly (40).

Figure 39:
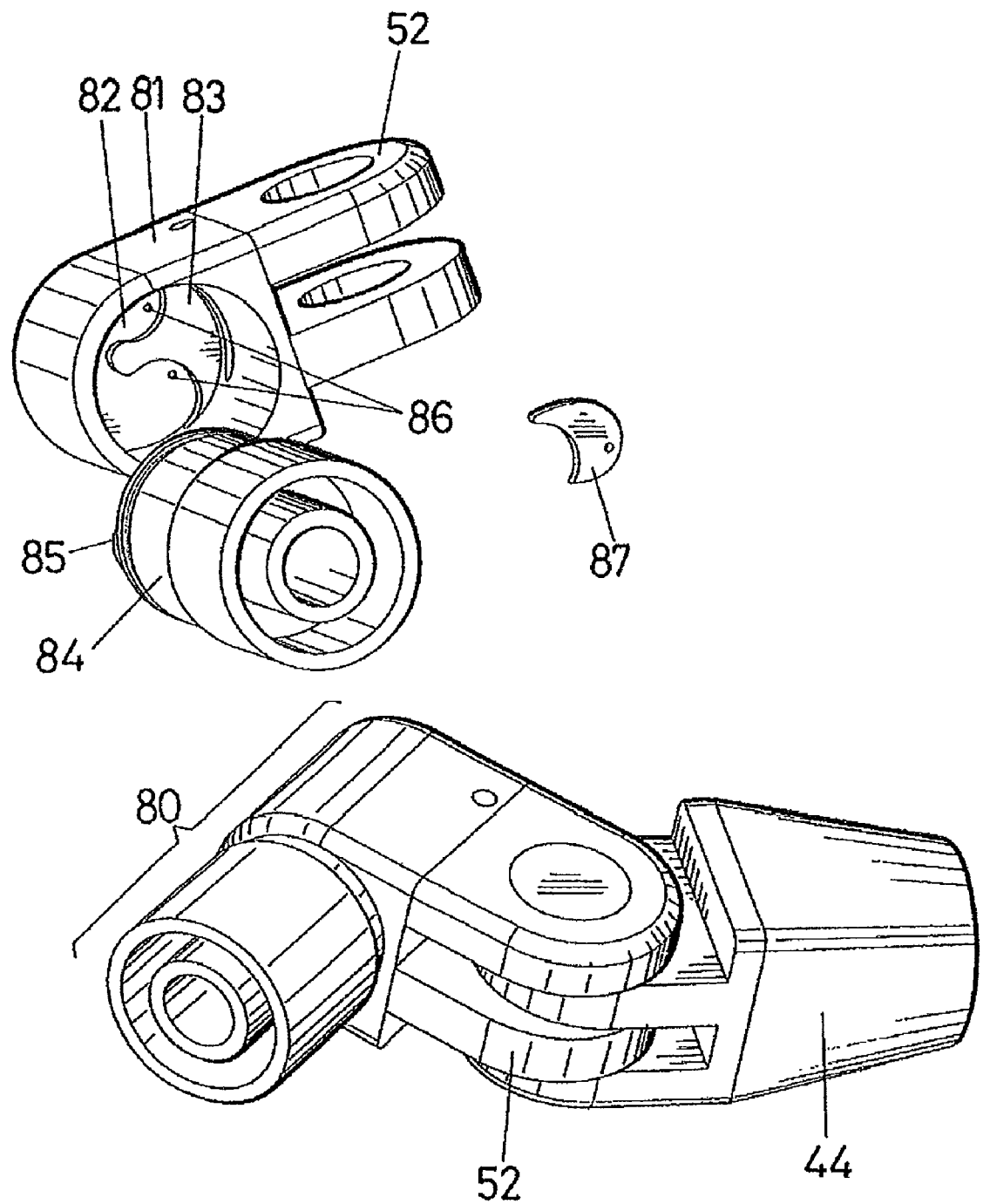
FIG. 39 shows a first embodiment of an angle limitation mechanism (ALM)
Figure 40:
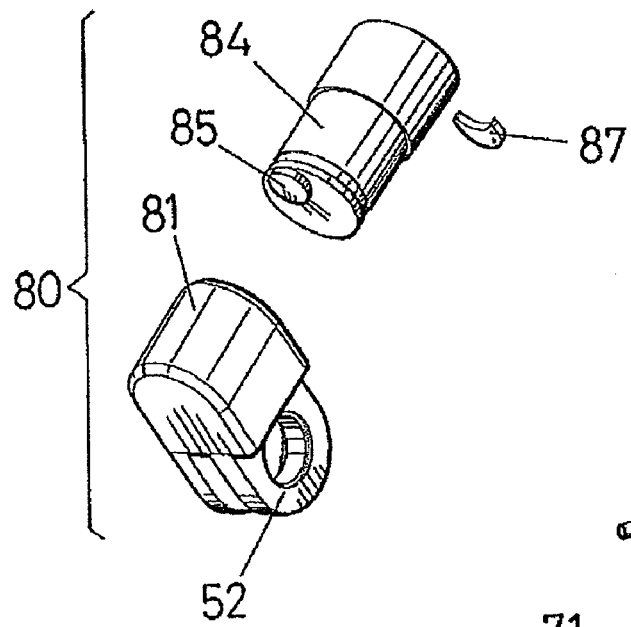
FIG. 40 shows an exploded view of the elements in FIG. 39.

One example of a preferred embodiment for an ALM (80) shown in FIGS. 39 and 40, includes an outer member or hub (81) and an inner member or shaft (84) that rotate relative to each other within a limited range around the longitudinal axis of the upper linkage assembly. The inner member or shaft (84) has a raised rotational element (85) on its surface and the outer member or hub (81) has an internal surface (83) with a groove or guide path (82) on the same. The guide path is kidney-shaped. When the inner member (84) or shaft is introduced in the outer member (81) or hub, the raised rotational element (85) can only move within the guide path (82) of the internal surface (83) of the outer member (81) or hub. Therefore, the rotation is limited by the length of the guide path (82). The length of the guide path (82) and therefore the rotation of one member (81, 84) relative to the other, can be adjusted if limiting elements (87) or pins are introduced in holes (86) made on the guide path (82) surface.

Figure 41:
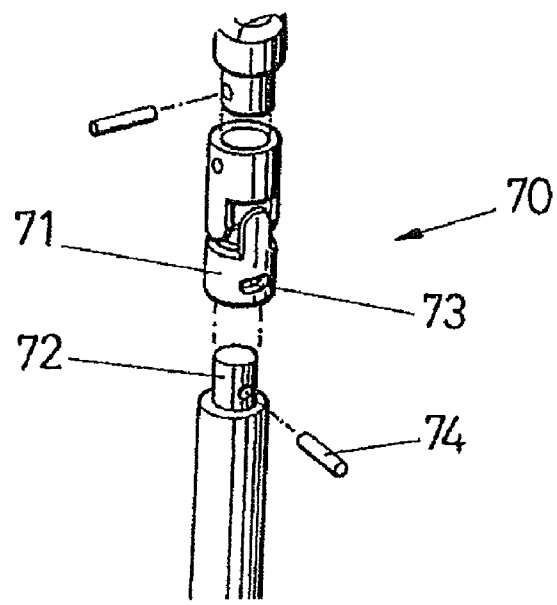
FIGS. 41 and 42 show another exemplary embodiment of an ALM.
Figure 42:
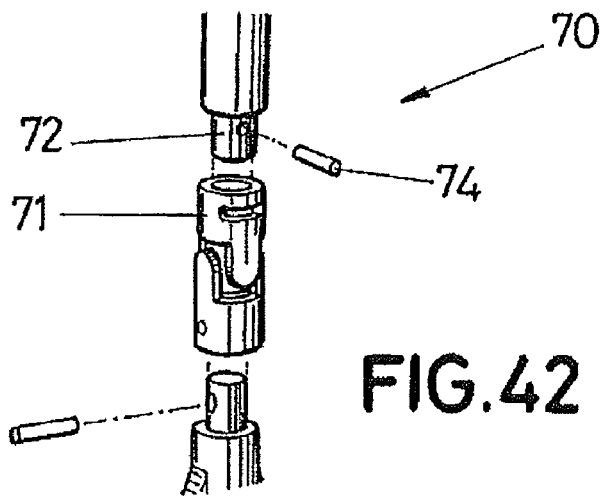
Figure 43:
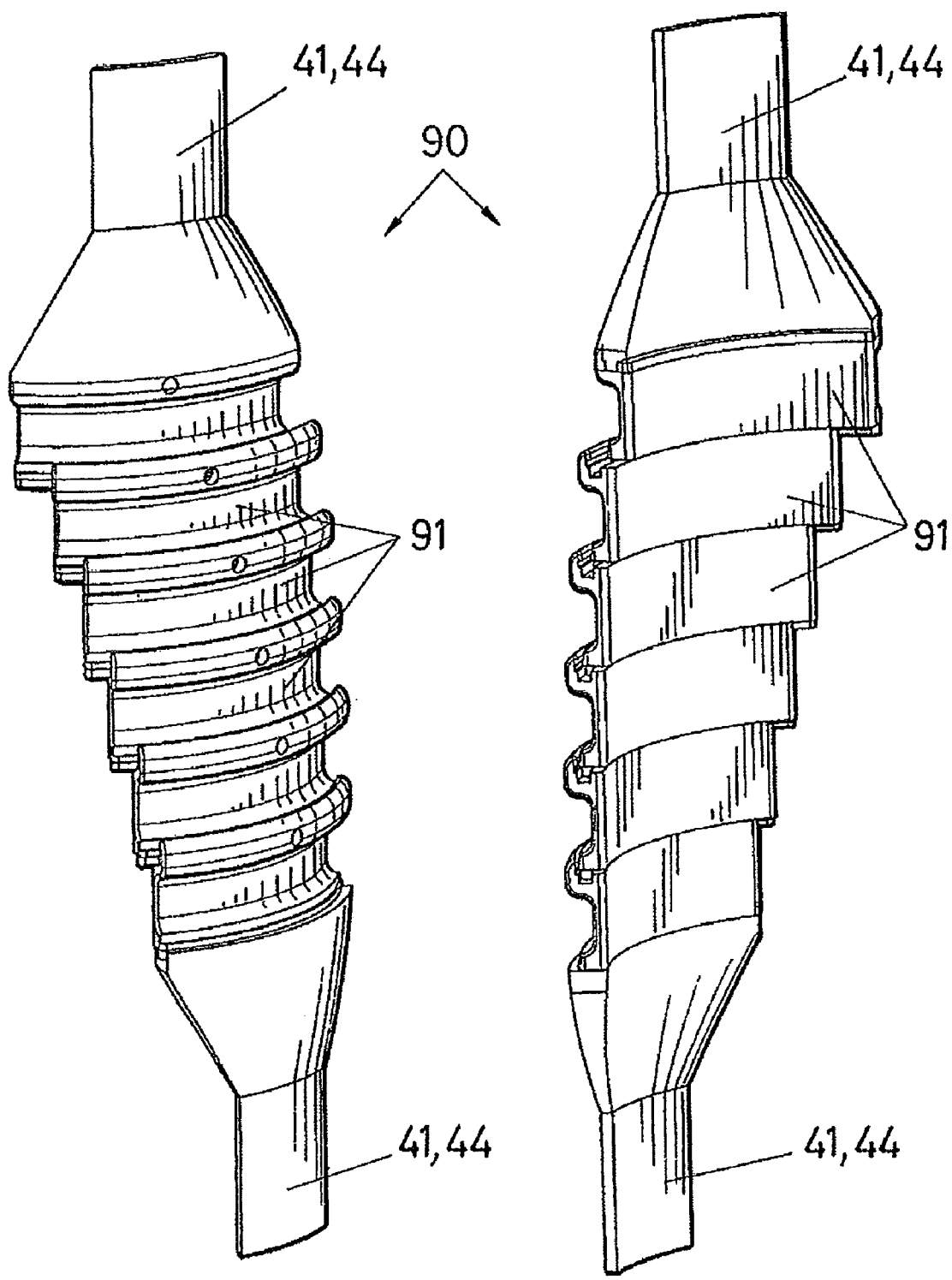
FIGS. 43 to 47 show yet another embodiment of an ALM and its components.
Figure 44:
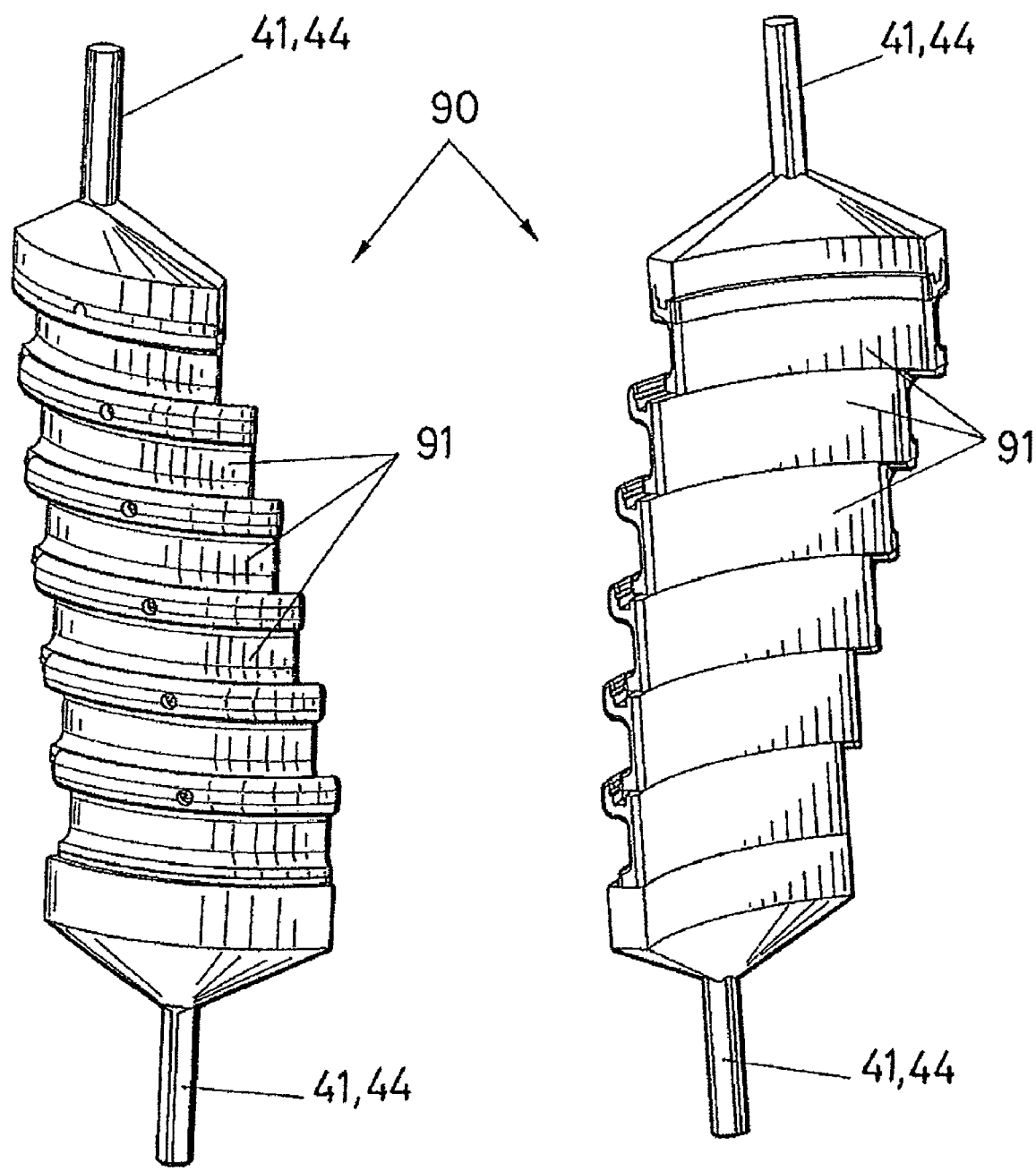
Figure 45:
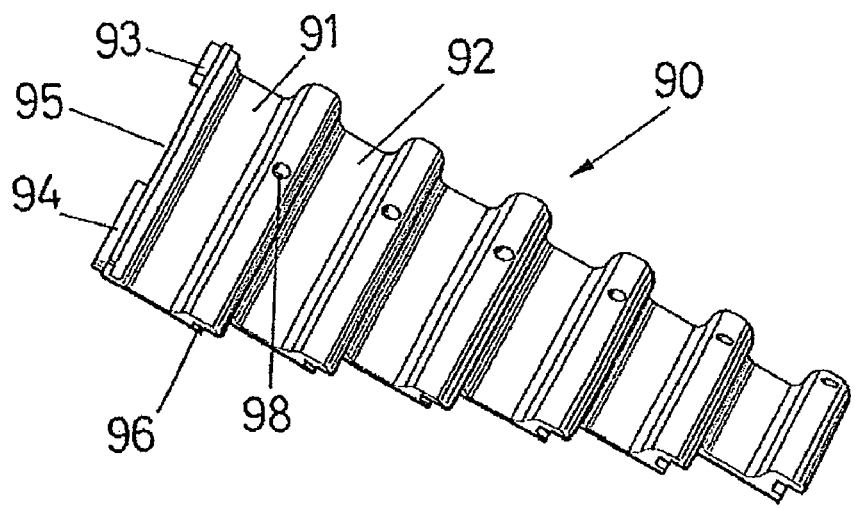
Figure 46:
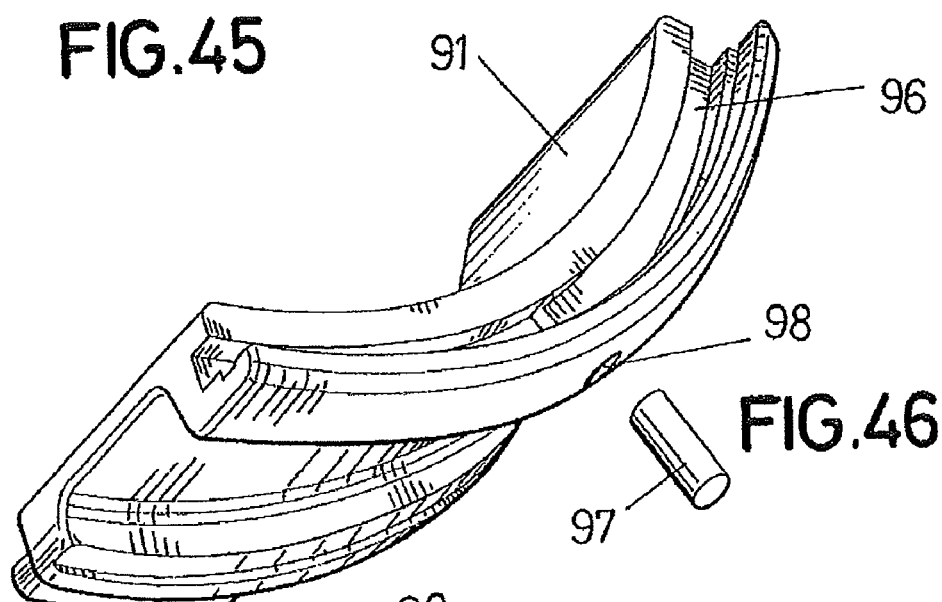
Figure 47:
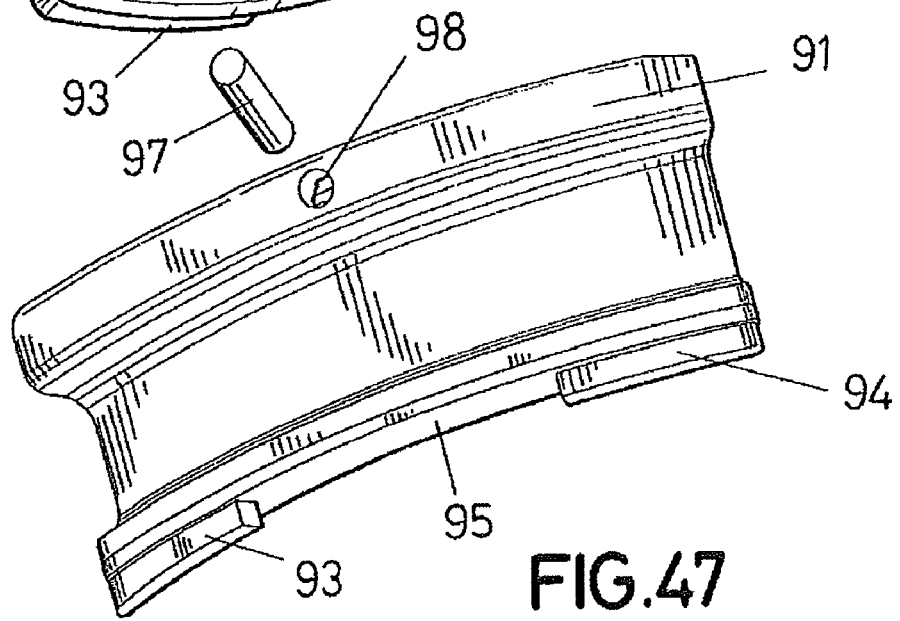
Figures 48, 49:
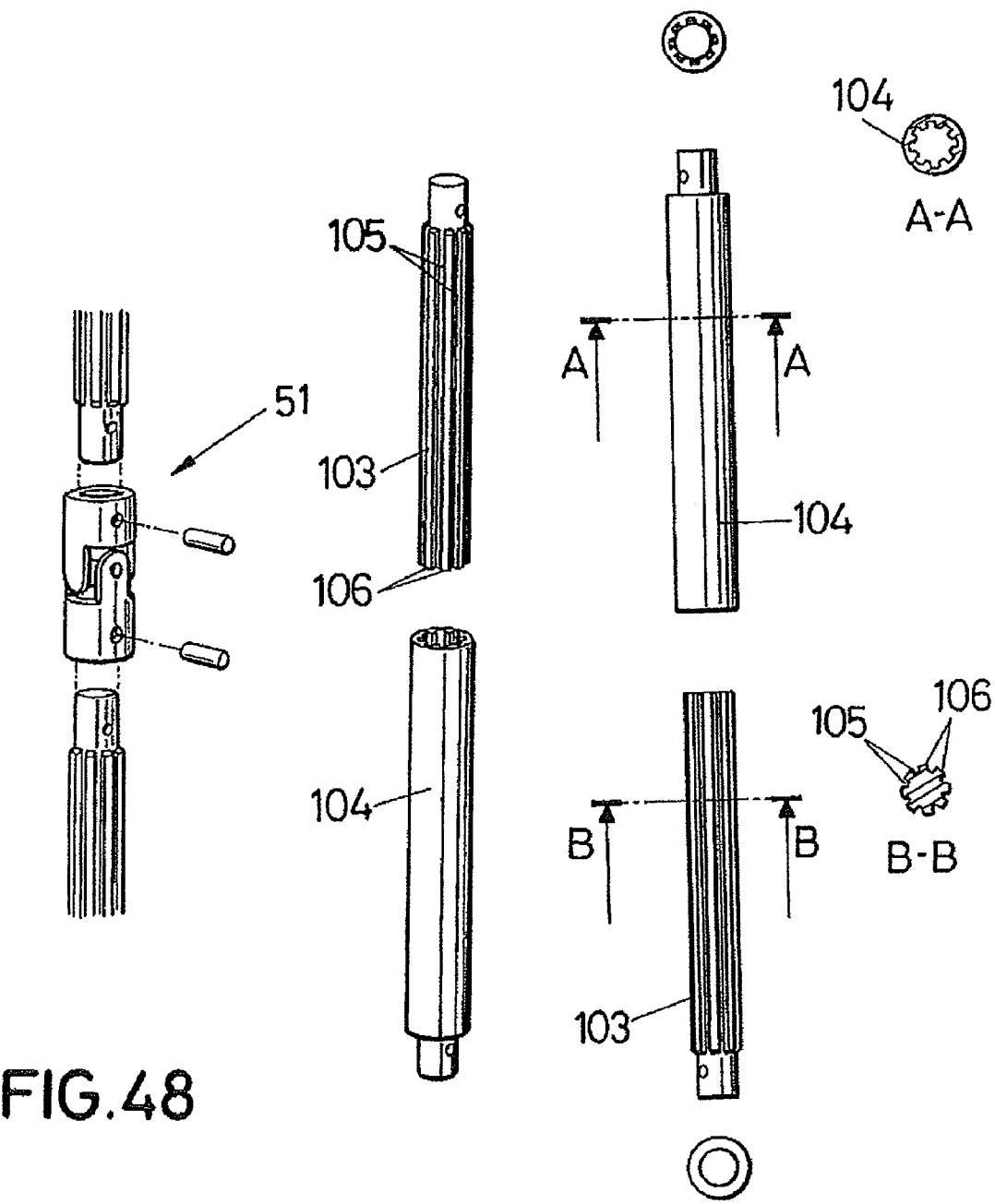
FIG. 48 shows an example of a universal or Cardan joint.
FIG. 49 shows an embodiment of an extendible linkage assembly.
Figure 50:
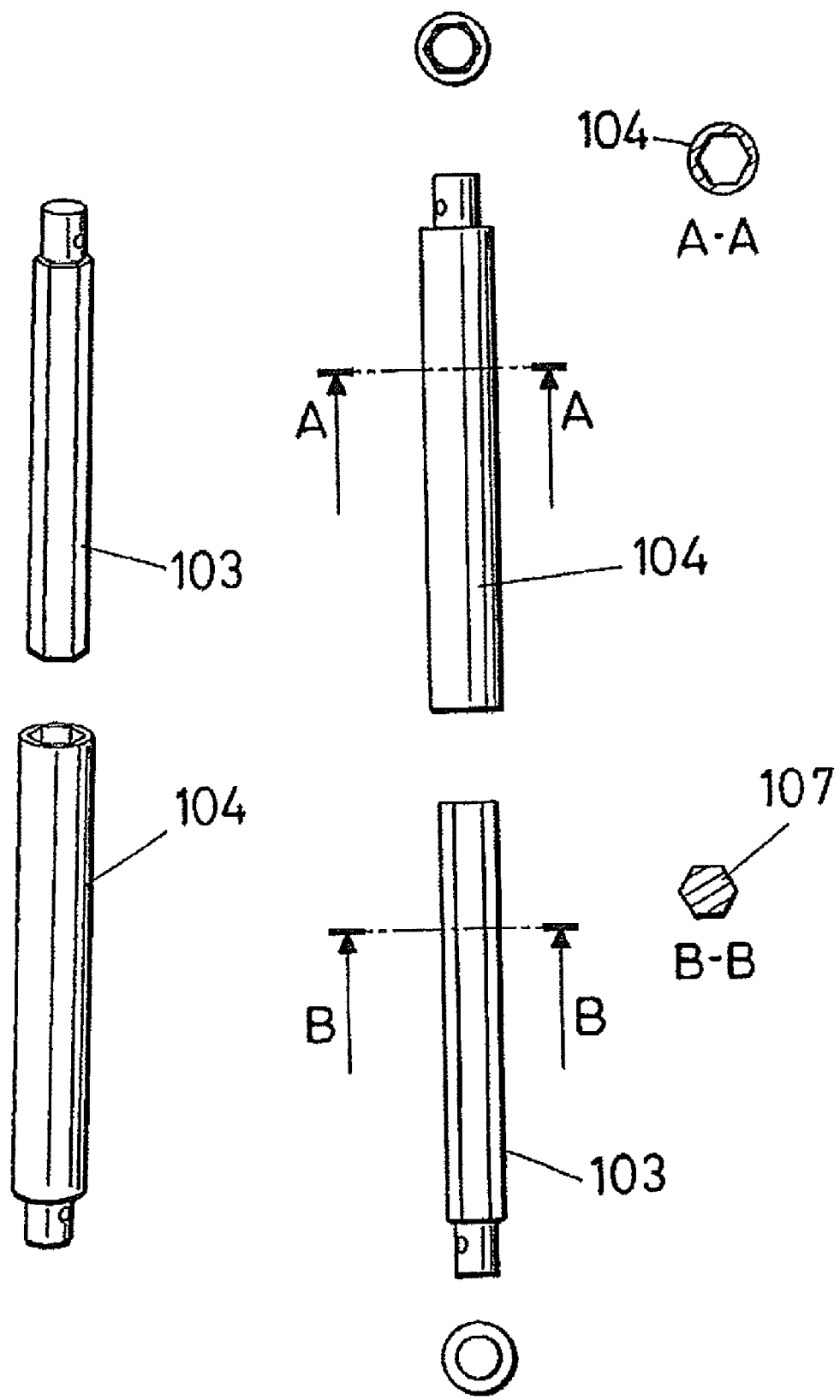
FIG. 50 shows another embodiment of an extendible linkage assembly.
Figure 51:
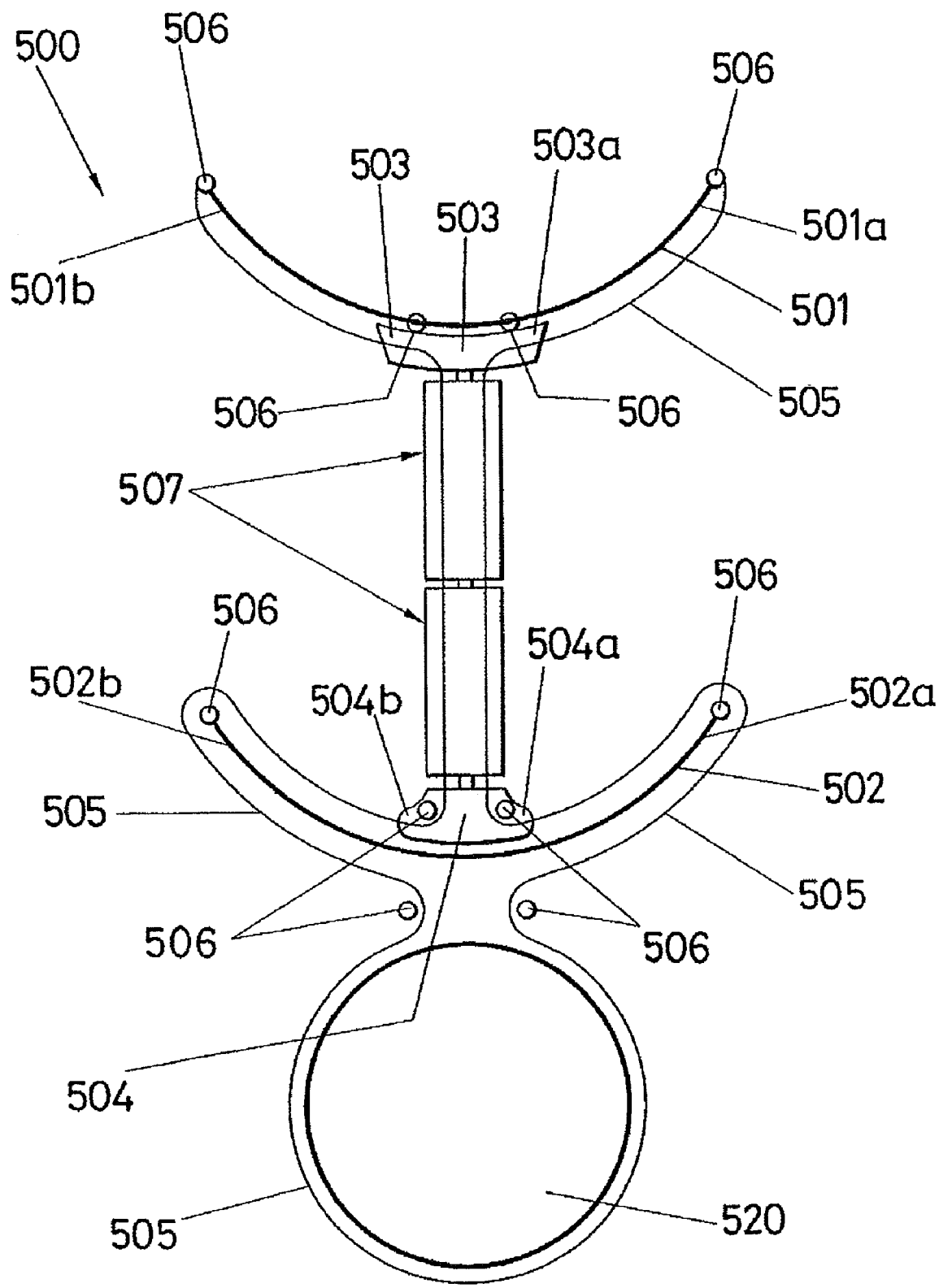
FIG. 51 shows an operation diagram of a torque transmission mechanism.
Figure 52:
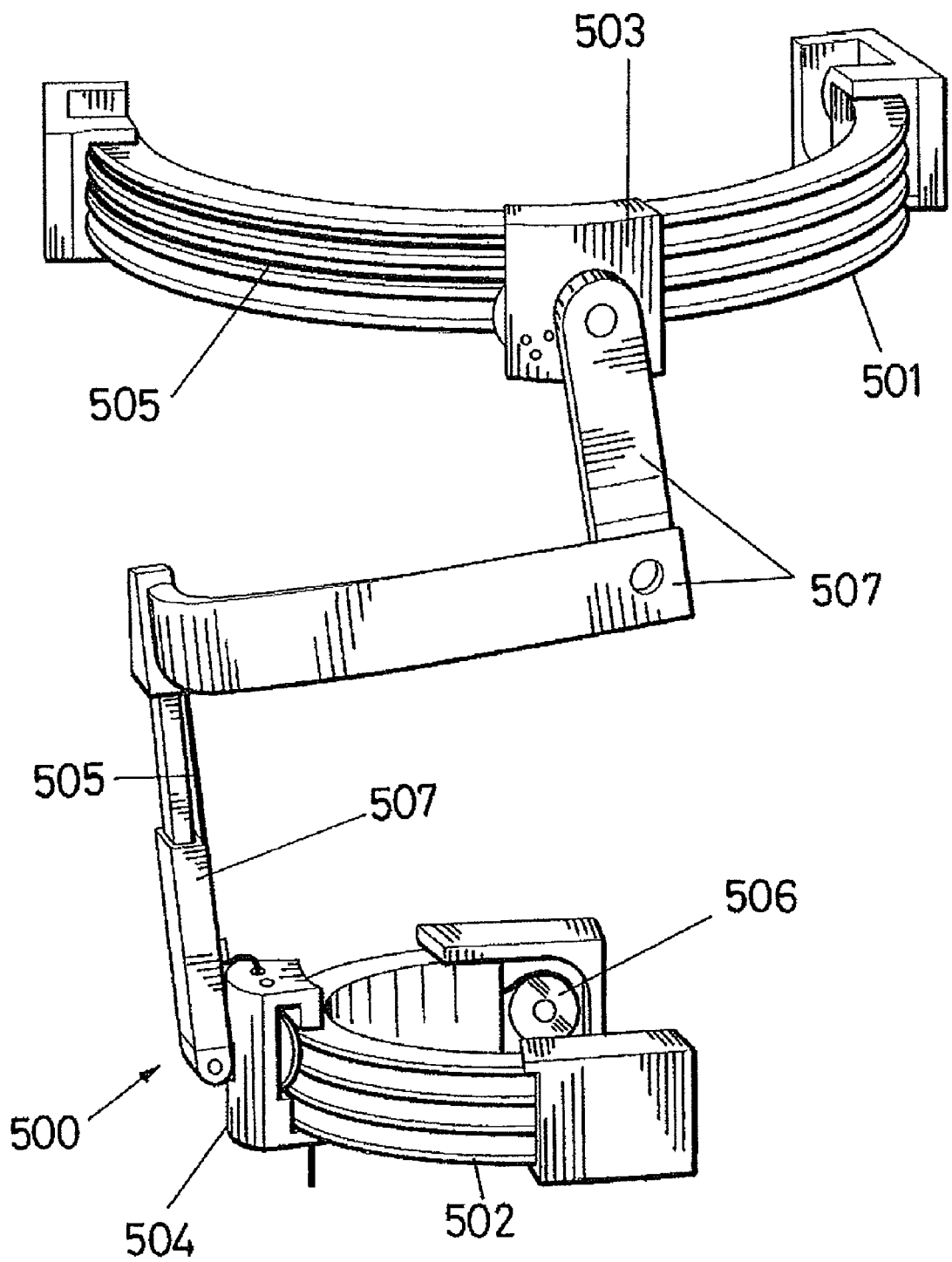
FIG. 52 shows a perspective view of a torque transmission mechanism.
Figure 53:
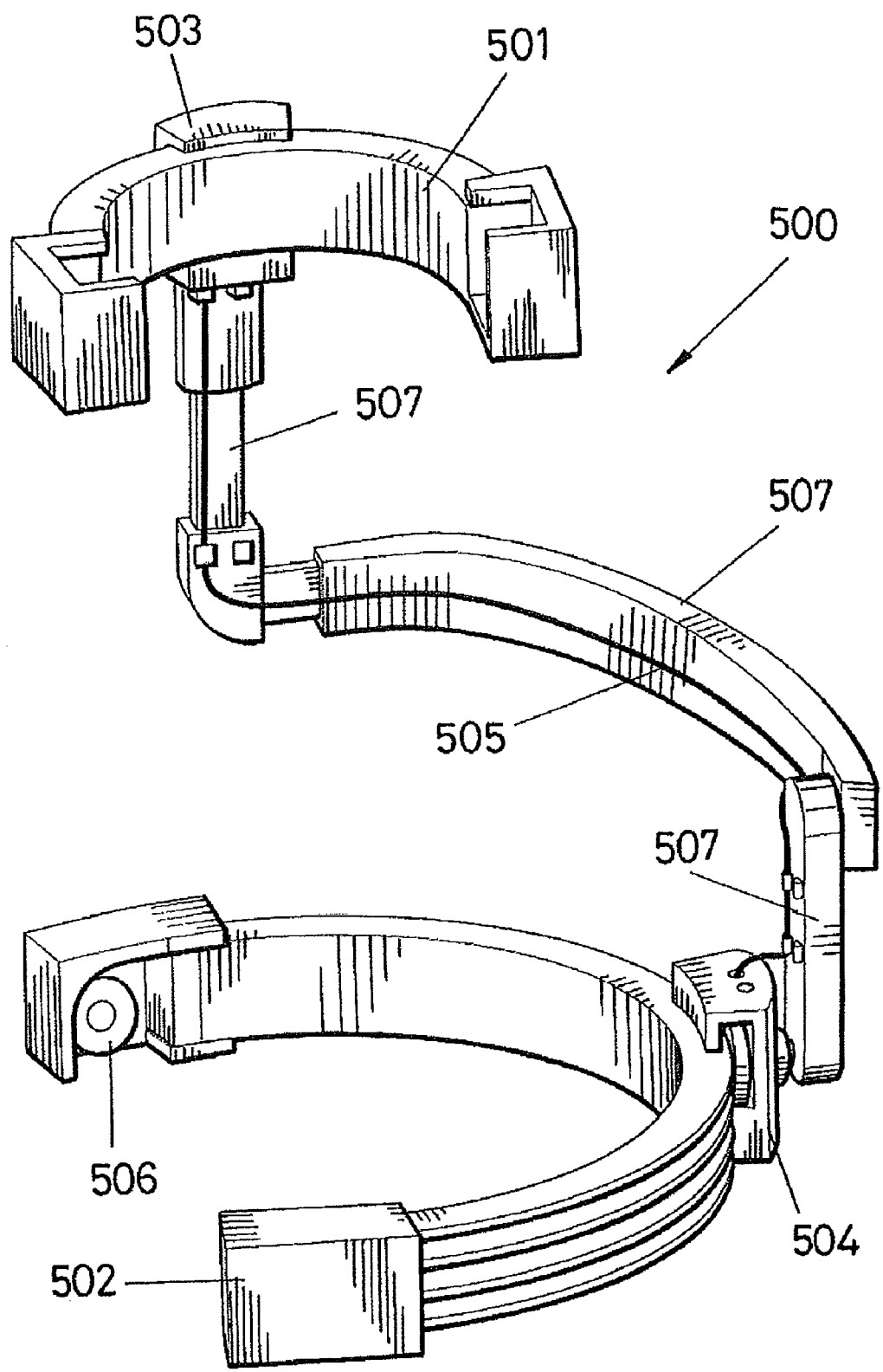
FIG. 53 shows a another perspective view of a torque transmission mechanism.
Figure 54:
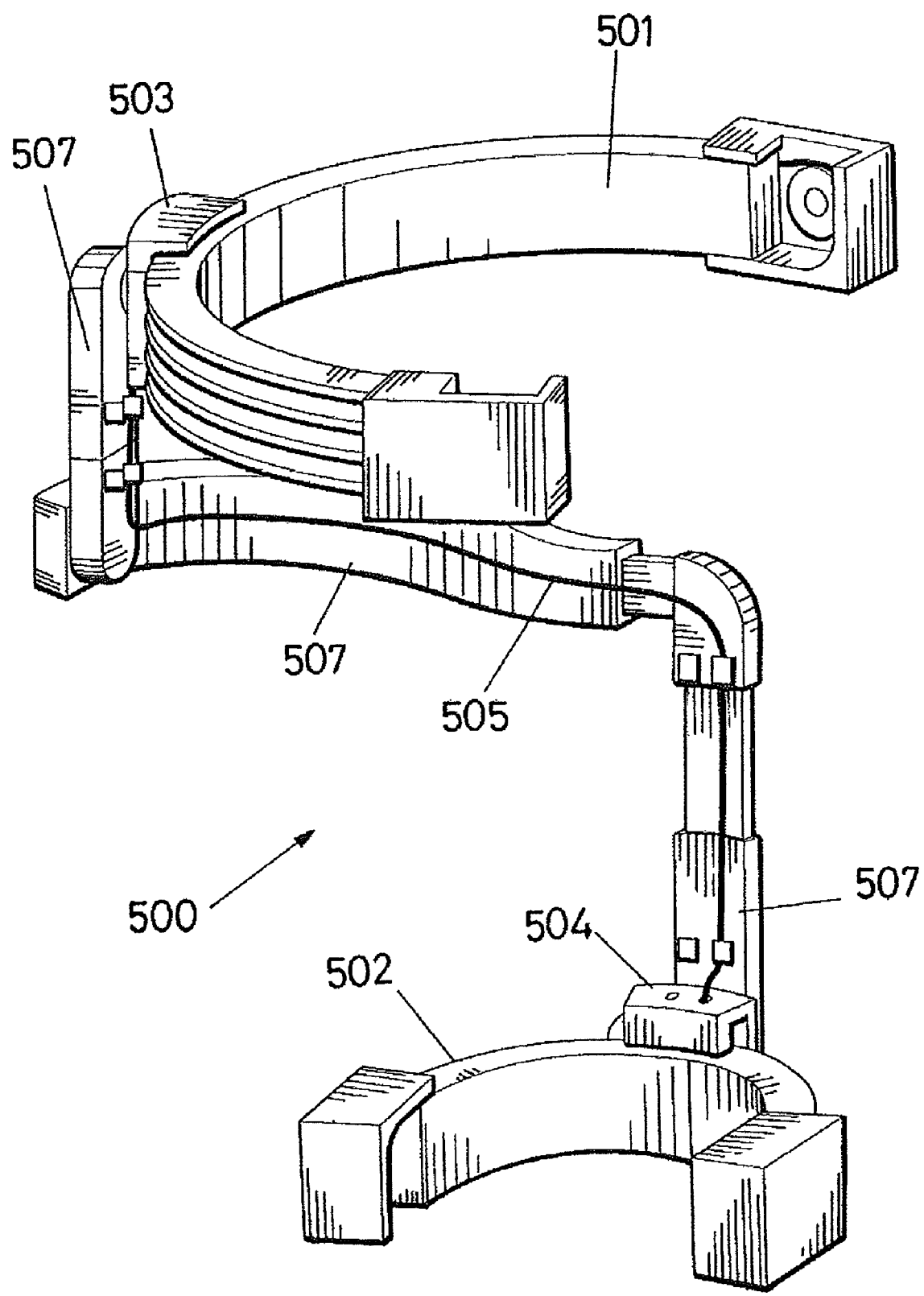
FIG. 54 shows a yet another perspective view of a torque transmission mechanism.

A second example of a preferred embodiment for an ALM (70) is illustrated in FIGS. 41 and 42. The ALM (70) has a shaft (72) and hub (71) system in which the hub (71) has a groove, slit or window (73) in its surface which is perpendicular to the longitudinal axis of rotation and the shaft (72), that is concentric with the hub (71), includes a lug (74) perpendicular to the longitudinal axis of rotation. The shaft (72) is introduced in the hub (71) and the lug (74) in the groove (73) such that the rotation of the shaft (72) with regard to the hub (71) is thus limited by the length of the groove (73), specifically when the lug (74) abut against one of both ends of the groove (73). The ALM can be placed along the upper linkage assembly (41), and therefore the same is divided into two parts so that one part connects with the ALM shaft (72) and the other with the ALM hub (71).

Yet another alternative preferred embodiment for an ALM (90), as illustrated in FIGS. 43 to 47, includes at least two partially curved plates (91, 92) overlapping one another. Each curved plate has two rails (93, 94) on its lower end and a groove (96) on its upper edge, and both rails (93, 94) are separated between them by a gap or space (95). The spaced apart rails (93, 94) of the first curved plate (91) are introduced in the groove (96) of the second curved plate (92), therefore allowing a rotational movement of one plate relative to the other. In order to limit the rotational movement, a stop pin (97) can be introduced in a hole (98) that crosses the groove (96) of the second curved plate, so that the first curved plate can only move the length of the existing gap (95) between the rails (93, 94) of the first curved plate.

The previous ALM embodiments can be placed anywhere along the upper linkage assembly (41), between the hip (5) and knee (2), dividing in that way the upper linkage assembly into two parts so that one part of the upper linkage assembly (41) links with one part of the ALM (71, 80, 91) and the other part of the upper linkage assembly with the ALM lower element (72, 84, 92).

In another embodiment (15) of the exoskeleton according the present invention and illustrated schematically in FIG. 29, the first support member located in the previous embodiments at the height of the skier's (3) hip (5) is replaced with a support member (29) located at the thigh (4), for either one or in both of the skier's (3) legs. In this construction, the first support member (29) can be attached to the thigh by a clamp (29) and the joint at the knee is a hinge joint (52) combined with a torque transmission joint (51). The clutch mechanism (170) is arranged in the lower linkage assembly (46) as in the last example which included a rotation angle limitation mechanism in the upper linkage assembly (41).

It is also possible to use a mechanism to limit the rotation at the height of the knee as previously described, which depending on the inclination of the upper linkage assembly in relation to the lower linkage assembly, limits the turning or rotation of the first support member in relation to the second support member.

The embodiments described above form a protection in the form of an exoskeleton attached to an individual at the hips, legs and feet, particularly preventing injuries in the knees, and in general any bone injury, in the manner described above; it also allows control over the skis, thus contributing to the safety of said activity.

In general, and applicable for all the preferred embodiments, the upper and lower linkage assemblies (41, 44) can be fastened to different parts of the leg by mixed clamps (108) placed along both linkage assemblies (41, 44). These clamps (108) are preferably formed by a rigid part and a soft part, like a belt, used to fasten the rigid part to the leg. The upper and lower linkage assemblies (41, 44) can be replaced by ergonomic elements, that is to say elements that adapt to the body of the user.

It is possible to use ergonomic anatomical elements independent of the linkage assemblies, such as plates made of a rigid and lightweight material placed between the leg and linkage assemblies to protect or isolate the leg from the movement thereof, making the use of the exoskeleton more comfortable. The foregoing is particularly useful when the exoskeleton is introduced or inserted in ski pants or a cover made of a flexible material and close to the cushioning in the areas where friction with the body occurs, and the device will neither be visible or uncomfortable while practicing skiing.

As previously mentioned in the first embodiment, it is possible to replace the upper linkage assembly (41) and the lower linkage assembly (44) of any of the different preferred embodiments with extendible members or linkages in order to thus adapt them to the specific measurements of each user, except in the described case of a single extendible linkage assembly which is automatically adjusted (100). The adaptation to the specific measurements of the skier or user can be done by the previously described LRM (60).

Another way of achieving the extension of the linkage assembly (40) or of the upper and lower linkage assemblies (41, 42) is by telescopic member, that is to say, the former can be formed by two members called outer sheath (104) and inner guide (103), which longitudinally slide with respect to one another as illustrated in FIG. 40. The guide (103) preferably has a circular section defining longitudinal projections (106) and grooves (105) coupled inside the sheath (104) that has a complementary section. This coupling allows carrying out an extendible linkage and, by way of the projections (106) and grooves (105), transmitting the torque in an optimal manner between the guide and the sheath. It is also possible to use other configurations which allow adjusting the linkage to the measurements of each user. It is also possible to use instead of projections (106) and grooves (105) a hexagonal-shaped (107) inner guide and an outer sheath in the extendible linkage as shown in FIG. (41).

The different components of the safety and control device object of the present invention can be made of different materials, either metals, alloys, or fibers, but they must be materials that can resist the stress to which the device is subjected.

The invention claimed is:

1. An exoskeleton to be worn by a person to provide protection and control over skis while snow skiing, comprising:
    at least one first support member configured to couple the exoskeleton to the person's body above the knee,
    at least one second support member configured to couple the exoskeleton to the person's body below the knee,
    a linkage assembly comprising an upper end and a lower end, the linkage assembly coupled at the upper end to the first support member and coupled at the lower end to the second support member, the linkage assembly generally extending along the leg when the person wears the exoskeleton;
    at least one clutch mechanism operatively coupled between two elements of the exoskeleton, allowing the clutching and unclutching of said two elements of the exoskeleton; and
    at least one sensor that detects movement, or pressure, or movement and pressure of a part of the body of the skier, the at least one sensor transmits a corresponding signal to the clutch mechanism.

2. The exoskeleton according to claim 1, wherein said at least one sensor is placed between the foot and the ski and detects movement or pressure or movement and pressure of the foot relative to the ski and transmits a corresponding signal to the clutch mechanism.

3. The exoskeleton according to claim 1, further comprising at least one artificial joint placed between two portions of the exoskeleton such that the artificial joint transmits torque between the two portions, allowing said torque transmission independently of the angular alignment between respective torque axes of both portions.

4. The exoskeleton according to claim 1, wherein the linkage assembly comprises an upper linkage assembly with a respective upper end and a lower end, and a lower linkage assembly with a respective upper end and a lower end, and wherein, when the exoskeleton is worn by the person, the upper linkage assembly extends from the first support member to about the person's knee, and the lower linkage assembly extends from about the person's knee to the second support member.

5. The exoskeleton according to claim 4, wherein the lower end of the upper linkage assembly is linked to the upper end of the lower linkage assembly by an artificial joint located about the height of the person's knee, and wherein the joint allows flexion-extension movement of the knee.

6. The exoskeleton according to claim 5, wherein the artificial joint is a hinge.

7. The exoskeleton according to claim 5, wherein the artificial joint is configured to transmit torque between respective torque axes of both linkage assemblies allowing said torque transmission independently of the angular alignment between the respective torque axes of both portions.

8. The exoskeleton according to claim 7, wherein the joint or mechanism comprises a hinge.

9. The exoskeleton according to claim 1, wherein the first support member is configured to couple the exoskeleton to the person's body at the waist or hip.

10. The exoskeleton according to claim 1, wherein the first support member is configured to couple the exoskeleton to the person's thigh.

11. The exoskeleton according to claim 3, comprising a joint that links the first support member with the linkage assembly.

12. The exoskeleton, according to claim 11, wherein the joint limits the movement or rotation in the sagittal and transverse axis of the coxofemoral joint, limiting the flexion, the extension, the abbduction and adduction of the leg to the natural or not dangerous ranges.

13. The exoskeleton, according to claim 12, wherein the ranges of rotation allowed by the joint in the sagital and transverse axis are adjustable.

14. The exoskeleton according to claim 11, wherein the joint is a double hinge joint that allows the exoskeleton to bend about two different axes.

15. The exoskeleton according to claim 1, wherein the lower end of the linkage assembly is linked to the second support member through a quick coupling mechanism that allows the user to quickly connect and disconnect the second support member to and from the linkage assembly.

16. The exoskeleton according to claim 1, further comprising one or more quick coupling mechanisms that allows the person to quickly connect and disconnect two elements of the exoskeleton.

17. The exoskeleton according to claim 4, wherein the clutch mechanism is located in the upper linkage assembly.

18. The exoskeleton according to claim 17, wherein the clutch mechanism is located between an upper part of the upper linkage assembly and a lower part of the upper linkage assembly, into which the upper linkage assembly is divided.

19. The exoskeleton according to claim 4, wherein the clutch mechanism is located in the lower linkage assembly.

20. The exoskeleton according to claim 19, wherein the lower linkage assembly is articulated in two parts, having an upper part of the lower linkage assembly and a lower part of the lower linkage assembly.

21. The exoskeleton according to claim 20, wherein the lower linking assembly is articulated by a hinge.

22. The exoskeleton according to claim 4, comprising two clutch mechanism, a clutch mechanism in the upper linkage assembly and a clutch mechanism in the lower linkage assembly.

23. The exoskeleton according to claim 1, wherein the clutch mechanism comprises:
a runner;
a rail defining a curved path along which the runner slides within limits defined by the rail, the limits being adjustable so as to vary the length of the curved path, said runner comprising a conical gear section;
a rotor comprising in one of its two sides a first gear or first pinion that meshes with the conical gear section of said runner, said rotor further comprising on its opposite side a second gear; and
a left shaft comprising a left gear and a right shaft comprising a right gear, said second gear of said rotor meshing with said left gear and said right gear, wherein the left and right shafts rotatably support respective left and right bushings; and
wherein the rotor and the bushings are each of them surrounded, at least partially, by respective bands with two free ends each of them, such that the left and right ends of the primary band surrounding the rotor are separated in the lower zone of the same, and the free ends of the bands of the left and right bushings are separated in the upper zone of the bushings, having each of the bands of the bushings a free exterior end and a free interior end, such that the free interior end of the left bushing can be in contact with the left end of the primary band or band of the rotor, and the free interior end of the band of the right bushing can be in contact with the right end of the band of the rotor, remaining free the exterior ends of the bands that surround the left and right bushings.

24. The exoskeleton according to claim 23, further comprising a spring between the left and right bushings and acts on the ends of primary band or band of the rotor so as to bias said primary band.

25. The exoskeleton according to claim 23, wherein the left and right bushings are one way free wheel type bushings such that the left bushing can only transmit the torque of the shaft in clockwise direction and the right bushing can only transmit the torque in counter-clockwise direction.

26. The exoskeleton according to claim 23, further comprising thrusters connected to the sensor and wherein the exterior ends of the bands of the bushings are shifted by action of thrusters.

27. The exoskeleton according to claim 26, wherein the sensor comprises at least one rocker arm having two ends that receives on one of the two ends a movement from a boot of the user that is transmitted to the thruster.

28. The exoskeleton, according to claim 27, further comprising a clog connected to the rail, said clog configured to surround the base or sole of the boot so as to allow play with the boot in a rear part of the clog while the front part of the boot and the front part of the clog are fixed, being a front part and a rear part of the clog configured to fit to a ski binding.

29. The exoskeleton according to claim 28, wherein the second support member is the boot and the rocker arm receives a pressure signal from movement of the boot within the clog.

30. The exoskeleton according to claim 1, wherein the clutch mechanism comprises a shaft connected to the linkage assembly, said shaft located inside a body having a cylindrical cavity with two diametrically opposed cavity flanges, a rotating actuator integral to the shaft with two integral symmetrical actuator flanges are arranged inside the cylindrical cavity forming a sealed closure against walls of the cylindrical cavity, the cavity flanges located inside the body also forming a sealed closure against the rotating actuator, the cylindrical cavity thereby divided into four cavities, such that two opposing cavities are connected by a first and a second duct diagonally traversing the rotating actuator, maintaining a same pressure in opposing cavities, and contiguous cavities defined by the two diametrically opposed cavity flanges are connected by a third and a fourth duct, that get through the body and wherein the cavities and ducts are filled with a fluid for transmitting force in hydraulic mechanisms.

31. The exoskeleton according to claim 30, wherein the third and fourth duct have non-return valves such that the non-return direction of one of the valves is opposite to the direction of the non-return valve of the other duct, said valves being activated by the sensor.

32. The exoskeleton according to claim 1, wherein the clutch mechanism comprises a gear train with a rear end connected to the linkage assembly of the exoskeleton, and a front end of the train comprising a braking wheel with an integral gear or pinion; and wherein the braking wheel is configured to contact with push buttons connected to the sensor, such that actuation of one of the push buttons on the braking wheel through a rocking arm causes the linkage assembly to become integral to the gear train through the rear end connected to the lower end of the linkage assembly.

33. The exoskeleton according to claim 32, wherein the gear train is contained in a housing that is in turn coupled to a lower part of the second support member.

34. The exoskeleton according to claim 4, further comprising a torque transmission mechanism at the height of the knee and between the upper linkage assembly and the lower linkage assembly, said torque transmission mechanism comprising an upper rail located above the knee, a lower rail located below the knee, an articulated rigid member between the upper rail and the lower rail, an upper and lower runner placed in the upper and lower rails respectively, both runners connected by an articulated rigid member, each runner with movement along each respective rail, and a cable passing through the mechanism and also passing throughout the clutch mechanism.

35. The exoskeleton according to claim 34, wherein the cable extends from the first end of the upper rail, continues through the upper runner, then the articulated rigid member, then the lower runner, then to the first end of the lower rail, then contacts the brake mechanism, extends further to the second end of the lower rail opposite to the first end, again through the lower runner, then the articulated rigid member, then the upper runner and ends in the second end of the upper rail.

36. The exoskeleton according to claim 5, further comprising at least one angle limitation mechanism that limits relative rotation between the coupling to the body of the first support member and the coupling to the artificial joint at the height of the knee of the lower end of the upper linkage assembly, so as to prevent relative rotation outside a predetermined rotational range while permitting free unrestricted relative rotation within the predetermined rotational range.

37. The exoskeleton according to claim 36 wherein the angle limitation mechanism is part of the artificial joint at the height of the knee, and comprises means for coupling the upper linkage assembly and the lower linkage assembly, such that when the knee is extended the upper linkage assembly is integral to the lower linkage assembly and when the knee is completely flexed, the upper linkage assembly has complete freedom to rotate in relation to the lower linkage assembly within limits established by said angle limitation mechanism.

38. The exoskeleton according to claim 37, wherein the angle limitation mechanism at the knee has a hub with a conical cavity with four nerves and a shaft with two projections at an end, so that depending on a position of the projections in the cavity of the hub, the range of rotational movement of the projections of the shaft in respect of the nerves in the cavity varies, and therefore the range of rotational movement of the upper end of the lower linkage assembly.

39. The exoskeleton according to claim 36, wherein the angle limitation mechanism comprises a hub comprising a groove and a shaft that rotates within the hub and further comprises a lug, the lug movable inside the groove such that ends of the groove limit the amount of relative rotation between the shaft and the hub.

40. The exoskeleton, according to claim 39, wherein the angle limitation mechanism comprises adjustable elements for changing a rotation range of one element relative to the other, the adjustable elements placed in the groove or on the lug.

41. The exoskeleton according to claim 36, wherein the angle limitation mechanism comprises at least two partially curved plates overlapping one another and linked by rails allowing both curved plates to slide relative to each other.

42. The exoskeleton according to claim 41, wherein the plates comprise adjustable stops that limit the amount by which the plates slide relative to each other.

43. The exoskeleton according to claim 36, wherein the angle limitation mechanism comprises an outer member comprising an internal surface defining a guide path and an inner member comprising a raised rotational element disposed in the guide path so that rotation of the inner member is limited by the movement of the raised rotational element in the guide path.

44. The exoskeleton, according to claim 43, wherein the angle limitation mechanism comprises at least one limiting element or pin introduced in at least one hole made on the guide path surface to adjust the length of the guide path and thereby the rotation of one member relative to the other.

45. The exoskeleton according to claim 1, wherein the linkage assembly is extendable in a dynamic manner so that it can elongate or shorten.

46. The exoskeleton according to claim 45, wherein the linkage assembly comprises telescopic members.

47. The exoskeleton according to claim 1, comprising at least one length regulating mechanism along the linkage assembly that makes the linkage assembly extendable and allows the user to quickly connect and disconnect two parts of the exoskeleton, said length regulating mechanism comprising an inner member comprising a plurality of holes and an outer member comprising at least one sphere that is selectively insertable using a push button in one of the holes so as to adjust the relative position of the inner member and the outer member.

48. The exoskeleton according to claim 1, comprising
at least one second support member for each leg,
at least one linkage assembly for each leg, and
at least one clutch mechanism for each leg.

49. The exoskeleton according to claim 3, wherein the artificial joint is an elastic joint.

50. The exoskeleton according to claim 3, wherein the artificial joint is a universal or Cardan joint.

51. The exoskeleton according to claim 1, wherein the second support member is a boot.

52. The exoskeleton according to claim 1, wherein the second support member is a binding of the ski.

53. The exoskeleton according to claim 1, wherein the second support member is a ski.

54. The exoskeleton according to claim 30, wherein the predetermined rotational range is adjustable by the person wearing the exoskeleton.

55. The exoskeleton according to claim 1, wherein the first support member is rigid.

56. The exoskeleton according to claim 55, wherein the first support member is a belt.

57. The exoskeleton according to claim 56, wherein the belt comprises two parts, a surrounding part and a front part, linked together to form a rigid whole by belt connections that are placed on the free ends of the surrounding part and the front part, so that said belt connections are superposed one on top of the other to form one element, and are fixed by a belt closure.

58. The exoskeleton according to claim 1, wherein the sensor is located between the second support member and the clutch mechanism.

59. The exoskeleton according to claim 1, wherein the sensor is located between the boot of the skier and the booty of the boot thereof.

60. The exoskeleton according to claim 1, wherein the sensor is located between the boot of the skier and a binding of the ski.

61. The exoskeleton according to claim 1, comprising at least two sensors, a first left sensor that detects movements of one foot towards the left side and a second right sensor that detects movements of said one foot towards the right side.

62. The exoskeleton according to claim 1, wherein the sensor is mechanical.

63. The exoskeleton according to claim 1, wherein the sensor is electrical.

64. The exoskeleton according to claim 1, wherein the sensor is hydraulic.

65. Exoskeleton, according to claim 2, wherein a mechanism is placed between the foot and the exoskeleton to prevent direct action of the exoskeleton on the sensor.

66. Exoskeleton, according to claim 1, wherein the two elements of the exoskeleton are clutched or coupled by default when the mechanism receives no action from the sensor.

67. Exoskeleton, according to claim 1, wherein the two elements of the exoskeleton are unclutched or not coupled by default when the mechanism receives no action from the sensor.

68. Exoskeleton, according to claim 1, wherein the clutch mechanism clutches or couples the two elements of the exoskeleton when an action is received from the sensor, generating a high resistance torque in only one specific rotational direction, leaving the opposite rotational direction free.

69. Exoskeleton, according to claim 1, wherein the clutch mechanism clutches or couples the two elements of the exoskeleton when an action is received from the sensor, generating a high resistance torque in both rotational directions.

70. Exoskeleton, according to claim 1, wherein the clutch mechanism is of the type that makes said clutching or unclutching between both elements of the exoskeleton progressive.

71. Exoskeleton, according to claim 1, wherein the clutching or unclutching of said two elements of the exoskeleton is based on a signal from the at least one sensor.

72. An exoskeleton to be worn by a person to provide protection and control over skis while snow skiing, comprising:
- first support means for coupling the exoskeleton to the person's body above the knee;
- second support means for coupling the exoskeleton to the person's body below the knee;
- a linkage assembly comprising an upper end and a lower end, the linkage assembly coupled at the upper end to the first support means and coupled at the lower end to the second support means, the linkage assembly generally extending along the leg when the person wears the exoskeleton;
- clutch means for clutching and unclutching two elements of the exoskeleton; and
- sensor means for detecting movement, or pressure, or movement and pressure of a foot of the skier, the sensor means transmitting a corresponding signal to the clutch means.

73. A method of providing and protection and control while snow skiing, comprising:
- providing an exoskeleton comprising a linkage assembly comprising an upper end and a lower end;
- coupling the upper end of the linkage assembly above the knee;
- coupling the lower end of the linkage assembly below the knee;
- detecting movement, or pressure, or movement and pressure of a foot, the step of detecting movement further comprising transmitting a signal that corresponds to the detected movement or pressure or movement and pressure of the foot; and
- clutching and unclutching two elements of the exoskeleton based on a predetermined value or values of the transmitted signal.

* * * * *